United States Patent

Gavardinas et al.

(10) Patent No.: US 7,994,164 B2
(45) Date of Patent: Aug. 9, 2011

(54) MINERALOCORTICOID RECEPTOR ANTAGONISTS AND METHODS OF USE

(75) Inventors: Konstantinos Gavardinas, Monrovia, IN (US); Prabhakar Kondaji Jadhav, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 123 days.

(21) Appl. No.: 12/330,539

(22) Filed: Dec. 9, 2008

(65) Prior Publication Data

US 2009/0163472 A1   Jun. 25, 2009

Related U.S. Application Data

(60) Provisional application No. 61/014,776, filed on Dec. 19, 2007.

(51) Int. Cl.
*A61K 31/535* (2006.01)
*C07D 413/14* (2006.01)

(52) U.S. Cl. .................... 514/233.8; 544/139
(58) Field of Classification Search .............. 544/139; 514/233.8
See application file for complete search history.

(56) References Cited

U.S. PATENT DOCUMENTS

| 4,072,756 | A | 2/1978 | Arlesheim et al. |
| 4,999,363 | A | 3/1991 | Oshima et al. |
| 5,024,912 | A | 6/1991 | Neishi et al. |
| 5,378,701 | A | 1/1995 | Ohshima et al. |
| 5,395,610 | A | 3/1995 | King |

FOREIGN PATENT DOCUMENTS

| EP | 0 345 747 | 12/1989 |
| WO | WO 99/33786 | 7/1999 |
| WO | WO 00/59884 | 10/2000 |
| WO | 2004052847 | 6/2004 |
| WO | WO 2004/052847 | 6/2004 |
| WO | 2005066153 A1 | 7/2005 |
| WO | WO 2005/066161 | 7/2005 |
| WO | 2005110992 | 11/2005 |
| WO | WO 2006/015259 | 2/2006 |
| WO | 2006053024 | 5/2006 |
| WO | 2008053300 | 5/2008 |
| WO | 2008119918 | 10/2008 |
| WO | 2009080725 | 7/2009 |
| WO | 2009080730 | 7/2009 |
| WO | 2009094157 | 7/2009 |
| WO | 2010104721 A1 | 9/2010 |

OTHER PUBLICATIONS

Byrn et al., Solid-Sate Chemistry of Drugs, Second Edition, 1999, pp. 233-247.*
Cheng et al., "Synthesis and Structure-Activity Relationships of 9-Substituted Acridines as Endothelia-A Receptor Antagonists," *Bioorg. Med. Chem. Let.*, vol. 6, No. 24, pp. 2999-3002 (1996).
Jadhav, "Discovery of orally bioavailable, non-steroidal mineralocorticoid receptor antagonists: A tale of three platforms," slides for MR Antagonist Atlants ACS Meeting, Mar. 27, 2006.
Jadhav, Discovery of First, Orally Bioavailable, Non-Steroidal Mineralcorticoid Receptor Antagonists, slides, Feb. 11, 2003.
International Search Report and Written Opinion/ISA of the International Searching Authority of International Application No. PCT/US2008/085997, Mailing Date Mar. 27, 2009.
Reply to Written Opinion for International Application No. PCT/US2008/085997, Oct. 2009.
Notification of Transmittal of the International Preliminary Report on Patentability for International Application No. PCT/US2008/085997, Mar. 2010.

* cited by examiner

*Primary Examiner* — Rebecca Anderson
(74) *Attorney, Agent, or Firm* — Francis O. Ginah; Alexander Wilson

(57) ABSTRACT

The present invention provides a compound of Formula (I):

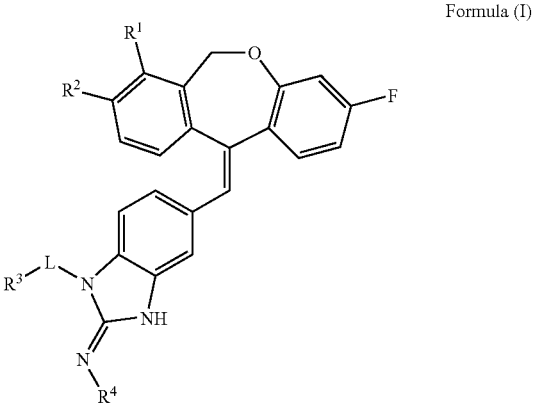

Formula (I)

or a pharmaceutically acceptable salt thereof; pharmaceutical compositions comprising a compound of Formula (I) in combination with a suitable carrier, diluent, or excipient; and methods for treating physiological disorders, particularly congestive heart failure, hypertension, diabetic nephropathy, or chronic kidney disease, comprising administering a compound of Formula (I), or a pharmaceutically acceptable salt thereof.

19 Claims, No Drawings

MINERALOCORTICOID RECEPTOR ANTAGONISTS AND METHODS OF USE

This application claims the benefit of U.S. Provisional Patent Application No. 61/014,776, dated Dec. 19, 2007.

The present invention relates to tricyclic compounds that are useful as therapeutic agents in the treatment of physiological disorders responsive to mineralocorticoid receptor antagonists, to pharmaceutical compositions comprising the compounds, to methods of using the compounds to treat physiological disorders in patients, and to intermediates and processes useful in the synthesis of the compounds.

Aldosterone, the primary endogenous mineralocorticoid, regulates hemodynamic homeostasis by promoting sodium and water reabsorption and potassium excretion following interaction with the mineralocorticoid receptor (MR). Because of aldosterone's role in maintaining electrolyte and water balance, MR antagonists have been used for the treatment of numerous physiological disorders including hypertension, hypokalemia, myocardial arrhythmias, Bartter's Syndrome, as well as disorders of primary or secondary hyperaldosteronism such as Conn's Syndrome. More recently, MR antagonists have been used in the treatment of congestive heart failure and acute myocardial infarction. In addition, MR antagonists have also proven effective in pre-clinical models of kidney disease and in combination with standard therapy to reduce proteinuria in patients suffering from renal disorders such as chronic kidney disease including diabetic nephropathy.

However, existing MR antagonists produce concomitant effects which limit their safety and/or effectiveness. For example, spironolactone, a potent MR antagonist, is nonselective and cross reacts with other nuclear hormone receptors (e.g. the androgen receptor (AR), the progesterone receptor (PR), or the glucocorticoid receptor (GR)) which mediate other physiological processes. Spironolactone therapy has been associated with hyperkalemia as well as gynecomastia, erectile dysfunction, reduced libido, irregular menses, as well as gastric distress. Eplerenone, though selective for MR relative to the other nuclear hormone receptors, has also been associated with hyperkalemia. Thus, there remains a need in the art for alternatives to current MR antagonist therapy.

The object of the present invention is to provide nonsteroidal MR ligands which possess MR antagonist activity. As a preferred embodiment, it is an object to provide nonsteroidal MR antagonists which bind to MR with greater affinity relative to AR, PR, and GR. As a more preferred embodiment, it is an object of the present invention to provide nonsteroidal MR antagonists which bind to MR with greater affinity relative to AR, PR, and GR, and which posses potent reno- or cardio-protective activity. As an even more preferred embodiment, it is an object of the present invention to provide nonsteroidal MR antagonists which bind to MR with greater affinity relative to AR, PR, and GR, and which posses potent reno- or cardio-protective activity, but with a reduced incidence or likelihood of producing hyperkalemia.

An important consideration for any therapeutic agent is whether the agent is likely to cause a prolongation of the QT interval. A central mechanism by which therapeutic agents may induce a prolongation of the QT interval is by blocking the hERG channels in cardiac muscle. Blockage of the hERG channel prevents passage of potassium ions across cardiac cell membranes resulting in prolongation of the action potentials of the cells, which could lead to dangerous cardiac arrhythmias. Thus, a further preferred embodiment of the present invention is to provide MR antagonists with a reduced incidence or likelihood of blocking hERG channels.

Tricyclic MR ligands are known in the art. For example WO 04/052847 and WO 05/066161 disclose tricyclic steroid hormone receptor modulators which are useful for treating disorders susceptible to mineralocorticoid receptor or glucocorticoid receptor modulation. The present invention is directed to the discovery that certain novel tricyclic compounds, as given by Formula (I) below, have particular profiles of activity, as evidenced by in vitro and in vivo testing, which indicate that they have utility in the treatment or prevention of disorders responsive to mineralocorticoid receptor antagonist therapy. In particular, exemplified compounds of Formula (I) are potent MR ligands which antagonize the mineralocorticoid receptor.

Accordingly, the present invention provides a compound of Formula (I)

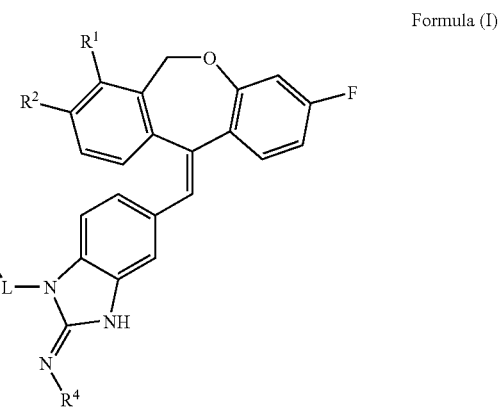

Formula (I)

wherein, $R^1$ and $R^2$ each independently represent hydrogen or fluoro;

L represents —$(CH_2)_2$—, —$CH(CH_3)$—$CH_2$—, or a direct bond;

$R^3$ represents hydrogen or a group of the formula:

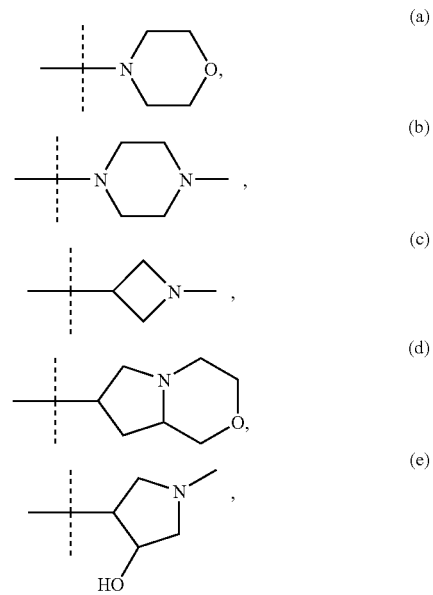

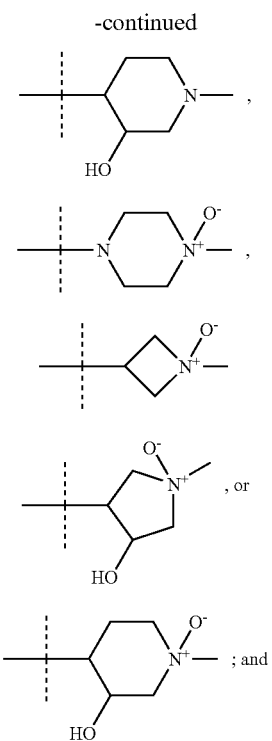

R⁴ represents —CN or —C(O)NH₂, or a pharmaceutically acceptable salt thereof.

In another embodiment, the present invention provides a method of treating or preventing congestive heart failure, diabetic nephropathy, chronic kidney disease, hypertension, hypokalemia, myocardial arrhythmia, Bartter's Syndrome, primary or secondary hyperaldosteronism, or Conn's Syndrome, comprising administering to a patient in need thereof an effective amount of a compound of Formula (I), or a pharmaceutically acceptable salt thereof. As a more particular aspect, the present invention provides a method for treating or preventing congestive heart failure, hypertension, diabetic nephropathy, or chronic kidney disease.

Further, the present invention provides a compound of Formula (I), or a pharmaceutically acceptable salt thereof, for use in the treatment or prevention of congestive heart failure, diabetic nephropathy, chronic kidney disease, hypertension, hypokalemia, myocardial arrhythmia, Bartter's Syndrome, primary or secondary hyperaldosteronism, or Conn's Syndrome. More particularly, the invention provides a compound of Formula (I), or a pharmaceutically acceptable salt thereof, for use in the treatment or prevention of congestive heart failure, hypertension, diabetic nephropathy, or chronic kidney disease. In addition, the present invention provides a compound of Formula (I), or a pharmaceutically acceptable salt thereof, for use in therapy.

In another embodiment, the present invention provides the use of a compound of Formula (I), or a pharmaceutically acceptable salt thereof for the manufacture of a medicament for the treatment or prevention of congestive heart failure, diabetic nephropathy, chronic kidney disease, hypertension, hypokalemia, myocardial arrhythmia, Bartter's Syndrome, primary or secondary hyperaldosteronism, or Conn's Syndrome. More particularly, the present invention provides the use of a compound of Formula (I), or a pharmaceutically acceptable salt thereof for the manufacture of a medicament for the treatment or prevention of congestive heart failure, hypertension, diabetic nephropathy, or chronic kidney disease.

In addition, the present invention provides a pharmaceutical composition comprising a compound of Formula (I), or a pharmaceutically acceptable salt thereof, in combination with one of more pharmaceutically acceptable carriers, diluents, or excipients. More particularly, the present invention provides a pharmaceutical composition for the treatment or prevention of congestive heart failure, hypertension, diabetic nephropathy, or chronic kidney disease, comprising a compound of Formula (I), or a pharmaceutically acceptable salt thereof, in combination with one of more pharmaceutically acceptable carriers, diluents or excipients.

The present invention also encompasses novel intermediates and processes useful for the synthesis of a compound of Formula (I).

The present invention also relates to solvates of the compound of Formula (I) or pharmaceutically acceptable salts of compounds of Formula (I). As such, when used herein the term "Formula (I)", or any particular compound of Formula (I), includes within its meaning any solvate of the compound. Examples of pharmaceutically acceptable salts and methods for their preparation are well within the knowledge of those skilled in the art. See for example, Stahl et al., "Handbook of Pharmaceutical Salts: Properties, Selection and Use," VCHA/Wiley-VCH, (2002); Gould, P. L., "Salt selection for basic drugs," *International Journal of Pharmaceutics*, 33: 201-217 (1986); Berge et al., "Pharmaceutical Salts," *Journal of Pharmaceutical Sciences*, 66, No. 1, (January 1977); and Bastin et al. "Salt Selection and Optimization Procedures for Pharmaceutical New Chemical Entities," *Organic Process Research and Development*, 4: 427-435 (2000). Particular mention is made of the hydrochloride, maleate, and mesylate salts of compounds of Formula (I).

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. Except where specifically set forth herein, all such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981, as well as those techniques provided in the Schemes, Preparations, and Examples herein.

Specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981, as well as those techniques provided in the Schemes, Preparations, and Examples herein. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

The terms "R" and "S" are used herein as commonly used in organic chemistry to denote specific configurations of a chiral center. The terms "(±)", "R/S" or "RS" refer to a racemic configuration of a chiral center. A partial list of priorities and a discussion of stereochemistry is contained in "Nomenclature of Organic Compounds: Principles and Practice", (J. H. Fletcher, et al., eds., 1974). As will be appreciated by one of ordinary skill in the art, molecules containing a carbon-carbon or carbon-nitrogen double bond may exist as geometric isomers. Two methods are commonly used to designate the specific isomers, the "cis-trans" method and the "E and Z" method depending on whether the groups attached to each of the double bonded atoms are the same or different. A discussion of geometric isomerism and the naming of specific isomers is found in March, "Advanced Organic Chemistry", John Wiley & Sons, 1992, Chapter 4. All such geometric isomers, as well as mixtures of individual isomers, are contemplated and provided by the present invention.

Compounds of the present invention may be formulated as part of a pharmaceutical composition. As such, a pharmaceutical composition comprising a compound of Formula (I), or a pharmaceutically acceptable salt thereof, in combination with a pharmaceutically acceptable carrier, diluent or excipient is an important embodiment of the invention. Examples of pharmaceutical compositions and methods for their preparation are well known in the art. See, e.g. REMINGTON: THE SCIENCE AND PRACTICE OF PHARMACY (A. Gennaro, et al., eds., 19$^{th}$ ed., Mack Publishing (1995)). Illustrative compositions comprising compounds of Formula (I) include, for example: A compound of Formula (I) in suspension with 0.5% carboxy methylcellulose, 0.25% Polysorbate 80 and 2.7% NaCl; or a compound of Formula I in suspension with 1% carboxy methylcellulose and 0.25% Polysorbate 80; or a compound of Formula I in suspension with 1% carboxy methylcellulose, 0.25% Polysorbate 80, and 0.05% AntiFoam 1510™ in purified water. It will be understood, however, that a preferred composition of the present invention comprises a compound of Formula (I), or a pharmaceutically acceptable salt thereof, formulated in a capsule or tablet.

A compound of Formula (I), or a composition comprising a compound of Formula (I) can be administered by any route which makes the compound bioavailable, including oral and parenteral routes.

One of skill in the art will appreciate that particle size can affect the in vivo dissolution of a pharmaceutical agent which, in turn, can affect absorption of the agent. "Particle size" as used herein, refers to the diameter of a particle of a pharmaceutical agent as determined by conventional techniques such as laser light scattering, laser diffraction, Mie scattering, sedimentation field flow fractionation, photon correlation spectroscopy, and the like. Where pharmaceutical agents have poor solubility, small or reduced particle sizes may help dissolution and, thus, increase absorption of the agent. Amidon et al., *Pharm. Research*, 12; 413-420 (1995). Methods for reducing or controlling particle size are conventional and include milling, wet grinding, micronization, and the like. Another method for controlling particle size involves preparing the pharmaceutical agent in a nanosuspension. A particular embodiment of the present invention comprises a compound of Formula (I), or a pharmaceutical composition comprising a compound of Formula (I), wherein said compound has a d90 particle size (i.e. the size of which 90% of the particles are smaller than or equal to) of less than about 50 μm.

A more particular embodiment comprises a compound of Formula I having a d90 particle size of less than about 10 μm.

As used herein the term "patient" refers to a human or nonhuman mammal such as a dog, cat, cow, monkey, horse, or sheep. More particularly, the term "patient" refers to a human. The term "treating" (or "treat" or "treatment") as used herein includes prohibiting, preventing, restraining, slowing, stopping, or reversing the progression or severity of an existing symptom or disorder. The term "preventing" (or "prevent" or "prevention") as used herein refers to prohibiting, restraining, or inhibiting the incidence or occurrence of a symptom or disorder. As appreciated by one of skill in the art, physiological disorders may present as a "chronic" condition, or as an "acute" episode. Thus, the treatment of disorders contemplates both acute events and chronic conditions. In an acute event, compound is administered at the onset of symptoms and discontinued when the symptoms disappear, whereas a chronic condition is treated throughout the course of the disease.

As used herein the term "effective amount" refers to the amount or dose of a compound of Formula (I) which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular compound administered; the mode of administration; the bioavailability characteristics of the preparation administered; the dose regimen selected; and the use of any concomitant medications.

When used in conjunction with the methods and uses of the present invention, the compounds and compositions of the present invention may be administered either alone, or in combination with conventional therapeutic agents used to treat the particular disorder or condition. Where the compounds or compositions of the present invention are used as part of a combination, the compound or composition comprising Formula (I) may be administered separately or as part of a formulation comprising the therapeutic agent with which it is to be combined.

As used herein, the designation "——" refers to a bond that protrudes forward out of the plane of the page, whereas the designation "••••••••" refers to a bond that protrudes backward out of the plane of the page.

PARTICULAR ASPECTS OF THE INVENTION

The following lists set out several groupings of particular configurations, substituents and variables for compounds of Formula (I). It will be understood that compounds of Formula (I) having such particular configurations, substituents or variables, as well as methods, uses, and compositions comprising such compounds, represent particular aspects of the present invention.

Thus, a particular aspect of the present invention is one wherein the compound of Formula (I) is one wherein L, $R^3$ and $R^4$ have any of the values defined herein, and:
 (a) $R^1$ represents hydrogen and $R^2$ represents hydrogen or fluoro; or
 (b) $R^1$ represents fluoro and $R^2$ represents hydrogen or fluoro; or
 (c) $R^1$ represents hydrogen or fluoro and $R^2$ represents hydrogen; or
 (d) $R^1$ represents hydrogen or fluoro and $R^2$ represents fluoro; or (e) $R^1$ and $R^2$ each independently represent hydrogen.

Additional particular aspects of the present invention are those wherein the compound of Formula (I) is one wherein $R^1$, $R^2$, $R^3$, and $R^4$ have any of the values defined herein, and:

(a) L represents —CH(CH$_3$)—CH$_2$— or a direct bond; or (b) L represents —CH(CH$_3$)—CH$_2$—; or (c) L represents a direct bond.

Additional particular aspects of the present invention are those wherein the compound of Formula (I) is one wherein $R^1$, $R^2$, L and $R^4$ have any of the values defined herein, and:

(a) $R^3$ represents hydrogen or a group of the formula

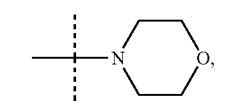 (a)

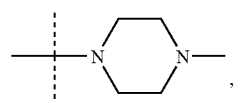 (b)

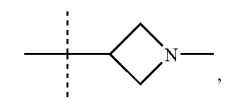 (c)

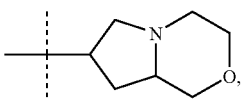 (d)

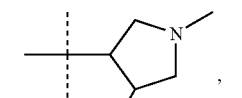 (e)

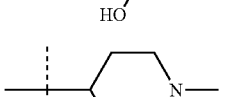 , or (f)

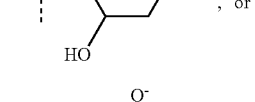 ; or (g)

(b) $R^3$ represents a group of the formula

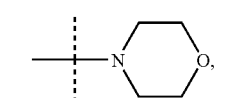 (a)

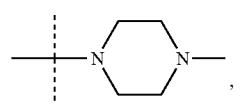 (b)

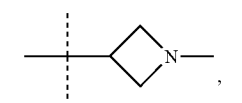 (c)

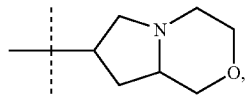 (d)

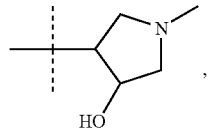 (e)

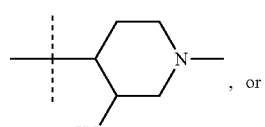 , or (f)

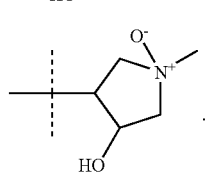 . (g)

Further particular aspects of the present invention are those wherein the compound of Formula (I) is one wherein $R^1$, $R^2$, L and $R^4$ have any of the values defined herein, and:

(a) $R^3$ represents hydrogen or a group of the formula

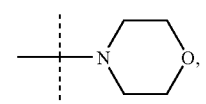 (a)

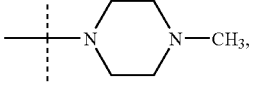 (b)

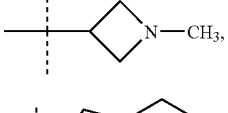 (c)

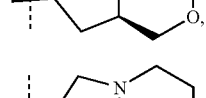 (d)

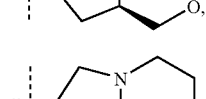 (e)

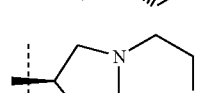 (f)

(g)

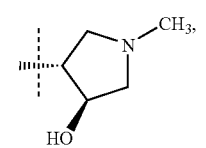 (h)

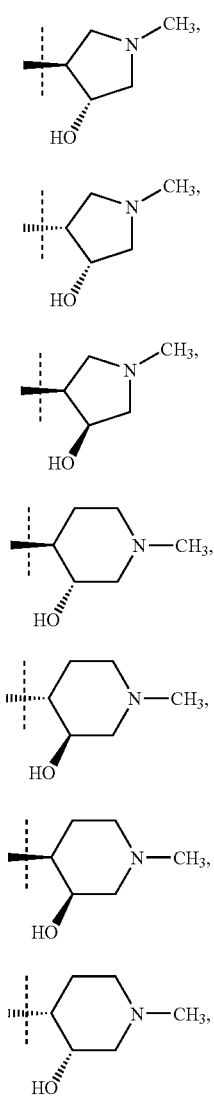
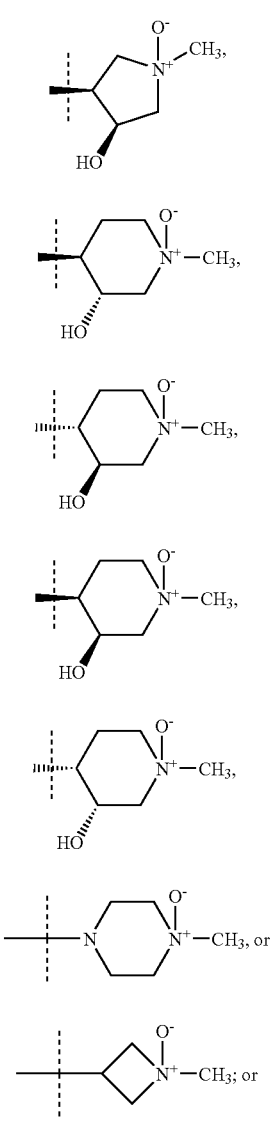
(b) R³ represents a group of the formula
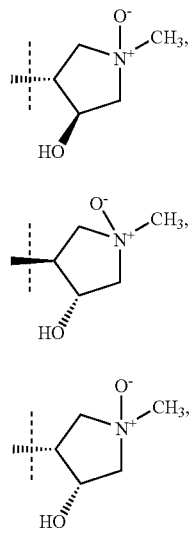

11

-continued

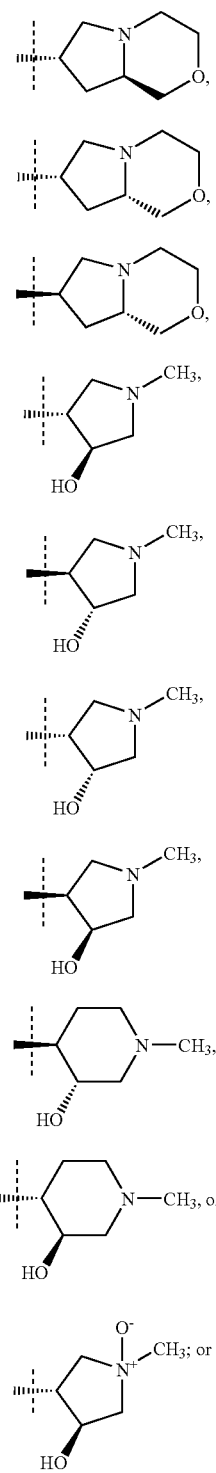

(e)

(f)

(g)

(h)

(i)

(j)

(k)

(l)

(m)

(n)

(c) R³ represents a group of the formula

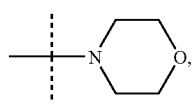

(a)

12

-continued

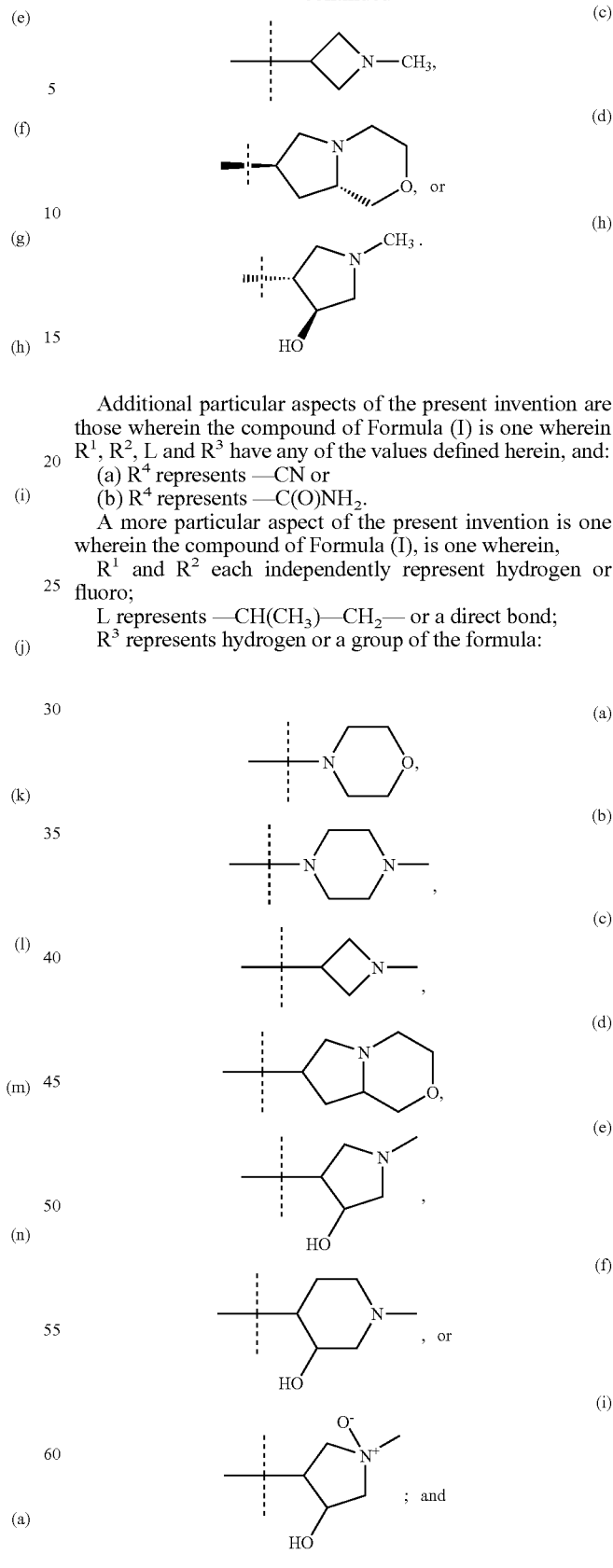

Additional particular aspects of the present invention are those wherein the compound of Formula (I) is one wherein R¹, R², L and R³ have any of the values defined herein, and:
(a) R⁴ represents —CN or
(b) R⁴ represents —C(O)NH₂.

A more particular aspect of the present invention is one wherein the compound of Formula (I), is one wherein, R¹ and R² each independently represent hydrogen or fluoro;

L represents —CH(CH₃)—CH₂— or a direct bond;

R³ represents hydrogen or a group of the formula:

R⁴ represents —CN or —C(O)NH₂, or a pharmaceutically acceptable salt thereof.

An even more particular aspect of the present invention is one wherein the compound of Formula (I) is one wherein, $R^1$ and $R^2$ each independently represent hydrogen or fluoro;

L represents —CH(CH$_3$)—CH$_2$— or a direct bond, provided that when L represents —CH(CH$_3$)—CH$_2$—, then $R^3$ represents a group of the formula:

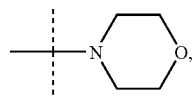

and when L represents a direct bond, then $R^3$ represents a group of the formula:

(a)

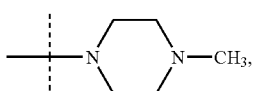

(b)

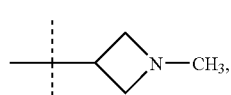

(c)

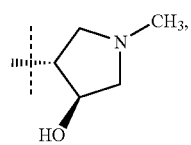

(d)

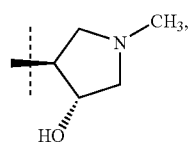

(e)

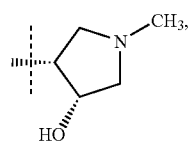

(f)

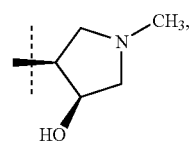

(g)

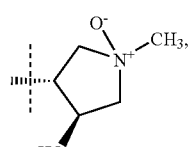

(h)

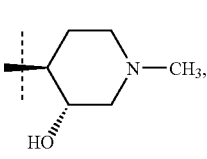

-continued (i)

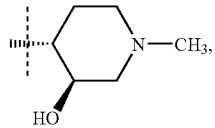

(j)

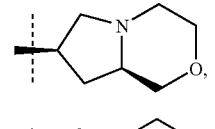

(k)

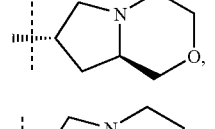

(l)

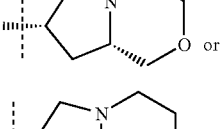

or (m)

; and $R^4$ represents —CN or —C(O)NH$_2$, or a pharmaceutically acceptable salt thereof.

Additional particular aspects of the present invention are provided by the compounds of Formula I(a) and Formula I(b) below. It will be understood that compounds of Formula I(a) and Formula I(b), as well as methods and uses employing such compounds, and compositions comprising such compounds represent particular further aspects of the present invention.

Thus, a particular aspect of the present invention is provided by a compound of Formula I(a):

Formula I(a)

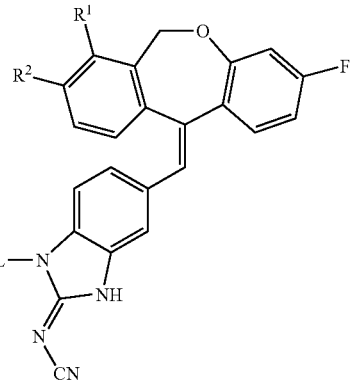

wherein, $R^1$ and $R^2$ each independently represent hydrogen or fluoro;

L represents —CH(CH$_3$)—CH$_2$— or a direct bond; and $R^3$ represents hydrogen or a group of the formula:

(a)

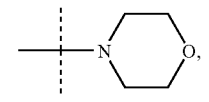

-continued

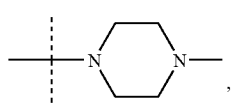 (b)

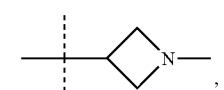 (c)

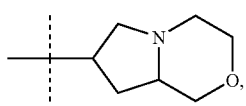 (d)

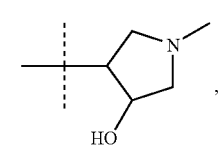 (e)

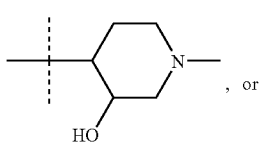 (f)

, or

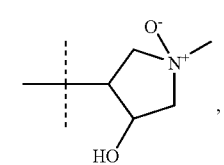 (i)

or a pharmaceutically acceptable salt thereof.

An even more particular aspect of the present invention is a compound of Formula I(a), wherein R$^1$ and R$^2$ each independently represent hydrogen or fluoro; and L represents —CH(CH$_3$)—CH$_2$— or a direct bond, provided that when L represents —CH(CH$_3$)—CH$_2$—, then R$^3$ represents a group of the formula:

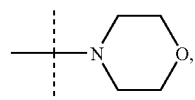

and when L represents a direct bond, then R$^3$ represents a group of the formula:

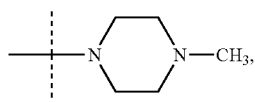 (a)

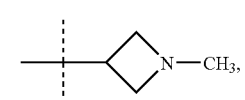 (b)

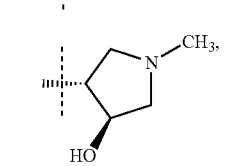 (c)

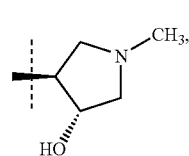 (d)

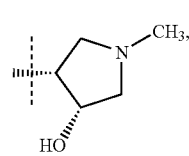 (e)

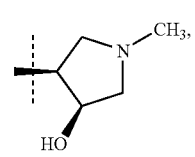 (f)

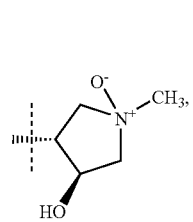 (g)

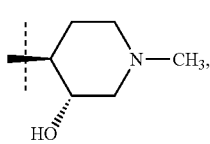 (h)

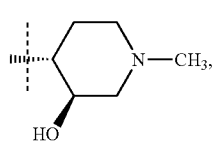 (i)

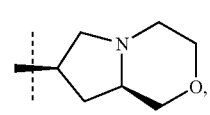 (j)

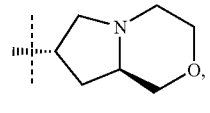 (k)

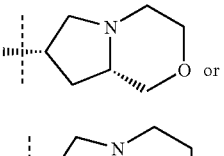 (l)

or

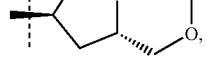 (m)

or a pharmaceutically acceptable salt thereof.

Yet another particular aspect of the present invention is provided by a compound of Formula I(b):

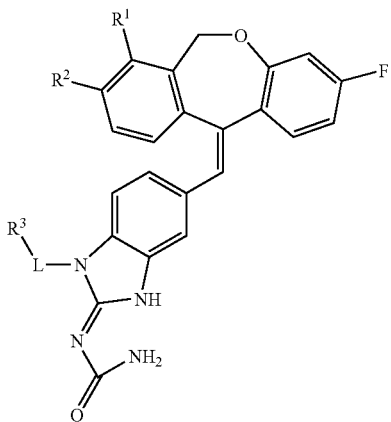

Formula I(b)

wherein,
R¹ and R² each independently represent hydrogen or fluoro;
L represents —CH(CH₃)—CH₂— or a direct bond; and
R³ represents a group of the formula:

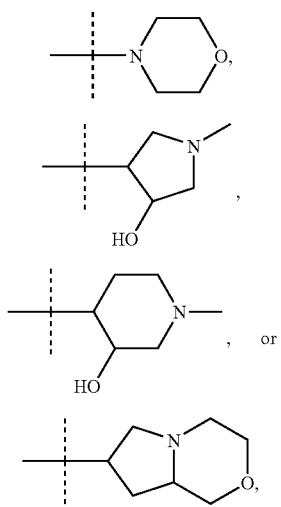

or a pharmaceutically acceptable salt thereof.

An even more particular aspect of the present invention is a compound of Formula I(b), wherein
R¹ and R² each independently represent hydrogen or fluoro; and
L represents —CH(CH₃)—CH₂— or a direct bond, provided that when L represents —CH(CH₃)—CH₂—, then R³ represents a group of the formula:

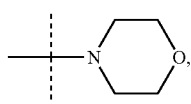

and when L represents a direct bond, then R³ represents a group of the formula:

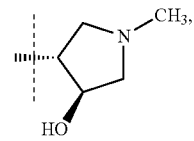

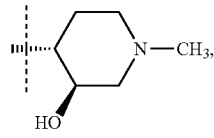

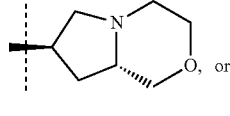

or a pharmaceutically acceptable salt thereof.

In addition, a most particular aspect of the present invention is provided by those compounds of Formula (I) exemplified herein, most particularly (E)-N-(5-((E)-3-Fluoro-6H-dibenzo[b,e]oxepin-11-ylidenemethyl)-1-(1-methyl-azetidin-3-yl)-1,3-dihydro-benzoimidazol-2-ylidene)-cyanamide; (E)-N-(5-((E)-(3-fluorodibenzo[b,e]oxepin-11 (6H)-ylidene)methyl)-1-((3S,4S)-4-hydroxy-1-methylpyrrolidin-3-yl)-1H-benzo[d]imidazol-2(3H)-ylidene)cyanamide; (E)-N-(5-((E)-(3-fluorodibenzo[b,e] oxepin-11(6H)-ylidene)methyl)-1-((3S,4S)-4-hydroxy-1-methylpyrrolidin-3-yl)-1H-benzo[d]imidazol-2(3H)-ylidene)cyanamide maleate; (E)-N-[5-((E)-3-Fluoro-6H-dibenzo[b,e]oxepin-11-ylidenemethyl)-1-((3S,4S)-4-hydroxy-1-methyl-pyrrolidin-3-yl)-1,3-dihydro-benzoimidazol-2-ylidene]-urea; (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea; or (E)-N-(5-((E)-3-Fluoro-6H-dibenzo[b,e] oxepin-11-ylidenemethyl)-1-((7S,8aR)-hexahydro-pyrrolo [2,1-c][1,4]oxazin-7-yl)-1,3-dihydro-benzoimidazol-2-ylidene)-urea.

The compounds of formula (I) may be prepared by a variety of procedures known in the art as well as those described in the Schemes, Preparations, and Examples below. However, the following discussion is not intended to be limiting to the scope of the present invention in any way. For example, the specific synthetic steps for each of the routes described may be combined in different ways, or in conjunction with steps from different schemes, to prepare additional compounds of Formula (I). The products of each step in the schemes below can be recovered by conventional methods including extraction, evaporation, precipitation, chromatography, filtration, trituration, crystallization, and the like.

The substituents, unless otherwise indicated, are as previously defined. The reagents and starting materials are readily available to one of ordinary skill in the art. Other necessary reagents and starting materials may be made by procedures which are selected from standard techniques of organic and heterocyclic chemistry, techniques which are analogous to the syntheses of known structurally similar compounds, and the procedures described in the Preparations and Examples which follow, including any novel procedures.

As used herein, the following terms have the meanings indicated: "MeOH" refers to methanol; "EtOH" refers to ethanol; "EtOAc" refers to ethyl acetate; "DMF" refers to dimethylformamide; "DMSO" refers to dimethyl sulfoxide; "TFA" refers to trifluoroacetic acid; "THF" refers to tetrahydrofuran; "DEAD" refers to diethyl azodicarboxylate; "DIAD" refers to diisopropyl diazodicarboxylate; "NBS" refers to N-bromosuccinimide; "MCPBA" refers to m-chloroperoxybenzoic acid; "tBOC" or "boc" refers to tert-butoxycarbonyl; "rac" refers to racemic; "prep" refers to preparation; "ex" refers to example; and "HPLC" refers to high performance liquid chromatography.

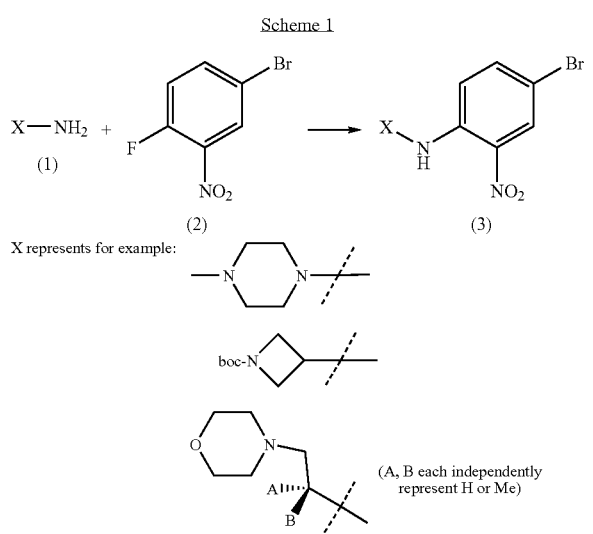

X represents for example:

Formation of an intermediate of formula (3) can be carried out in accordance with reactions as depicted in Scheme 1.

In Scheme 1, an amine of formula (1) is reacted with 4-bromo-1-fluoro-2-nitro-benzene in a nucleophilic aromatic substitution (SNAr) displacement to provide an amino-nitrophenyl bromide of formula (3). For example, the amine (1) can be reacted in an inert solvent such as ethyl acetate, THF or a protic solvent such as ethanol, at room temperature to the reflux temperature of the solvent.

It will be appreciated by the skilled artisan that compounds of formula (1) can be readily prepared by methods similar to those described herein or by using procedures that are established in the art. For example, a methyl substituted or unsubstituted morpholinyl ethylamine can be obtained by mesylation of a N-tert-butylcarboxyl ethanolamine and subsequently the mesylate displaced with morpholine to give the desired morpholinyl-ethylamine.

It will also be recognized that the selection and use of suitable protecting groups is well known and appreciated in the art (see for example, *Protecting Groups in Organic Synthesis*, Theodora Greene (Wiley-Interscience)). Amine functionality such as that present in the azetidinyl moiety, can be deprotected and subsequently further reacted to give additional compounds of the invention. For example, following deprotection of 3-(4-bromo-2-nitro-phenylamino)-azetidine-1-carboxylic acid tert-butyl ester under acidic conditions the azetidine can be alkylated in a reductive amination, such as with formaldehyde, to give the N-methyl azetidinyl intermediate.

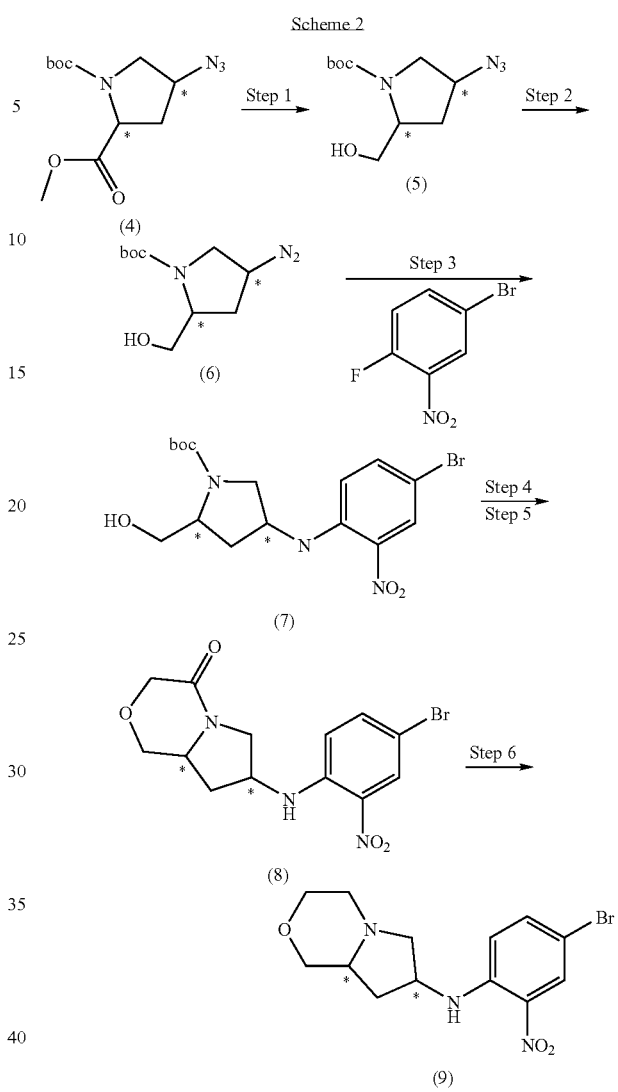

* = R or S chirality

Formation of an intermediate of formula (9) can be carried out in accordance with reactions as depicted in Scheme 2.

In Scheme 2, Step 1, an ester of formula (4) is reduced to an alcohol of formula (5). One skilled in the art will recognize that there are a number of methods for reducing esters. For example, the ester of formula (4) is treated with lithium borohydride at about 0 to 40° C. in an inert solvent, such as diethyl ether. Quenching of the reaction after 10 min allows isolation of the alcohol azide of formula (5) which is subsequently reduced to the amine in Step 2. The reduction of the azide can be performed using catalytic hydrogenation conditions common in the art to obtain the amino alcohol of formula (6).

In Scheme 2, Step 3, 4-bromo-1-fluoro-2-nitro-benzene undergoes a SNAr reaction with an amine of formula (6) as previously described for Scheme 1.

In Step 4, the phenyl-amino-pyrrolidine of formula (7) is deprotected using acidic conditions, such as hydrogen chloride or trifluoro acetic acid, and the product cyclized in Step 5 to an oxezinone of formula (8). The cyclization is achieved using chloroacetyl chloride in the presence of an inorganic base such as sodium hydroxide with the pH maintained between pH=10 to 12. The reaction is run in a mixture of THF and water (about 1:1).

In Scheme 2, Step 6, an oxezinone of formula (8) is reduced to an oxezine of formula (9). The carbonyl functionality is reduced using borane-tetrahydrofuran complex or borane-dimethylsulfide complex in an inert solvent, such as THF, at a temperature of about 0° C. to the reflux temperature of the solvent.

Chiral pyrrolidines of formula (4) are known in the art and can be readily prepared from stereo isomers of 3-hydroxyproline. The alcohol can be mesylated and then displaced with inversion of stereochemistry to the azide. Alternatively the alcohol can be converted to the bromide under Mitsinobu conditions using carbon tetrabromide with inversion of stereochemistry followed by subsequent displacement with azide ion to invert the stereochemistry again. Trans-hydroxyproline can be converted to the cis configuration by treatment with acetic acid and acetic anhydride at 90° C. (C. G. Levins and C. E. Schafmeister *J. Org. Chem.*, 2005, 70, 9002-9008).

Formation of an intermediate of formula (14a & b) or (17a & b) can be carried out in accordance with reactions as depicted in Scheme 3.

In Scheme 3, Step 1a, the racemic trans-hydroxy benzylamine pyrrolidine of formula (10) can be resolved using an appropriate enantiopure acid. For example, treatment with (+)-mandelic acid in an appropriate solvent such as acetonitrile with about 1% water, results in the selective recrystallization of the (S, S) hydroxy benzylamine (+) mandelate salt in very high diastereomeric excess. The salt can then be neutralized by utilizing an appropriate base, such as aqueous potassium carbonate. In Step 1b, the mother liquor from the above recrystallization, now enriched with the (R, R) enantiomer, can be evaporated and treated with (−) mandelic acid in a solvent such as acetonitrile containing about 2.5% water to obtain purified (R, R) enantiomer.

In Step 2, subjecting the free (S, S) or (R,R) hydroxy benzylamine to standard hydrogenation conditions using

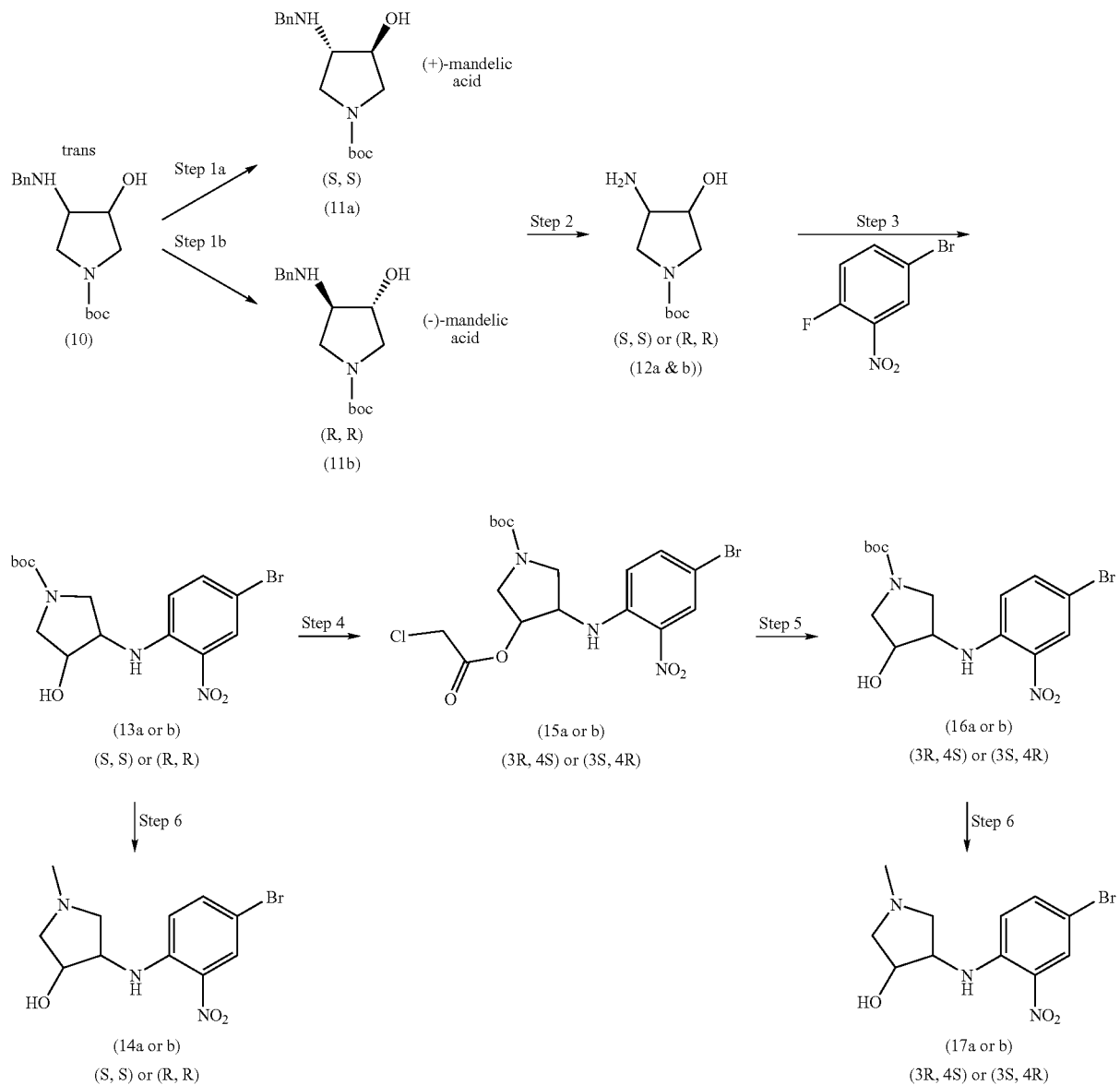

common catalysts, such as palladium on carbon, in a common solvent, such as methanol, n-butanol, or tetrahydrofuran, affords the corresponding (S, S) or (R, R) hydroxylamine.

In Scheme 3, Step 3, the SNAr reaction of the resulting aminopyrrolidine of formula (12a or b) with 4-bromo-1-fluoro-2-nitro-benzene provides a phenyl-aminopyrrolidine of formula (13a or b). The reaction can be carried out in the presence of an appropriate base such as triethylamine in a common solvent such as tetrahydrofuran or ethyl acetate.

In Scheme 3, Step 4, the chirality of the hydroxyl group of the pyrrolidine of formula (13a or b) is converted from (S, S) and (R, R) to (3R, 4S) and (3S, 4R) respectively. The chiral conversion is effected using a Mitsunobu reaction. The skilled artisan will recognize that there are various Mitsunobu conditions employed in the art. For example, the alcohol of formula (15a or b) is dissolved in a suitable anhydrous solvent like THF, CH$_2$Cl$_2$, toluene, etc., and treated with a trialkyl- or triarylphosphine such as Me$_3$P, Bu$_3$P, or Ph$_3$P and a dialkylazo-dicarboxylate, such as DEAD or DIAD.

In Step 5, the 3S, 4R and 4S, 3R-chloroacetoxy ester of formula (15a or b) is hydrolyzed to the hydroxypyrrolidine of formula (16a or b). The hydrolysis is accomplished using an inorganic base, such as aqueous lithium hydroxide, in a solvent such as methanol, at 0 to 50° C. for 4 to 24 h.

In Scheme 3, Step 6, the four diastereomeric aminopyrrolidines of formula (13a or b) and formula (16a or b) are deprotected using acidic conditions. The deprotection of tert-butoxycarbonyl groups is well-known in the art. Preferred conditions use an inert solvent, such as ethyl acetate treated with anhydrous hydrogen chloride gas at about 0° C. for 10 min. The resulting NH-pyrrolidine is subjected to reductive amination conditions to obtain an N-methylpyrrolidine of formula (14a or b) and formula (17a or b). The reaction is preformed in an inert solvent, such as dichloromethane, THF, or preferably acetonitrile and treated with aqueous formaldehyde. The reaction is treated with a reducing agent, such as sodium borohydride, sodium cyanoborohydride, or preferably sodium triacetoxy borohydride at about 0 to 40° C. for 4 to 24 hours.

It will be appreciated by the skilled artisan that compounds of formula (10) can be readily prepared by methods similar to those described herein or by using procedures that are established in the art. For example, 3-pyrroline can be protected with di-tert-butyl dicarbonate and subsequently brominated in DMSO/water to provide the trans-3-bromo-4-hydroxypyrrolidine (A. Kamal et. al. *Tetrahedron Lett.*, 2004, 45, 8057-8059; A. Kamal et. al. *Tetrahedron Asymmetry*, 2006, 17, 2876-2883). Reaction with sodium hydroxide forms the epoxide in situ which is reacted with benzylamine to provide the racemic trans-hydroxy benzylamine pyrrolidine of formula (10). In a more direct manner, the epoxide can be formed directly and isolated by oxidation of 3-pyrroline with MCPBA. In yet another synthetic alternative 2,4-dichloro-2-butene can be reacted with tert-butyl carbamate to generate 1-Boc-3-pyrroline (Y. Tsuzuki, et. al. *Tetrahedron Asymmetry*, 2001, 12, 2989-2997). The t-Boc protecting group can be avoided altogether by doing the reaction with methylamine in place of tert-butyl carbamate. Subsequent oxidation to the epoxide with MCPBA and opening with ammonia gives racemic trans-4-amino-1-methyl-pyrrolidin-3-ol. This can be reacted with 1-bromo-4-fluoro-3-nitrobenzene to give a compound of formula (14a & b) as a mixture of enantiomers. Resolution of this enantiomeric mixture can be accomplished by methods known in the art such as chiral HPLC or recrystallization with a salt of an enantiomerically pure carboxylic acid, such as with D-(−) or L-(+)-tartaric acid and the like.

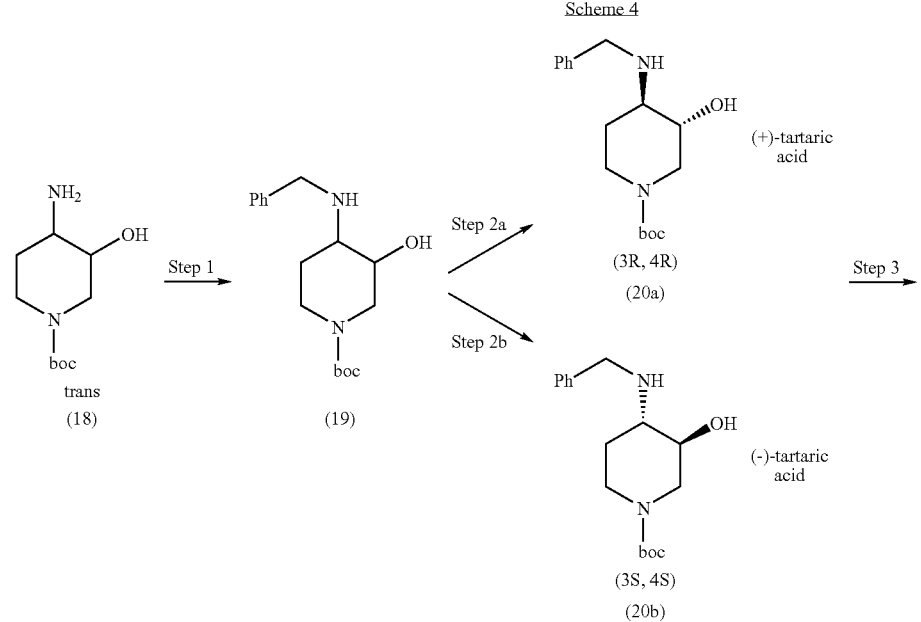

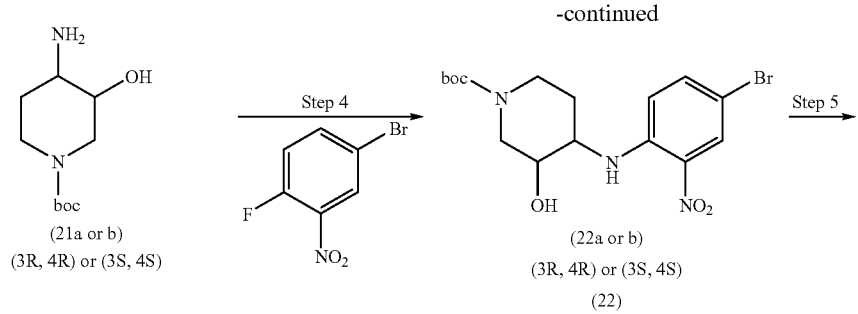

In Scheme 4, Step 1, a trans amino-hydroxy-piperidine of formula (18) undergoes reductive amination with benzaldehyde to provide a benzylamino piperidine of formula (19). The skilled artisan will recognize that there are various conditions which are suitable to achieve a reductive amination. For example, the reaction proceeds in a solvent such as ethanol, in the presence of acetic acid and a reducing agent, such as sodium cyanoborohydride.

In Scheme 4, Step 2a, the racemic trans-hydroxy benzylamine piperidine of formula (19) is resolved using an appropriate enantiopure acid. For example, treatment with (+)-tartaric acid in an appropriate solvent such as acetonitrile with about 5% water, results in the selective recrystallization of the (3R,4R)hydroxy benzylamine (+) tartarate salt of formula (20a) in very high diastereomeric excess. Similarly, in Step 2b, the racemic material is recrystallized with (−) tartaric acid in a solvent such as acetonitrile containing about 2.5% water to obtain purified (S, S) enantiomer of formula (20b).

In Step 3, the resolved 3R, 4R and 3S, 4S enantiomers of formula (20a) and (20b) respectively, can be debenzylated by catalytic hydrogenation to the aminohydroxy piperidine of formula (21a or b). Initially the tartrate salt is washed with a solution of sodium or potassium carbonate, followed by extraction with dichloromethane to remove the tartaric acid. The free benzylamine is then hydrogenated in an inert solvent such as ethanol or methanol using 5 or 10% palladium on carbon.

In Scheme 4, Step 4, the aminohydroxy piperidine of formula (21a or b) is converted to the phenyl-aminopiperidine of formula (22a or b) as in Scheme 3, Step 3.

In Step 5, the phenyl-aminopiperidine of formula (22a or b) is deprotected and alkylated by reductive amination to the N-methyl piperidine of formula (23a or b). The reaction proceeds in a solvent mixture of acetic acid and water in the presence of formaldehyde and a reducing agent, such as sodium cyanoborohydride.

4-Amino-3-hydroxy piperidines of formula (18) are known in the art and can be readily prepared from the 4-piperidone by reduction to the 4-hydroxy piperidine, protected with boc or other protecting group. The alcohol can be mesylated, eliminated to the olefin, and then epoxidized to provide racemic cis-7-oxa-3-aza-bicyclo[4.1.0]heptane-3-carboxylic acid tert-butyl ester. The epoxide is subsequently opened with azide anion to effect the trans regiochemistry, followed by reduction to obtain the amino hydroxyl piperidine of formula (18).

Scheme 5

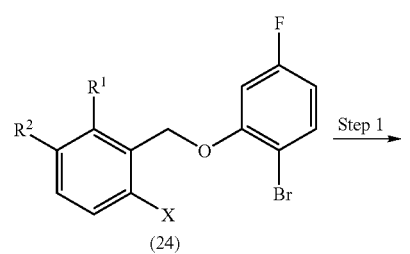

(24)

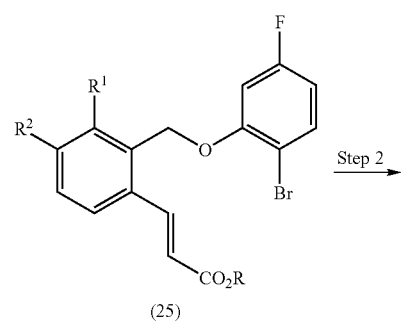

(25)

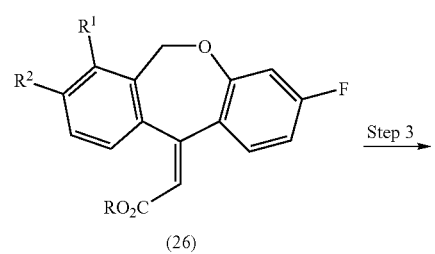

(26)

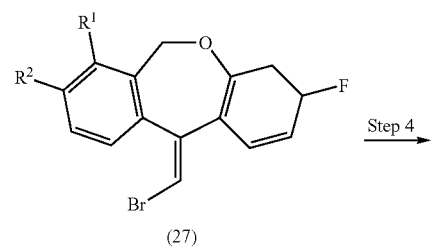

(27)

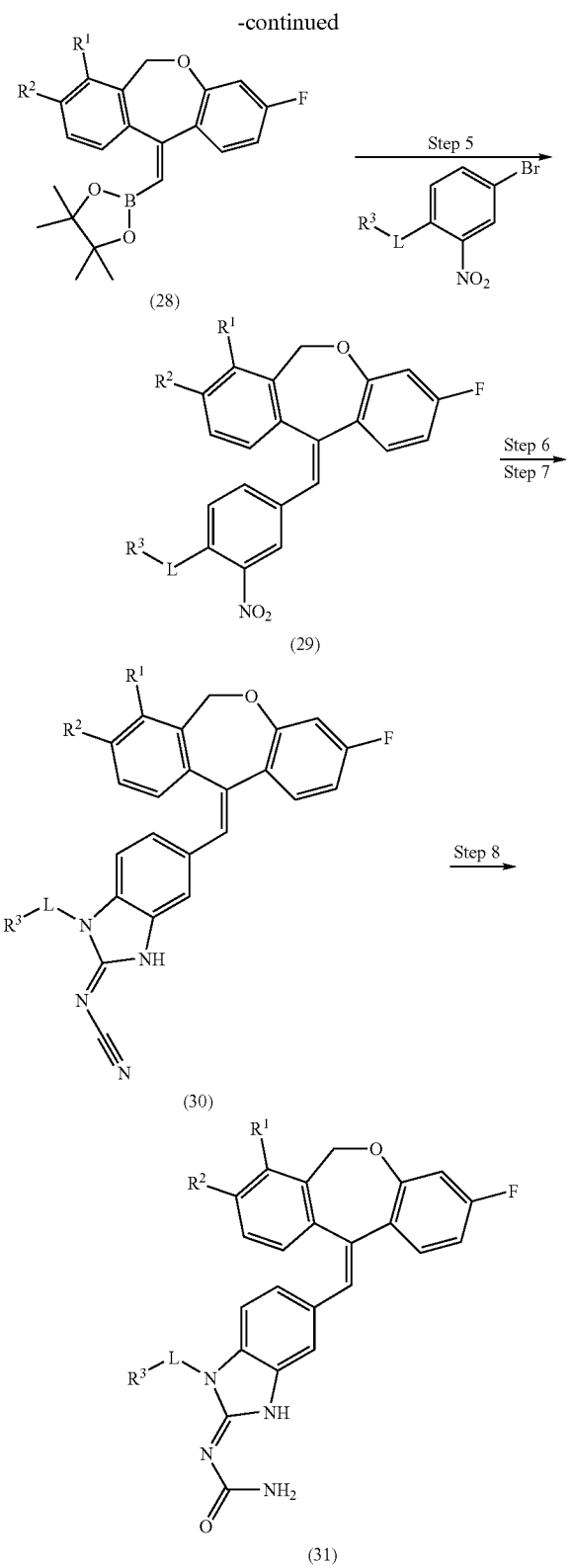

In Scheme 5, Step 1 and Step 2, a halobenzyl phenylether of formula (24) undergoes a double Heck coupling with methyl or ethyl acrylate to give a vinyl ester of formula (26) with E regiochemistry at the double bond. The reaction takes place in the presence of a palladium catalyst, such as tetrakis (triphenylphosphine)palladium (0), palladium chloride, or preferably, palladium (II) acetate. A base is included such as triethylamine, potassium carbonate, sodium acetate, or a quaternary ammonium salt, such as tetra-n-butylammonium bromide. The reaction proceeds in an inert solvent such as DMF or N-methylpyrrolidine at a temperature of about 40 to 130° C. for 4 to 48 h to give an intermediate of formula (25). It is isolated and subsequently cyclized to the vinyl ester of formula (26) under essentially similar reaction conditions at higher temperature, such as 90 to 150° C. Alternatively, the halobenzyl phenyl ether of formula (24) can be taken directly to the vinyl ester of formula (26) in one pot without isolation of the intermediate of formula (25) at a temperature of about 90 to 150° C.

In Step 3, the ester of formula (26) is hydrolyzed and converted to the vinyl bromide of formula (27). The hydrolysis can be accomplished using an inorganic base such as potassium, sodium, or preferably, lithium hydroxide. The resulting carboxylic acid can be subsequently treated with acetic acid and NBS at a temperature of 40 to 100° C.

In Scheme 5, Step 4, the vinyl bromide of formula (27) is converted to a vinyl pinacol boronate of formula (28). The vinyl bromide is reacted with bis(pinacolato)diboron in the presence of a base, such as cesium or potassium acetate, in an inert solvent such as THF, 1,2-dimethoxyethane, or preferably, 1,4-dioxane. The reaction is conducted at a temperature of about 40° C. to the refluxing temperature of the solvent, in the presence of a palladium catalyst, such as 1,1'-bis(diphenylphosphino)ferrocene palladium (II) dichloride (Pd$_2$(dppf)Cl$_2$), or alternatively tris(dibenzylideneacetone)dipalladium (0) (Pd$_2$(dba)$_3$) in the presence of a phosphine ligand, such as tricyclohexylphosphine.

In Step 5, the vinyl pinacol boronate of formula (28) is reacted with an aminonitrobromobenzene under Suzuki cross-coupling conditions to provide the vinylnitrophenyl intermediate of formula (29). The skilled artisan will recognize that there are a variety of conditions useful for facilitating such cross-coupling reactions. The reaction conditions make use of a suitable solvent such as dioxane/water or THF/methanol. The reaction is accomplished in the presence of a base such as sodium carbonate, sodium methoxide, potassium carbonate, or potassium acetate. The reaction takes place in the presence of a palladium catalyst, such as tetrakistriphenyl phosphine palladium (0) under an inert atmosphere at a temperature of about 70 to 120° C. for about 8 to 24 hours.

In Scheme 5, Steps 6 and 7, the vinylnitrophenyl intermediate of formula (29) is reduced to the diaminophenyl intermediate (not shown) under standard hydrogenation conditions with 5 or 10% platinum on carbon or 5 or 10% palladium on carbon in an appropriate solvent such as tetrahydrofuran, ethyl acetate, or isopropanol. After removal of the catalyst, the diaminophenyl intermediate can be converted into the cyanoguanidine of formula (30) utilizing diphenyl-N-cyanocarbonimidate at room temperature to 100° C. An inert solvent is used such as isopropanol, pyridine or THF, with or without an inorganic base, such as sodium bicarbonate. Purification of the final product can be achieved by methods common to those familiar with the art, such as chromatography or recrystallization.

In Scheme 5, Step 8, the cyanoguanidine of formula (30) is hydrolyzed to the urea of formula (31) under acidic condi- Formation of a compound of formula (30) or (31) can be carried out in accordance with reactions as depicted in Scheme 5. An appropriate compound of formula (24) is one in which R$^1$ and R$^2$ are as defined in Formula (I) and X=Br or I. Appropriate compounds of formula (30) or (31) are ones in which R$^1$, R$^2$, L, and R$^3$ are as defined for Formula (I).

tions. The reaction proceeds with 4 N hydrochloric acid in dioxane/water or in TFA/water for 4 to 72 h at room temperature to about 80° C.

It will be appreciated by the skilled artisan that compounds of formula (24) can be readily prepared by methods similar to those described herein or by using procedures that are established in the art. For example, 2-bromo-5-fluorophenol or 2-bromo-5-chlorophenol is alkylated with a 2-iodo or 2-bromobenzylbromide to give the phenylether of formula (24). Compounds of formula (24) wherein $R^1$ or $R^2$=F, the requisite benzylbromide is obtained by, for example, lithiation of 1-bromo-3-fluorobenzene and reaction with N-methyl-N-phenyl formamide to provide the aldehyde. Subsequent reduction to the benzyl alcohol and reaction, with a brominating agent, such as phosphorous tribromide gives 1-bromo-3-fluorobenzyl bromide.

Determination of Biological Activity:

As used herein, "$K_d$" refers to the equilibrium dissociation constant for a ligand-receptor complex; "$K_i$" refers to the equilibrium dissociation constant for drug-receptor complex, and is an indication of concentration of drug that will bind to half the binding sites at equilibrium; "$K_b$" refers to the equilibrium dissociation constant for an antagonist-receptor complex; "IC50" refers to the concentration of an agent which produces 50% of the maximal inhibitory response possible for that agent or, alternatively, to the concentration of an agent which produces 50% displacement of ligand binding to the receptor; "EC50" refers to the concentration of an agent which produces 50% of the maximal response possible for that agent; and "ED50" refers to the dose of an administered therapeutic agent which produces 50% of the maximal response for that agent.

Steroid Hormone Nuclear Receptor Binding Assay

Cell lysates from human embryonic kidney HEK293 cells overexpressing human MR (mineralocorticoid receptor), GR (glucocorticoid receptor), AR (androgen receptor), or PR (progesterone receptor) are used for receptor-ligand competition binding assays to determine $K_i$ values.

Briefly, steroid receptor competition binding assays are run in a buffer containing 20 mM HEPES buffer (pH=7.6), 0.2 mM EDTA, 75 mM NaCl, 1.5 mM $MgCl_2$, 20% glycerol, 20 mM sodium molybdate, 0.2 mM DTT (dithiothreitol), 20 μg/mL aprotinin and 20 μg/mL leupeptin (assay buffer). Typically, steroid receptor binding assays include radio-labeled ligands, such as 0.25 nM [$^3$H]-aldosterone for MR binding, 0.3 nM [$^3$H]-dexamethasone for GR binding, 0.36 nM [$^3$H]-methyltrienolone for AR binding, and 0.29 nM [$^3$H]-methyltrienolone for PR binding, and either 20 μg 293-MR lysate, 20 μg 293-GR lysate, 22 μg 293-AR lysate, or 40 μg 293-PR lysate per well. Assays are typically run in 96-well format. Competing test compounds are added at various concentrations ranging from about 0.01 nM to 10 μM. Non-specific binding is determined in the presence of 500 nM aldosterone for MR binding, 500 nM dexamethasone for GR binding, or 500 nM methyltrienolone for AR and PR binding. The binding reactions (140 μL) are incubated overnight at 4° C., then 70 μL of cold charcoal-dextran buffer (containing per 50 mL of assay buffer, 0.75 g of charcoal and 0.25 g of dextran) is added to each reaction. Plates are mixed for 8 minutes on an orbital shaker at 4° C. The plates are then centrifuged at 3,000 rpm at 4° C. for 10 minutes. An aliquot of 120 μL of the binding reaction mixture is then transferred to another 96-well plate and 175 μL of Wallac Optiphase Hisafe 3™ scintillation fluid is added to each well. Plates are sealed and shaken vigorously on an orbital shaker. After an incubation of 2 hours, plates are read in a Wallac Microbeta counter.

The data are used to calculate an estimated IC50 and percentage inhibition at 10 μM. The Kd for [$^3$H]-aldosterone for MR binding, [$^3$H]-dexamethasone for GR binding, [$^3$H]-methyltrienolone for AR binding, or [$^3$H]-methyltrienolone for PR binding, is determined by saturation binding. The IC50 values for compounds are converted to Ki using the Cheng-Prusoff equation.

Following a protocol essentially as described above, the compounds of Examples 1-50 display a $K_i$ in the MR binding assay of ≦10 nM. Preferably, compounds of the present invention display a $K_i$ in the MR binding assay of ≦5 nM, and more preferably ≦1 nM. Specifically, the compounds of Examples 1, 8, and 23 displayed a Ki in the MR binding assay of about 0.79 nM, 0.08 nM, and 0.23 nM respectively (values reported as geometric mean of n=2), thus demonstrating that compounds within the scope of the present invention are potent ligands of human MR.

Functional Assays of Steroid Nuclear Hormone Receptor Modulation:

Aldosterone exerts it physiological effects through interaction with the mineralocorticoid receptor. Following cytoplasmic binding of aldosterone to MR, the ligand receptor complex translocates to the cell nucleus where it binds to hormone response elements on DNA to initiate expression of target genes. To demonstrate the ability of compounds of the present invention to modulate the activity of steroid hormone receptors (i.e. either agonize, partially agonize, partially antagonize, or antagonize), bioassays are performed which detect functional modulation of target gene expression in cells transiently transfected with a nuclear receptor protein and a hormone response element-reporter gene construct. The solvents, reagents, and ligands employed in the functional assay are readily available from commercial sources, or can be prepared by one of ordinary skill in the art.

A. Nuclear Hormone Receptor Panel Screen

Human embryonic kidney HEK293 cells are transfected with steroid hormone receptor and reporter gene plasmids using a suitable transfection reagent such as Fugene™. Briefly, the reporter plasmid containing two copies of probasin ARE and TK (thymidine kinase) promoter upstream of the luciferase reporter cDNA, is transfected into HEK293 cells with a plasmid constitutively expressing human androgen receptor (AR) using viral CMV (cytomegalovirus) promoter. The reporter plasmid containing two copies of GRE and TK promoter upstream of the luciferase reporter cDNA is transfected with a plasmid constitutively expressing either human glucocorticoid receptor (GR), human mineralocorticoid receptor (MR), or human progesterone receptor (PR) using viral CMV promoter. Cells are transfected in T150 cm flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 hours and then exposed to various concentrations of test compounds ranging from about 0.01 nM to 10 μM. In the antagonist mode for the assays, low concentrations of agonist for each respective receptor are added to the media (0.08 nM aldosterone for MR, 0.25 nM dexamethasone for GR, 0.66 nM of methyltrienolone for AR, and 0.08 nM of promegestone for PR). After 24 hours incubation with test compounds, cells are lysed and luciferase activity is determined using standard techniques.

Data are fitted to a four parameter-fit logistic curve to determine EC50 values. The percentage efficacy (compounds with saturated maximum responses) or the percent maximum stimulation (compounds with maximum responses that do not saturate) are determined relative to maximum stimulation obtained with the following reference agonists: 30 nM aldosterone for MR assay, 100 nM methyltrienolone for AR assay, 30 nM promegestone for PR assay, and with 100 nM dexamethasone for GR assay. IC50 values are determined similarly using antagonist mode assay data. In the antagonist mode, percent inhibitions are determined by comparing test compound activity in the presence of low concentration of agonist (0.08 nM aldosterone for MR, 0.25 nM dexamethasone for GR, 0.66 nM of methyltrienolone for AR, and 0.08 nM of promegestone for PR) to the response produced by the same low concentration of agonist in the absence of test compound.

B. hMR Competitive Antagonist Assay

Human embryonic kidney HEK293 cells are transfected with human MR using the same transfection reagents, plasmids, promoters, reporter constructs, buffers, and procedures as described above for the Nuclear Hormone Receptor Panel Screen. Transfected cells are trypsinized, plated in 96 well dishes in DMEM media containing 5% charcoal-stripped FBS, incubated for 4 hours and then exposed to various concentrations (10 dilutions) of aldosterone (ranging from about 0.001 nM to 0.03 µM. The ability of aldosterone to agonize the hMR is determined in the absence and presence of fixed concentrations of test compound and is monitored by measuring luciferase activity using standard techniques. The test compound $K_b$ may then be determined using a Schild analysis plotting log(dose ratio−1) against log of antagonist concentration using the equation: Log(DR−1)=Log [Antagonist]−Log Kb where the dose ratio (DR) represents the ratio of the aldosterone EC50 in the presence of test compound to the aldosterone EC50 in the absence of test compound).

Following a protocol essentially as described above, the exemplified compounds of the present invention display a $K_b$ in the MR competitive antagonist assay of $\leq$200 nM. Preferably, compounds of the present invention display a $K_b$ in the MR competitive antagonist assay of $\leq$50 nM, and more preferably $\leq$10 nM. Specifically, the compounds of Examples 1, 8, and 23 displayed a $K_b$ in the MR competitive antagonist assay of about 1.2 nM, 1.1 nM, and 2.5 nM respectively (values reported as geometric mean of n=2), thus demonstrating that compounds within the scope of the present invention are potent antagonists of human MR.

In Vivo Model of Aldosterone Mediated Renal Disease

Male uni-nephrectomized Sprague Dawley rats (240-280 g) are housed individually with ad lib house water and rodent 5001 diet for one week. After acclimation, baseline 24 h urine samples are collected and analyzed for total urine protein and creatinine. Animals are randomized via body weight and baseline urine protein into study groups. Baseline serum is taken by tail-clip and analyzed for blood urea nitrogen (BUN), creatinine, and electrolytes. After baseline samples are taken, all rats with the exception of the control group are maintained on a diet containing 6% salt, and drinking water containing 0.3% KCl throughout the study duration. Control animals are maintained on 5001 diet and house water throughout the study duration and do not receive aldosterone. Alza mini-pumps to deliver 2.5 µl/h×28 days of d-aldosterone in 0.01% DMSO at 0.75 µg/h, s.c. are implanted in non-control animals (e.g Test Compound group and Vehicle only group) under isoflourane anesthesia. Test compound, in a vehicle comprising 1% carboxy methylcellulose (CMC)/ 0.25% polysorbate 80, or vehicle alone, is then administered by once daily oral gavage (10 mL/kg) beginning the day after aldosterone implantation. Repeat urine samples are collected after 2 and 4 weeks of compound or vehicle alone administration and analyzed for total urine protein and creatinine. At study termination, pharmacokinetic samples are obtained at 8 timepoints (0.5, 1, 2, 3, 6, 8, 12 and 24 h). In addition, hearts and kidneys are removed and fixed in 10% buffered formalin for haematoxylin and eosin (H&E) and Masson's trichrome staining to detect structural damage in cardiac and renal tissues. Serum is taken by cardiac puncture at study termination for additional analysis of serum BUN, creatinine, and electrolytes.

Following a protocol essentially as described above, the compounds of Examples 1, 8, and 23, when administered at 10 mg/kg/day×14 days, reduced uninary protein excretion compared to vehicle treated animals by about 49, 83, and 64 mg/day respectively (values represent an average of n=8 for each compound), thus demonstrating that compounds within the scope of the present invention have potent in vivo renoprotective activity.

In order to demonstrate that a compound has a reduced incidence or likelihood of producing hyperkalemia, the following model may be employed.

In Vivo Assay of Electrolyte Modulation

Male Sprague Dawley rats (240-280 g) are adrenalectomized then maintained on 5001 rodent chow and 1% NaCl drinking solution for 6 days after surgery. Animals are then fasted overnight and 1% saline drinking water is replaced with house water ad lib. The morning of the study, fasted animals are randomized to treatment on the basis of fasted body weight. Control animals (e.g. those that receive no aldosterone or test compound) are given 10 mL/kg of test compound vehicle comprising 0.5% CMC/0.25% polysorbate 80/2.7% NaCl by oral gavage, and 1 mL/kg of aldosterone vehicle (0.01% DMSO/water) by subcutaneous injection. Vehicle animals are given the same test compound vehicle by oral gavage and aldosterone 3 µg/kg, s.c. Test substances are suspended in the carboxy methylcellulose/NaCl vehicle. The test compound treatment groups receive test substance suspended in the carboxy methylcellulose/NaCl vehicle and aldosterone 3 µg/kg s.c. Immediately after dosing, animals are placed in metabolic racks with ad lib access to house water. Urine samples are collected 5 hours after dose administration and electrolyte excretion is assayed. Data are presented as log Na/K excretion ratio. Compounds can be tested at various doses to determine whether the compound induces an increase in the urinary Na/K ratio (an index of increased serum potassium concentration).

Without further elaboration, it is believed that one skilled in the art can use the preceding description to practice the present invention to its fullest extent. The following Preparations and Examples are provided to illustrate the invention in further detail and represent typical synthesis of the compounds of Formula (I). However, they are not intended to limit the invention in any way whatsoever. The reagents and starting materials are readily available to, or may be readily synthesized by, one of ordinary skill in the art. Those skilled in the art will promptly recognize appropriate variations from the procedures described in the examples. The names of the compounds of the present invention are generally provided by ChemDraw Ultra® version 10.0.

PREPARATION 1

1-Bromo-4-fluoro-2-(2-iodo-benzyloxy)-benzene

Stir a mixture of 2-iodobenzyl bromide (0.29 mol, 90 g), 2-bromo-5-fluorophenol (0.29 mol, 57.9 g), and potassium carbonate (0.46 mol, 63 g) in N,N-dimethylformamide (750 mL) at room temperature for 16 h. Add water (1 L), stir the resulting mixture for one hour, filter off solids, rinse with water and dry in a vacuum oven (20 mm Hg/60° C.) to obtain the title compound (121 g, >100%). $^1$H NMR (400 MHz, DMSO-d$_6$) δ 5.11 (s, 2H), 6.81 (t, 1H), 7.13 (t, 1H), 7.19 (dd, 1H), 7.46 (t, 1H), 7.59 (d, 1H), 7.62 (t, 1H), 7.93 (d, 1H).

PREPARATION 2

3-[2-(2-Bromo-5-fluoro-phenoxymethyl)-phenyl]-acrylic acid ethyl ester

To a mixture of 1-bromo-4-fluoro-2-(2-iodo-benzyloxy)-benzene (0.29 mol, 117.4 g), sodium acetate (0.44 mol, 36.1 g, 1.5 equiv.), tetra-n-butylammonium bromide (0.29 mol, 90.3 g), palladium (II) acetate (8 mmol, 1.8 g, 3 mol %), and N-methylpyrrolidinone (900 mL) at 55-60° C., add drop wise a solution of ethyl acrylate (0.32 mol, 34.3 mL) in N-methylpyrrolidinone (200 mL). Cool the reaction mixture to room temperature and treat with water (2 L) and methyl tert-butyl ether (2 L). Pass through diatomaceous earth, add ethyl acetate (1 L), separate the layers, and wash with water (2 L). Dry the organic portion over anhydrous sodium sulfate, filter, and concentrate. Suspend the resulting solid in hexanes (1 L), refrigerate for 2 h, filter, and wash with cold hexanes (500 mL). Dry in a vacuum oven (50° C./20 mm Hg) to obtain the title compound as a pale yellow solid (104.4 g, 95%). LC-MS m/z 381.0 [M+H]$^+$.

PREPARATION 3

(E)-(3-Fluoro-6H-dibenzo[b,e]oxepin-11-ylidene)-acetic acid ethyl ester

Heat a mixture of 3-[2-(2-bromo-5-fluoro-phenoxymethyl)-phenyl]-acrylic acid ethyl ester (0.25 mol, 94 g), sodium acetate (0.37 mol, 30 g, 1.5 equiv.), tetra-n-butylammonium bromide (0.25 mol, 81 g), and palladium (II) acetate (7 mmol, 1.7 g, 3 mol %) in N-methylpyrrolidinone (850 mL) at 100-110° C. for 6 h. Cool to room temperature, dilute with water (1 L), filter through diatomaceous earth, and wash with ethyl acetate (2 L). Transfer the filtrate to a separatory funnel, add water (500 mL) and separate the layers. Wash the organic layer with water (2×1.5 L), dry over anhydrous sodium sulfate, filter through a silica pad, wash with ethyl acetate (1.5 L) and concentrate to dryness. To the residual solid add hexanes (1 L), refrigerate for 2 h, filter, rinse with hexanes (500 mL), and dry at 50° C./20 mm Hg to obtain the title compound (64.3 g, 87%). LC-MS m/z 299.0 [M+H]$^+$.

PREPARATION 4

(E)-11-Bromomethylene-3-fluoro-6,11-dihydro-dibenzo[b,e]oxepine

To a suspension of (3-fluoro-6H-dibenzo[b,e]oxepin-11-ylidene)-acetic acid ethyl ester (0.23 mol, 69.5 g) in isopropanol (725 mL) add a solution of lithium hydroxide (0.53 mol, 12.0 g) in water (125 mL) and warm to 70° C. for 4 h. Allow the mixture to cool to 40° C. and then treat with glacial acetic acid (0.44 mol, 25 mL). After stirring for 15 min, add N-bromosuccinimide (0.25 mol, 44 g). Bubbling ensues, the temperature rises to 45° C., and solids form after a few min. Stir the mixture at 40-45° C. for one hour and cool to room temperature. Add sodium bisulfite (4.5 g) in water (150 mL), saturated aqueous sodium bicarbonate (150 mL), and water (450 mL). Filter the resulting suspension and rinse with cold 1:1 isopropanol/water (300 mL). Dry the solid at 60° C./20 mm Hg overnight to obtain the title compound (65.8 g, 93%).

$^1$H NMR (400 MHz, DMSO-d$_6$) δ 4.9-5.4 (br d, 2H), 6.63 (dd, 1H), 6.77 (dt, 1H), 7.13 (s, 1H), 7.32-7.46 (m, 4H), 7.52 (dd, 1H).

PREPARATION 5

(E)-2-((3-fluorodibenzo[b,e]oxepin-11(6H)-ylidene)methyl)-4,4,5,5-tetramethyl-1,3,2-dioxaborolane

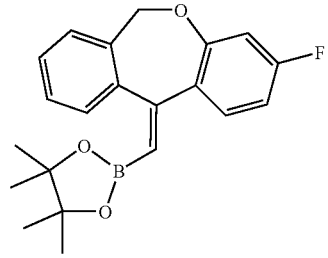

To a stirred mixture of (E)-11-(bromomethylene)-3-fluoro-6,11-dihydrodibenzo[b,e]oxepine (49 mmol, 15 g) and bis(pinacolato)diboron (64 mmol, 16 g) in 1,4-dioxane (250 mL) add potassium acetate (150 mmol, 15 g). Flush the mixture with nitrogen, add dichloro[1,1'-bis(diphenylphosphino)-ferrocene]palladium(II) dichloromethane adduct (2.46 mmol, 1.80 g), and heat at 65° C. overnight. Cool to room temperature, filter through diatomaceous earth, wash with ethyl acetate and concentrate the filtrate in vacuo. Add methanol (200 mL) and rotate the mixture for one hour on a rotory evaporator without vacuum causing a brown solid to form. Collect the dark brown crystals by filtration and dry under vacuum overnight to obtain the title compound (7.28 g, 42%). Concentrate the filtrate and purify by column chromatography eluting with 0% to 16% ethyl acetate in hexanes to obtain the title compound as a yellow solid (3.46 g, 20%). Total yield for the reaction is 10.7 g (62%). $^1$H NMR (300 MHz, CDCl$_3$) δ 7.36 (dd, J=8.8, 6.8 Hz, 1H), 7.32-7.27 (m, 4H), 6.64-6.57 (m, 1H), 6.48 (dd, J=10.3, 2.6 Hz, 1H), 5.98 (s, 1H), 5.20 (br s, 1H), 1.15 (s, 12H).

PREPARATION 6

1-Bromo-3-fluorobenzaldehyde

To a solution of diisopropylamine (2.27 mol, 320 mL) in anhydrous tetrahydrofuran (800 mL) in a 5 L flask at 0° C. add 1.6 M butyllithium (1.16 L, 1.86 mol) in hexanes dropwise over 1.5 h. Stir the resulting yellow solution at 0° C. for 30 min. In a separate 12 L flask dissolve 1-bromo-3-fluorobenzene (203 mL, 1.86 mol) in anhydrous tetrahydrofuran (650 mL) and cool to −78° C. Transfer the preformed LDA solution to an addition funnel via cannula and add dropwise to the 1-bromo-3-fluorobenzene solution over 2 h so the temperature does not rise above −70° C. Stir the resulting slurry at −78° C. for 30 min. Add a solution of N-methyl-N-phenyl formamide (230 mL, 1.86 moles, 1.00 equiv.) in anhydrous tetrahydrofuran (1.15 L) dropwise at −78° C. over one hour while maintaining the temperature below −70° C. Stir the reaction cold for 2 h while slowly allowing it to rise to room temperature overnight. Dilute the reaction with methyl tert-butyl ether (3 L), quench with 1M hydrochloric acid (4 L) and stir vigorously for 3 h. Separate the layers and extract the aqueous layer with methyl tert-butyl ether (1 L). Wash the combined organic phases with 1M hydrochloric acid (2×1 L), water (1 L), brine (1 L), dry over magnesium sulfate, filter and concentrate to an orange oil that slowly solidifies to obtain the title compound (394 g, 105%). $^1$H NMR (CDCl$_3$) δ 10.37 (s, 1H), 7.50 (d, 1H), 7.44 (m, 1H), 7.17 (t, 1H).

PREPARATION 7

1-Bromo-3-fluorobenzyl alcohol

To 1-bromo-3-fluorobenzaldehyde (1.60 kg, 7.91 mol) in methanol (14 L) at 0° C. add sodium borohydride (284 g, 7.93 mol) in portions over 30 min to control the exotherm and gas evolution. After 15 min, quench with water (500 mL) and concentrate to obtain a yellow oil. Dissolve the oil in ethyl acetate (6 L) and wash with water (3 L). Extract the aqueous layer with ethyl acetate (1 L). Wash the combined organic phases with brine (2 L), dry over sodium sulfate, filter, and concentrate to obtain the title compound as an orange oil (1614 g, 100%). $^1$H NMR (CDCl$_3$) δ 7.40 (d, 1H), 7.18 (m, 1H), 7.07 (t, 1H), 4.86 (s, 2H).

PREPARATION 8

1-Bromo-3-fluorobenzyl bromide

To a solution of 1-bromo-3-fluorobenzyl alcohol (1.61 kg, 7.85 mol) in chloroform (14 L) at 0° C. add pyridine (770 mL, 9.52 mol) in one portion (slight exotherm) and stir at 0° C. for 5 min. Add phosphorus tribromide (900 mL, 9.49) dropwise while maintaining the internal temperature below 20° C. and stir the resulting solution overnight while allowing to warm to room temperature. Cool the reaction to 0° C. and quench slowly with ice water (2 L). Transfer to a 50 L flask, separate the layers and then extract the aqueous layer with chloroform (1 L). Wash the combined organic phases with 5% sulfuric acid (2 L), saturated aqueous sodium bicarbonate (2 L), brine (2 L), dry over magnesium sulfate, filter, and concentrate to obtain the title compound as a yellow oil (1753 g, 83%). $^1$H NMR (CDCl$_3$) δ 7.43 (d, 1H), 7.21 (m, 1H), 7.09 (t, 1H), 4.68 (s, 2H).

PREPARATION 9

1-Bromo-2-(2-bromo-6-fluoro-benzyloxy)-4-fluoro-benzene

To a solution of 1-bromo-3-fluorobenzyl bromide (1.75 kg, 6.52 mol) and 2-bromo-5-fluorophenol (730 mL, 16.56 mol, 1.01 eq) in N,N-dimethylformamide (14 L) at 0° C. add potassium carbonate (1.36 kg, 9.80 mol) in one portion and stir the resulting slurry cold for one hour and then at room temperature overnight. Transfer the reaction mixture to a 50 liter flask, add water (14 L) drop wise over 30 min and ice periodically to control the exotherm of the crystallization. Stir at room temperature for one hour, collect off-white solids by filtration, wash with water, and dry overnight at 50° C. to obtain the title compound (2.22 kg, 90%). $^1$H NMR (CDCl$_3$) δ 7.51 (m, 2H), 7.30 (m, 1H), 7.14 (t, 1H), 6.89 (dd, 1H), 6.67 (m, 1H), 5.26 (d, 2H).

PREPARATION 10

(E)-(3,7-Difluoro-6H-dibenzo[b,e]oxepin-11-ylidene)-acetic acid ethyl ester Degas a mixture of 1-bromo-2-(2-bromo-6-fluoro-benzyloxy)-4-fluoro-benzene (886 mmol, 335 g), ethyl acrylate (931 mmol, 101 mL, 1.05 eq), Pd(OAc)$_2$ (22.2 mmol, 4.97 g), tetrabutylammonium bromide (886 mmol, 286 g), and sodium acetate (4.40 mol, 363.5 g) in N-methylpyrrolidinone (3.3 L) by evacuating and back-filling with nitrogen five times. Heat the mixture to 120° C. for 2 h. Cool to 35° C. and add water (5.5 L) over 40 min. Filter the precipitate, rinse with water (2×500 mL) and air dry for 30 min. Reslurry the in isopropanol (1 L) for 2 h and cool on ice for one hour. Collect the dark gray solid by filtration, rinse with cold isopropanol (5×100 mL) and dry at 50° C. in vacuo to obtain the title compound (191 g, 68%).

PREPARATION 11

(E)-11-Bromomethylene-3,7-difluoro-6,11-dihydro-dibenzo[b,e]oxepine

Heat a stirred slurry of (E)-(3,7-difluoro-6H-dibenzo[b,e] oxepin-11-ylidene)-acetic acid ethyl ester (601 mmol, 190 g) in methanol (1.9 L) and 5 N sodium hydroxide (1.20 mol, 240 mL) to 50° C. for 2 h. Remove the methanol in vacuo and reslurry the resulting black sludge in water (3 L). Add 5 N hydrochloride acid (250 mL) over 45 min, stir for 2.5 h, filter, and rinse the residue with water (4×200 mL). Dry the gray solid in vacuo at 60° C. overnight, and 80° C. for 6 h. Dissolve the solid (still wet, contains approximately 95 g of water) and lithium acetate (60.1 mmol, 4 g, 0.1 eq) in acetonitrile (1.7 L) and stir for 15 min. Add N-bromosuccinimide (661 mmol, 118 g) in one portion and stir for 2.5 h. Add 0.25 M sodium thiosulfate (400 mL), followed by saturated aqueous sodium bicarbonate (400 mL), and water (900 mL). Stir the mixture for one hour at room temperature and then stir for 2 h on an ice bath. Filter the mixture and rinse with cold acetonitrile (300 mL). Dry overnight in vacuo at 50° C. to obtain the title compound as a light beige solid (173.3 g, 89%). $^1$H NMR (DMSO-d$_6$) δ 5.25 (s, 2H), 6.67 (dd, 1H), 6.81 (dt, 1H), 7.20 (s, 1H), 7.22 (d, 1H), 7.28 (t, 1H), 7.36 (dd, 1H), 7.48 (m, 1H).

PREPARATION 12

(E)-2-((3,7-difluorodibenzo[b,e]oxepin-11(6H)-ylidene)methyl)-4,4,5,5-tetramethyl-1,3,2-dioxaborolane To a mixture of (E)-11-(bromomethylene)-3,7-difluoro-6, 11-dihydrodibenzo[b,e]oxepine (46.4 mmol, 15.0 g) and bis (pinacolato)diboron (50.3 mmol, 15.3 g) in 1,4-dioxane (150 mL) add potassium acetate (74.3 mmol, 7.29 g), tricyclohexyl phosphine (6.03 mmol, 1.69 g) and Pd$_2$(dba)$_3$ (2.32 mmol, 2.13 g). Flush by bubbling with nitrogen, then stir with heating at 65° C. overnight. After cooling to room temperature, filter the mixture through a pad of diatomaceous earth, wash the pad with ethyl acetate, and remove the solvent to obtain a brown oil. Dilute the oil with methanol (180 mL) and swirl the resulting mixture on a rotory evaporator without vacuum for 3 h causing a white precipitate to form. Collect the precipitate by vacuum filtration to obtain the title compound (10.8 g, 63%) as a white solid. $^1$H NMR (300 MHz, CDCl$_3$) δ 7.34 (dd, J=8.8, 6.7 Hz, 1H), 7.24-7.18 (m, 1H), 7.08-7.01 (m, 2H), 6.65-6.59 (m, 1H), 6.50 (dd, J=10.3, 2.6 Hz, 1H), 5.99 (s, 1H), 5.31 (d, J=0.9 Hz, 2H), 1.16 (s, 12H).

PREPARATION 13

(E)-11-Bromomethylene-3,8-difluoro-6,11-dihydro-dibenzo[b,e]oxepine

Prepare the title compound essentially as described in Preparations 9, 10 and 11, starting with 1-bromo-2-bromomethyl-4-fluoro-benzene and 2-bromo-5-fluoro-phenol.

PREPARATION 14

(E)-2-((3,8-difluorodibenzo[b,e]oxepin-11(6H)-ylidene)methyl)-4,4,5,5-tetramethyl-1,3,2-dioxaborolane To a mixture of (E)-11-(bromomethylene)-3,8-difluoro-6,11-dihydrodibenzo[b,e]oxepine (90.0 mmol, 29.0 g) and bis(pinacolato)diboron (117 mmol, 29.5 g) in 1,4-dioxane (295 mL), add potassium acetate (144 mmol, 14.1 g), tricyclohexyl phosphine (11.7 mmol, 3.28 g), and $Pd_2(dba)_3$ (4.14 mmol, 3.80 g). Flush by bubbling nitrogen through the mixture, then heat at 65° C. overnight. After cooling to room temperature, filter through a pad of diatomaceous earth and wash with ethyl acetate. Concentrate the filtrate in vacuo to obtain a brown oil. Dilute the oil with methanol (180 mL) and swirl the resulting mixture for 1.5 h on a rotory evaporator without vacuum, causing a brown precipitate to form. Collect the precipitate by vacuum filtration to obtain the title compound as a brown solid (24.2 g, 73%). $^1$H NMR (300 MHz, $CDCl_3$) δ 7.35 (dd, J=8.8, 6.7 Hz, 1H), 7.29-7.24 (m, 1H), 7.05-6.93 (m, 2H), 6.65-6.59 (m, 1H), 6.49 (dd, J=10.2, 2.6 Hz, 1H), 5.99 (s, 1H), 5.15 (br s, 2H), 1.16 (s, 12H).

PREPARATION 15

(R)-Methanesulfonic acid 2-tert-butoxycarbonylamino-propyl ester

Add methanesulfonyl chloride (0.128 mol, 14.7 g, 1.5 equiv.) drop wise to a solution of (R)-(+)-2-tert-butoxy-carbonylamino-1-propanol (0.085 mol, 15.0 g) and triethylamine (0.12 mol, 17.3 g, 2.0 equiv.) in dichloromethane (150 mL) at 0° C. under nitrogen. Upon complete addition, warm the reaction mixture to room temperature and stir for 2 h. Dilute the reaction mixture with dichloromethane, wash with 0.1 N hydrochloric acid and saturated sodium bicarbonate solution. Dry the organic layer over anhydrous sodium sulfate, filter, and concentrate under vacuum to obtain the title compound (20.8 g, 96%) as white solid. $^1$H NMR (400 MHz, $CDCl_3$) δ 1.24 (d, 3H), 1.43 (s, 9H), 3.03 (s, 3H), 3.97 (br s, 1H), 4.14 (dd, 1H), 4.21 (br s, 1H), 4.64 (br s, 1H, Boc-NH).

PREPARATION 16

(R)-(1-Methyl-2-morpholin-4-yl-ethyl)-carbamic acid tert-butyl ester

Heat a mixture of (R)-methanesulfonic acid 2-tert-butoxy-carbonylamino-propyl ester (0.083 mol, 20 g) and morpholine (0.83 mol, 72.2 g) in acetonitrile (210 mL) to 65° C. for 16 h. Concentrate the reaction mixture, dilute the residue with water, extract with dichloromethane, combine organic layer and wash with water. Dry the organic layer over anhydrous sodium sulfate, filter and concentrate under vacuum to obtain the title compound (12 g, 62%) as yellow thick oil. $^1$H NMR (400 MHz, $CDCl_3$) δ 1.13 (d, 3H), 1.43 (s, 9H), 2.21 (dd, 1H), 2.26-2.32 (m, 1H), 2.35-2.39 (m, 2H), 2.48-2.55 (m, 2H), 3.63-3.70 (m, 5H), 4.68 (br s, 1H, —NH).

PREPARATION 17

(R)-1-Methyl-2-morpholin-4-yl-ethylaminehydrochloride

Add 1.6 M hydrogen chloride in dioxane (120 mL) to a solution of (R)-(1-methyl-2-morpholin-4-yl-ethyl)-carbamic acid tert-butyl ester (0.05 mol, 12 g) in dry dichloromethane (75 mL) at 0° C. Warm the reaction mixture to room temperature and stir for 2 h. Filter the precipitate and dry under vacuum to obtain the title compound (9.2 g, 86%) as a white solid. $^1$H NMR (400 MHz, DMSO-$d_6$) δ 1.29 (d, 3H), 3.10 (br s, 2H), 3.38 (br s, 4H), 3.79 (br s, 5H).

PREPARATION 18

(R)-(4-Bromo-2-nitro-phenyl)-(1-methyl-2-morpholin-4-yl-ethyl)-amine

Reflux a mixture of (R)-1-methyl-2-morpholin-4-yl-ethylaminehydrochloride (0.04 mol, 8.7 g), 5-bromo-2-fluoronitrobenzene (0.048 mol, 10.5 g), triethylamine (0.20 mol, 20.2 g) and dimethylaminopyridine (0.0004 mol, 0.048 g) in ethyl acetate (220 mL) for 16 h. Cool the reaction mixture to room temperature, dilute with ethyl acetate, and wash with water and brine. Dry the organic layer over anhydrous sodium sulfate, filter, and concentrate. Purify on a silica gel column using 10% ethyl acetate in hexanes as eluent to obtain the title compound (12.8 g, 95%) as an orange solid. $^1$H NMR (400 MHz, $CDCl_3$) δ 1.29 (d, 3H), 2.47-2.51 (m, 5H), 2.53-2.58 (m, 1H), 3.64-3.69 (m, 4H), 3.72-3.78 (m, 1H), 6.78 (d, 1H), 7.46 (dd, 1H), 8.30 (d, 1H), 8.33 (d, 1H).

Prepare the intermediates in the table below by essentially following the procedures as described in Preparations 15, 16, 17, and 18 starting from (S)-(−)-2-tert-butoxy-carbonylamino-1-propanol or tert-butyl-N-(2-hydroxyethyl)carbamate respectively.

| Prep | Chemical Name | Physical Data |
|---|---|---|
| 19 | (S)-(4-Bromo-2-nitro-phenyl)-(1-methyl-2-morpholin-4-yl-ethyl)-amine | $^1$H NMR (400 MHz, $CDCl_3$) δ 1.29 (d, 3H), 2.46-2.58 (m, 6H), 3.63-3.69 (m, 4H), 3.71-3.79 (m, 1H), 6.77 (d, 1H), 7.45 (dd, 1H), 8.29 (d, 1H), 8.33 (d, 1H). |

PREPARATION 20

(4-Bromo-2-nitro-phenyl)-(4-methyl-piperazin-1-yl)-amine

Heat a mixture of 1-amino-4-methyl piperazine (0.217 mol, 25.0 g), 5-bromo-2-fluoronitrobenzene (0.239 mol, 52.6 g) and triethylamine (0.46 mol, 46 g) in ethyl acetate (900 mL) to reflux for 16 h. Cool the reaction mixture to room temperature, dilute with ethyl acetate, and wash with water and brine. Dry the organic layer over anhydrous sodium sulfate, filter, and concentrate. Purify on a silica gel column using 5% methanol in dichloromethane as eluent to give the title compound (43.2 g, 63%). ES-MS m/z 315 [M+1]$^+$.

PREPARATION 21

3-(4-Bromo-2-nitro-phenylamino)-azetidine-1-carboxylic acid tert-butyl ester

Dissolve 5-bromo-2-fluoronitrobenzene (28.8 mmol, 3.55 mL), 3-amino-azetidine-1-carboxylic acid tert-butyl ester (28.8 mmol, 4.96 g), and triethylamine (35.9 mmol, 5.00 mL) in ethyl acetate (100 mL) and reflux under nitrogen for 48 h. Cool to room temperature. Wash with 0.5 M hydrochloric acid twice, dry over anhydrous sodium sulfate, filter, and concentrate in vacuo to obtain a bright orange solid (11.04 g, >100%). LC-MS m/z ($^{79}$Br/$^{81}$Br) 394.0/396.0 [M+H]$^+$.

PREPARATION 22

Azetidin-3-yl-(4-bromo-2-nitro-phenyl)-amine, hydrochloride

Stir a solution of 3-(4-bromo-2-nitro-phenylamino)-azetidine-1-carboxylic acid tert-butyl ester (29.66 mmol, 11.04 g) in 4.0 M hydrogen chloride in dioxane (40 mL) at room temperature under nitrogen overnight. Solids crash out of solution. Dilute with ether (200 mL), filter off solids, rinse with ample ether and dry (8.54 g, 93%). $^1$H NMR (400 MHz, CD$_3$OD): 4.12 (dd, 2H), 4.45 (dd, 2H), 4.72 (m, 1H), 6.76 (d, 1H), 7.62 (dd, 1H), 8.30 (d, 1H). LC-MS m/z ($^{79}$Br/$^{81}$Br) 272.0/274.0 [M+H]$^+$.

PREPARATION 23

(4-Bromo-2-nitro-phenyl)-(1-methyl-azetidin-3-yl)-amine

To a mixture of azetidin-3-yl-(4-bromo-2-nitro-phenyl)-amine, hydrochloride (27.7 mmol, 8.54 g) in acetonitrile (100 mL) and 37% aqueous formaldehyde (83.0 mmol, 6.28 mL, 3.00 equiv.) at 0° C. add sodium triacetoxyborohydride (88.6 mmol, 18.8 g) slowly. Stir at room temperature under nitrogen overnight. Remove volatiles under reduced pressure. Dilute with ethyl acetate, wash with 10% aqueous sodium bicarbonate twice, dry over anhydrous sodium sulfate, filter, and concentrate under reduced pressure to obtain 8.5 g of an orange solid. Purify on a 120 g silica column eluting with 5% methanol in dichloromethane to obtain the title compound (5.92 g, 75%). LC-MS m/z ($^{79}$Br/$^{81}$Br) 286.0/288.0 [M+H]$^+$.

PREPARATION 24

(2S,4R)-4-Hydroxy-pyrrolidine-1,2-dicarboxylic acid 1-tert-butyl ester 2-methyl ester Add thionyl chloride (1.07 mol, 128.2 g) drop wise to a solution of (2S,4R)-4-hydroxy-pyrrolidine-2-carboxylic acid (0.70 mol, 93.0 g) in dry methanol (2 L) at 0° C. under a nitrogen atmosphere. Upon complete addition, warm the reaction mixture to room temperature and stir for 6 h. Concentrate the reaction mixture under reduced pressure to obtain the corresponding methyl ester hydrochloride. Add triethylamine (1.56 mol, 157.5 g) to a solution of methyl ester hydrochloride in dry dichloromethane (2 L) at 0° C. and stir for 30 min. Then add N,N-dimethylaminopyridine (0.10 mol, 13 g) and di-tert-butyl dicarbonate (0.85 mol, 185.7 g) consecutively. Warm the reaction mixture to room temperature and stir for 18 h. Quench the reaction mixture with water, separate the organic layer, and wash with water and saturated sodium bicarbonate solution. Dry the organic layer over anhydrous sodium sulfate, filter, and concentrate under reduced pressure to obtain the title compound (160 g, 91%) as viscous oil. ES-MS m/z 246.1 [M+1]$^+$.

PREPARATION 25

(2R,4R)-4-Hydroxy-pyrrolidine-2-carboxylic acid, hydrochloride

To a mixture of acetic anhydride (408 g) and acetic acid (1.2 L) at 50° C. add trans-4-hydroxy-L-proline (0.36 mol, 94 g) in a single portion. Heat the reaction mixture for 5.5 h at 90° C. and then concentrate it. Dissolve the residue in 2 N hydrochloric acid and reflux for 3 h. Cool the reaction mixture to room temperature, filter through diatomaceous earth, and concentrate under vacuum until white needles form. Filter the crystals, wash with ether, and dry under vacuum to obtain the title compound (90.0 g, 75%). [α]D$^{20}$+10.0 (c=1.0 in methanol). $^1$H NMR (400 MHz, D$_2$O), δ 2.34-2.39 (m, 1H), 2.45-2.53 (m, 1H), 3.38 (dd, 1H), 3.45 (d, 1H), 4.50 (dd, 1H), 4.58 (br s, 1H).

PREPARATION 26

(2R,4R)-4-Hydroxy-pyrrolidine-1,2-dicarboxylic acid 1-tert-butyl ester 2-methyl ester Add thionyl chloride (1.81 mol, 213.8 g, 1.5 eq) drop wise to a solution of (2R,4R)-4-hydroxy-pyrrolidine-2-carboxylic acid hydrochloride (1.19 mol, 200 g) in dry methanol (2 L) at 0° C. under a nitrogen atmosphere. Upon complete addition, warm the reaction mixture to room temperature and stir for 6 h. Concentrate the reaction mixture under reduced pressure to obtain the corresponding methyl ester hydrochloride. Add triethylamine (265.9 g, 2.63 mol) to a solution of methyl ester hydrochloride in dry dichloromethane (2 L) at 0° C. and stir for 30 min. Then add N,N-dimethylaminopyridine (0.18 mol, 21.9 g) and di-tert-butyl dicarbonate (1.43 mol, 313.5 g) consecutively. Warm the reaction mixture to room temperature and stir for 18 h. Quench the reaction mixture with water, separate the organic layer and wash with water and NaHCO$_3$ solution. Dry the organic layer over anhydrous sodium sulfate, filter, and concentrate under vacuum to obtain the title compound (260 g, 88%) as a thick oil. $^1$H NMR (400 MHz, CDCl$_3$) δ 1.43 (s, 9H), 1.46 (s, 9H), 2.05-2.10 (m, 2H), 2.26-2.35 (m, 2H), 3.48-3.56 (m, 2H), 3.58-3.61 (m, 1H), 3.64-3.70 (m, 2H), 3.77 (s, 3H), 3.79 (s, 3H), 4.27-4.29 (m, 1H), 4.34-4.38 (m, 2H).

PREPARATION 27

(2S,4R)-4-Methanesulfonyloxy-pyrrolidine-1,2-dicarboxylic acid 1-tert-butyl ester 2-methyl ester Add methanesulfonyl chloride (1.56 mol, 179 g) drop wise to a solution of (2S,4R)-4-hydroxy-pyrrolidine-1,2-dicarboxylic acid 1-tert-butyl ester 2-methyl ester (0.65 mol, 160 g) in pyridine (600 mL) at 0° C. under a nitrogen atmosphere. Upon complete addition, warm the reaction mixture to room temperature and stir for 2 h. Dilute the reaction mixture with dichloromethane, wash with 0.1 N hydrochloric acid solution and saturated sodium bicarbonate solution. Dry the organic layer over anhydrous sodium sulfate, filter, and concentrate under vacuum to obtain the title compound (185 g, 91%) as a thick oil. ES-MS m/z 324.1 [M+1]$^+$, 224.0 [M–Boc]$^+$.

PREPARATION 28

(2R,4R)-4-Methanesulfonyloxy-pyrrolidine-1,2-dicarboxylic acid 1-tert-butyl ester 2-methyl ester Prepare the title compound essentially as described in Preparation 27 from (2R,4R)-4-hydroxy-pyrrolidine-1,2-dicarboxylic acid 1-tert-butyl ester 2-methyl ester. ES-MS m/z 324.1 [M+1]$^+$.

PREPARATION 29

(2S,4S)-4-Bromo-pyrrolidine-1,2-dicarboxylic acid 1-tert-butyl ester 2-methyl ester Add triphenylphosphine (0.88 mol, 231 g) in portions to a solution of (2S,4R)-4-hydroxy-pyrrolidine-1,2-dicarboxylic acid 1-tert-butyl ester 2-methyl ester (0.58 mol, 144 g) and CBr$_4$ (0.88 mol, 292 g) in dry dichloromethane (1.44 L) at 0° C. Upon complete addition, warm the reaction mixture to room temperature and stir for 4 h. Add ethanol (1.44 L) and stir for an additional 2 h. Add diethyl ether (1.44 L) to the reaction mixture, filter the precipitated triphenylphosphine oxide, and concentrate the filtrate under reduced pressure. Purify by column chromatography using 5% ethyl acetate in hexanes as eluent to obtain the title compound (155 g, 85%) as a thick oil. ES-MS m/z 308 [M+1]$^+$.

PREPARATION 30

(2R,4S)-4-Bromo-pyrrolidine-1,2-dicarboxylic acid 1-tert-butyl ester 2-methyl ester Prepare the title compound essentially as described in Preparation 29 from (2R,4R)-4-hydroxy-pyrrolidine-1,2-dicarboxylic acid 1-tert-butyl ester 2-methyl ester. $^1$H NMR (400 MHz, CDCl$_3$) δ 1.45-1.47 (s, 9H), 2.38-2.45 (m, 1H), 2.54-2.59 (m, 1H), 3.72-3.74 (s, 3H), 3.84-3.87 (m, 1H), 3.92-3.94 (m, 1H), 4.44-4.54 (m, 2H).

PREPARATION 31

(2S,4S)-4-Azido-pyrrolidine-1,2-dicarboxylic acid 1-tert-butyl ester 2-methyl ester Heat a mixture of (2S,4R)-4-methanesulfonyloxy-pyrrolidine-1,2-dicarboxylic acid 1-tert-butyl ester 2-methyl ester (0.60 mol, 185 g) and sodium azide (1.20 mol, 78 g,) in N,N-dimethylformamide (1 L) to 80° C. for 16 h. Dilute the reaction mixture with water and extract with ethyl acetate. Wash the combined organic layers with 0.5 N hydrochloric acid, saturated sodium bicarbonate solution, and brine. Dry over anhydrous sodium sulfate, filter, and concentrate under vacuum to obtain the title compound (140 g, 88%) as a thick, yellow oil. ES-MS m/z 271.2 [M+1]$^+$, 171.0 [M−Boc]$^+$.

Prepare the intermediates in the table below by essentially following the procedures as described in Preparation 31 starting from the appropriate bromo or mesyl-pyrrolidine.

| Prep | Chemical Name | Physical Data |
|---|---|---|
| 32* | (2S,4R)-4-Azido-pyrrolidine-1,2-dicarboxylic acid 1-tert-butyl ester 2-methyl ester | |
| 33 | (2R,4R)-4-Azido-pyrrolidine-1,2-dicarboxylic acid 1-tert-butyl ester 2-methyl ester | $^1$H NMR (400 MHz, CDCl$_3$) δ 1.40-1.41 (s, 9H), 2.09-2.13 (m, 1H), 2.40-2.44 (m, 1H), 3.37-3.45 (m, 1H), 3.61-3.65 (m, 1H), 3.67-3.69 (s, 3H), 4.09-4.15 (m, 1H), 4.25-4.38 (m, 1H). |
| 34 | (2R,4S)-4-Azido-pyrrolidine-1,2-dicarboxylic acid 1-tert-butyl ester 2-methyl ester | ES-MS m/z 271 [M + 1]$^+$, 171.1 [M − Boc]$^+$ base peak |

*65° C. for 16 h

PREPARATION 35

(2S,4S)-4-Azido-2-hydroxymethyl-pyrrolidine-1-carboxylic acid tert-butyl ester Add lithium borohydride (0.16 mol, 3.6 g) to a solution of (2S,4S)-4-azido-pyrrolidine-1,2-dicarboxylic acid 1-tert-butyl ester 2-methyl ester (0.16 mol, 40 g) in anhydrous diethyl ether (400 mL) at −10 to −20° C. under a nitrogen atmosphere. Upon complete addition, stir the reaction mixture for 30 min at the same temperature. Quench the reaction mixture with saturated sodium bicarbonate solution at −70° C. and allow it to come to room temperature slowly. Separate the organic layer and extract the aqueous layer with dichloromethane. Dry the organic layer over anhydrous sodium sulfate, filter, and concentrate under vacuum to obtain the title compound (32 g, crude) as a thick, yellow oil. $^1$H NMR (400 MHz, CDCl$_3$) δ 1.46 (s, 9H), 2.32-2.35 (m, 1H), 3.30 (dd, 1H), 3.65-3.79 (m, 4H), 4.07-4.29 (m, 2H).

Prepare the intermediates in the table below by essentially following the procedures as described in Preparation 35 starting from the appropriate pyrrolidine-2-carboxylic acid methyl ester.

| Prep | Chemical Name |
|---|---|
| 36 | (2S,4R)-4-Azido-2-hydroxymethyl-pyrrolidine-1-carboxylic acid tert-butyl ester |
| 37 | (2R,4R)-4-Azido-2-hydroxymethyl-pyrrolidine-1-carboxylic acid tert-butyl ester |
| 38 | (2R,4S)-4-Azido-2-hydroxymethyl-pyrrolidine-1-carboxylic acid tert-butyl ester |

PREPARATION 39

(2S,4S)-4-Amino-2-hydroxymethyl-pyrrolidine-1-carboxylic acid tert-butyl ester

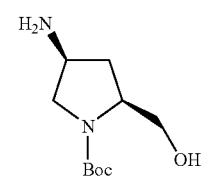

Dissolve (2S,4S)-4-azido-2-hydroxymethyl-pyrrolidine-1-carboxylic acid tert-butyl ester (32 g) in methanol (150 mL). Add 10% palladium on carbon (3.2 g) and hydrogenate (1 atm) at room temperature for 16 h. Filter off the catalyst through a plug of diatomaceous earth and concentrate under vacuum to obtain the title compound (28 g, crude) as a thick, yellow oil.

Prepare the intermediates in the table below by essentially following the procedures as described in Preparation 39 starting from the appropriate azido-pyrrolidine.

| Prep | Chemical Name | Structure |
|---|---|---|
| 40 | (2S, 4R)-4-Amino-2-hydroxymethyl-pyrrolidine-1-carboxylic acid tert-butyl ester | 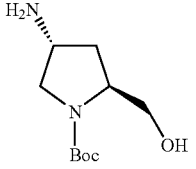 |
| 41 | (2R, 4R)-4-Amino-2-hydroxymethyl-pyrrolidine-1-carboxylic acid tert-butyl ester | 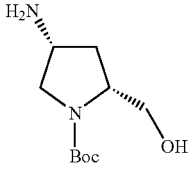 |
| 42 | (2R, 4S)-4-Amino-2-hydroxymethyl-pyrrolidine-1-carboxylic acid tert-butyl ester | 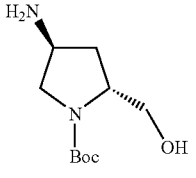 |

PREPARATION 43

(2S,4S)-4-(4-Bromo-2-nitro-phenylamino)-2-hydroxymethyl-pyrrolidine-1-carboxylic acid tert-butyl ester

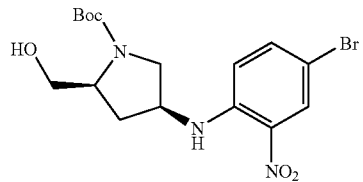

Heat a mixture of (2S,4S)-4-amino-2-hydroxymethyl-pyrrolidine-1-carboxylic acid tert-butyl ester (0.14 mol, 31 g), 5-bromo-2-fluoronitrobenzene (0.29 mol, 64.0 g) and triethylamine (0.58 mol, 59 g) in ethyl acetate (320 mL) to reflux for 16 h. Cool the reaction mixture to room temperature, dilute with ethyl acetate, and wash with water and brine. Dry the organic layer over anhydrous sodium sulfate, filter, and concentrate to obtain the title compound (42 g, crude) as a thick, dark, orange oil.

PREPARATION 44

(2S,4S)-[4-(4-Bromo-2-nitro-phenylamino)-pyrrolidin-2-yl]-methanol, hydrochloride

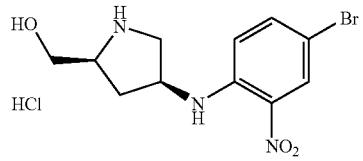

Add 4.0 M hydrogen chloride in dioxane (950 mL) slowly to a solution of (2S,4S)-4-(4-bromo-2-nitro-phenylamino)-2-hydroxymethyl-pyrrolidine-1-carboxylic acid tert-butyl ester (0.22 mol, 95 g) in dry dichloromethane (475 mL) at room temperature and stir for 2 h. Filter the precipitated solid and dry under vacuum to obtain the title compound (70 g, 87%) as an orange solid. $^1$H NMR (400 MHz, CD$_3$OD) δ 1.98-2.05 (m, 1H), 2.71-2.79 (m, 1H), 3.36 (dd, 1H), 3.58-3.63 (m, 1H), 3.76 (dd, 1H), 3.88-3.95 (m, 2H), 4.55-4.58 (m, 1H), 7.03 (d, 1H), 7.66 (dd, 1H), 8.30 (d, 1H).

Prepare the intermediates in the table below by essentially following the procedures as described in Preparations 43 and 44 starting from the appropriate amino-pyrrolidine.

| Prep | Chemical Name | Physical Data |
|---|---|---|
| 45 | (2S,4R)-[4-(4-Bromo-2-nitro-phenylamino)-pyrrolidin-2-yl]-methanol, hydrochloride | $^1$H NMR (400 MHz, DMSO-d$_6$) δ 2.01-2.10 (m, 2H), 3.06-3.10 (m, 2H), 3.47-3.60 (m, 3H), 3.62-3.71 (m, 2H), 3.83 (br s, 1H), 4.49-4.50 (m, 1H), 7.09 (d, 1H), 7.72 (dd, 1H), 7.94 (d, 1H), 8.2 (d, 1H), 9.10 (br s, 1H, HCl), 9.60 (br s, 1H, HCl). |
| 46 | (2R,4R)-[4-(4-Bromo-2-nitro-phenylamino)-pyrrolidin-2-yl]-methanol, hydrochloride | $^1$H NMR (400 MHz, DMSO-d$_6$) δ 1.80-1.85 (m, 1H), 2.54-2.59 (m, 1H), 3.43-3.51 (m, 3H), 3.56-3.63 (m, 1H), 3.69-3.72 (m, 2H), 4.50-4.51 (m, 1H), 7.10 (d, 1H), 7.55 (dd, 1H), 8.14 (d, 1H, —NH), 8.20 (d, 1H). |
| 47 | (2R,4S)-[4-(4-Bromo-2-nitro-phenylamino)- | $^1$H NMR (400 MHz, DMSO-d$_6$) δ 2.08-2.21 (m, 2H), 3.27 (d, 1H), 3.57-3.61 (m, |

| Prep | Chemical Name | Physical Data |
|---|---|---|
| | pyrrolidin-2-yl]-methanol, hydrochloride | 2H), 3.68-3.71 (m, 1H), 3.83 (br s, 1H), 4.47-4.51 (m, 1H), 5.44 (br s, 1H), 7.08 (d, 1H), 7.72 (dd, 1H), 7.94 (d, 1H), 8.20 (d, 1H), 9.06 (br s, 1H), 9.59 (br s, 1H). |

PREPARATION 48

(7S,8aS)-7-(4-Bromo-2-nitro-phenylamino)-tetrahydro-pyrrolo[2,1-c][1,4]oxazin-4-one

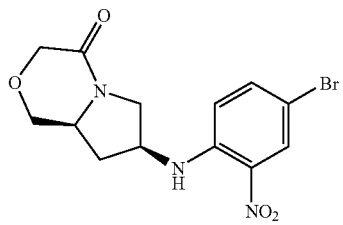

Add chloroacetyl chloride (0.49 mol, 55.7 g) drop wise to a solution of (2S,4S)-[4-(4-bromo-2-nitro-phenylamino)-pyrrolidin-2-yl]-methanol, hydrochloride (0.22 mol, 79 g) in tetrahydrofuran/water (1:1) mixture (1180 mL) at room temperature. Maintain the reaction pH between 10-12 by continuous addition of 4 M sodium hydroxide solution. After complete addition of chloroacetyl chloride, stir the reaction mixture for 4 h at room temperature. Remove tetrahydrofuran under reduced pressure and extract the aqueous layer with dichloromethane. Dry the organic layer over anhydrous sodium sulfate, filter, and concentrate to obtain the title compound (50 g, 62%) as an orange solid. $^1$H NMR (400 MHz, CDCl$_3$) δ 1.59-1.67 (m, 1H), 2.58-2.64 (m, 1H), 3.40 (t, 1H), 3.71 (dd, 1H), 3.91-4.01 (m, 2H), 4.09 (d, 1H), 4.20 (dd, 1H), 4.29-4.35 (m, 2H), 6.75 (d, 1H), 7.54 (dd, 1H), 8.05 (d, 1H), 8.32 (d, 1H).

PREPARATION 49

(4-Bromo-2-nitro-phenyl)-((7S,8aS)-hexahydro-pyrrolo[2,1-c][1,4]oxazin-7-yl)-amine

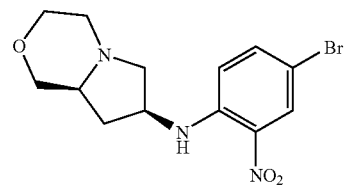

Add BH$_3$.THF (1.0 M in tetrahydrofuran, 0.056 mol, 56 mL) drop wise to a solution of (7S,8aS)-7-(4-bromo-2-nitrophenylamino)-tetrahydro-pyrrolo[2,1-c][1,4]oxazin-4-one (0.028 mol, 10 g) in tetrahydrofuran (150 mL) at 0 to −5° C. under nitrogen. After complete addition, reflux the reaction mixture for 3 h. Cool the reaction mixture to 0° C., quench with 1 N hydrochloric acid, and then add 1 N aqueous sodium hydroxide solution. Remove tetrahydrofuran under reduced pressure and extract the aqueous layer with dichloromethane. Dry the organic layer over anhydrous sodium sulfate, filter, and concentrate. Dissolve the residue in methanol (160 mL), add 4 N hydrogen chloride in dioxane (160 mL) and heat the reaction mixture for 4 h at 80° C. Cool to room temperature and adjust the pH between 10-12 by adding 4 N aqueous sodium hydroxide solution. Remove the methanol under reduced pressure and extract the aqueous layer with dichloromethane. Dry the organic layer over anhydrous sodium sulfate, filter, and concentrate to give the title compound as a crystalline, yellow solid (8.0 g, 83%). $^1$H NMR (400 MHz, CDCl$_3$) δ 1.32-1.38 (m, 1H), 2.19-2.22 (m, 1H), 2.34 (dt, 1H), 2.42-2.47 (m, 1H), 2.54-2.58 (m, 1H), 2.92 (d, 1H), 3.07 (d, 1H), 3.34 (t, 1H), 3.61 (dt, 1H), 3.85 (dd, 1H), 3.97 (dd, 1H), 4.01-4.07 (m, 1H), 6.67 (d, 1H), 7.48 (dd, 1H), 8.17 (d, 1H), 8.35 (d, 1H).

Prepare the intermediates in the table below by essentially following the procedures as described in Preparations 48 and 49 starting from the appropriate phenyl-amino-pyrrolidine. Perform the reduction of the tetrahydro-pyrrolo[2,1-c][1,4] oxazin-4-one with borane-tetrahydrofuran complex or borane-dimethyl sulfide complex, for example, with Preparations 50 and 51.

| Prep | Chemical Name | Physical data |
|---|---|---|
| 50 | (7R,8aS)-(4-Bromo-2-nitro-phenyl)-(hexahydro-pyrrolo[2,1-c][1,4]oxazin-7-yl)-amine | $^1$H NMR (400 MHz, CDCl$_3$) δ 1.30-1.36 (m, 1H), 2.18-2.25 (m, 1H), 2.31-2.38 (m, 1H), 2.42-2.47 (m, 1H), 2.53-2.58 (m, 1H), 2.90 (d, 1H), 3.06 (d, 1H), 3.34 (t, 1H), 3.62 (dt, 1H), 3.86 (dd, 1H), 3.97 (dd, 1H), 4.01-4.09 (m, 1H), 6.67 (d, 1H), 7.49 (dd, 1H), 8.16 (d, 1H, —NH), 8.32 (d, 1H). |
| 51 | (7R,8aR)-(4-Bromo-2-nitro-phenyl)- | $^1$H NMR (400 MHz, CDCl$_3$) δ 1.30-1.36 (m, 1H), 2.18-2.25 (m, 1H), 2.31-2.38 (m, |

| Prep | Chemical Name | Physical data |
|------|---------------|---------------|
|  | (hexahydro-pyrrolo[2,1-c][1,4]oxazin-7-yl)-amine | 1H), 2.42-2.47 (m, 1H), 2.53-2.58 (m, 1H), 2.90 (d, 1H), 3.06 (d, 1H), 3.34 (t, 1H), 3.62 (dt, 1H), 3.86 (dd, 1H), 3.97 (dd, 1H), 4.01-4.09 (m, 1H), 6.67 (d, 1H), 7.49 (dd, 1H), 8.16 (d, 1H, —NH), 8.32 (d, 1H). |
| 52 | (7S,8aR)-(4-Bromo-2-nitro-phenyl)-(hexahydro-pyrrolo[2,1-c][1,4]oxazin-7-yl)-amine | $^1$H NMR (400 MHz, CDCl$_3$) δ 1.69 (dd, 1H), 1.88-1.96 (m, 1H), 2.17-2.24 (m, 1H), 2.42-2.48 (m, 2H), 2.93 (d, 1H), 3.27 (t, 1H), 3.57 (t, 1H), 3.68-3.75 (m, 1H), 3.87 (d, 1H), 3.97 (d, 1H), 4.09-4.17 (m, 1H), 6.69 (d, 1H), 7.50 (d, 1H), 8.07 (d, 1H), 8.32 (d, 1H). |

PREPARATION 53

Tert-butyl 2,5-dihydro-1H-pyrrole-1-carboxylate

Add a solution of di-tert-butyl dicarbonate (0.69 mol, 151.0 g) in methylene chloride (200 mL) dropwise to a solution of 3-pyrroline (40.0 g, 0.57 mol) in methylene chloride (400 mL) over a period of 1.5 h at 0° C. and stir at room temperature for 10 h. Remove the solvent and carry the crude product on to the next step, Preparation 47 (95.0 g, 98%).

PREPARATION 54

Rac-trans-3-Bromo-4-hydroxy-pyrrolidine-1-carboxylic acid tert-butyl ester

To a stirred mixture of tert-butyl 2,5-dihydro-1H-pyrrole-1-carboxylate (0.29 mol, 50.0 g) in dimethylsulfoxide (360 mL) and water (18 mL) add N-bromosuccinimide (0.325 mol, 58.0 g) gradually over 15 min at 0° C. After stirring at room temperature for 2 h, add water (500 mL) and extract with ethyl acetate.

Wash the organic layer with brine, dry over sodium sulfate and concentrate in vacuo to obtain the title compound as a light brown oil (75.0 g, 95%). $^1$H NMR (500 MHz, CDCl$_3$) δ 4.43-4.53 (m, 1H), 4.12-4.20 (m, 1H), 3.96-4.11 (m, 2H), 3.68-3.94 (m, 2H), 3.32-3.48 (m, 1H), 1.47 (s, 9H).

PREPARATION 55

Rac-trans-3-Benzylamino-4-hydroxy-pyrrolidine-1-carboxylic acid tert-butyl ester Stir a mixture of crude rac-trans-3-bromo-4-hydroxy-pyrrolidine-1-carboxylic acid tert-butyl ester (75.0 g) and aqueous 1 N sodium hydroxide (400 mL) at room temperature for 2 h. Add benzylamine (0.86 mol, 80.0 g,), stir at 65° C. for 4.5 h and then cool to 0° C. Collect the resultant precipitates by filtration, wash with water and isopropyl ether and dry to obtain the title compound as a white solid (50.0 g, 63%). $^1$H NMR (300 MHz, CDCl$_3$) δ 7.21-7.38 (m, 5H), 4.06-4.15 (m, 1H), 3.84 (d, J=5.0 Hz, 2H), 3.57-3.75 (m, 2H), 3.10-3.35 (m, 3H), 1.65 (br s, 2H), 1.46 (s, 9H).

PREPARATION 56

(3S,4S)-3-Benzylamino-4-hydroxy-pyrrolidine-1-carboxylic acid tert-butyl ester, (+)-mandelic acid salt Heat a mixture of rac-trans-3-benzylamino-4-hydroxy-pyrrolidine-1-carboxylic acid tert-butyl ester (0.343 mol, 100.0 g) and (+)-mandelic acid (0.378 mol, 57.83 g) in acetonitrile (1 L) and water (10 mL) at 70° C. for one hour and then cool to room temperature during 4 h. Collect the resultant crystalline precipitate by filtration, wash with acetonitrile, and recrystallize from acetonitrile/water (20:1) to give the title compound as a white crystalline solid (62.0 g, 40%). $^1$H NMR (500 MHz, CDCl$_3$) δ 7.19-7.44 (m, 8H), 5.05 (br s, 2H), 4.97 (s, 1H), 3.95-4.02 (m, 1H), 3.73 (s, 2H), 3.28-3.50 (m, 4H), 2.95-3.18 (m, 3H), 1.39 (s, 9H); mp 185-188, $[α]^{23}_D$ +50.0° (c 0.50, MeOH).

PREPARATION 57

(3S,4S)-3-Benzylamino-4-hydroxy-pyrrolidine-1-carboxylic acid tert-butyl ester

To (3S,4S)-3-benzylamino-4-hydroxy-pyrrolidine-1-carboxylic acid tert-butyl ester (+)-mandelic acid salt (60.0 g) add 3% aqueous potassium carbonate (300 mL) and extract the free amine with ethyl acetate (3×250 mL). Wash the combined organic layer with brine and dry over anhydrous sodium sulfate. Evaporate the solvent under reduced pressure to obtain the (S,S)-enantiomer as a white solid (34.0 g, 65%). APCI MS m/z 293 [M+H]$^+$; mp 69-70° C., $[α]^{23}_D$+18.0° (c, 0.50, MeOH).

PREPARATION 58

(3S,4S)-3-Amino-4-hydroxy-pyrrolidine-1-carboxylic acid tert-butyl ester

To a solution of (3S,4S)-3-benzylamino-4-hydroxy-pyrrolidine-1-carboxylic acid tert-butyl ester (0.054 mol, 16.0 g) in n-butanol (225 mL) add 10% Pd/C (5.0 g) and hydrogenate the mixture at 50 psi for 10 h. Filter the reaction mixture thorough a plug of diatomaceous earth and wash with ethanol. Evaporate the filtrate to obtain the title compound as a white solid (11.10 g, 99%). APCI MS m/z 203 [M+H]$^+$; $[α]^{23}_D$ +7.8° (c, 0.50, MeOH).

PREPARATION 59

(3S,4S)-3-(4-Bromo-2-nitro-phenylamino)-4-hydroxy-pyrrolidine-1-carboxylic acid tert-butyl ester To a solution of 1-bromo-4-fluoro-3-nitrobenzene (0.125 mol, 26.0 g) in ethyl acetate (300 mL) add (3S,4S)-3-benzylamino-4-hydroxy-pyrrolidine-1-carboxylic acid tert-butyl ester (0.113 mol, 23.0 g) and triethylamine (0.339 mol, 35.0 g), reflux for 14 h, cool to room temperature, and wash with water and brine. Dry over anhydrous sodium sulfate, evaporate the solvent, and purify by flash column chromatography to give the title compound as a yellow solid (43.0 g, 90%). APCI MS m/z 403 [M+H]+.

PREPARATION 60

(3R,4R)-3-Benzylamino-4-hydroxy-pyrrolidine-1-carboxylic acid tert-butyl ester, (−)-mandelic acid salt Mix racemic trans-3-benzylamino-4-hydroxy-pyrrolidine-1-carboxylic acid tert-butyl ester (0.085 mol, 25.0 g) and (−)-mandelic acid (0.094 mol, 14.45 g, 1.1 eq) in acetonitrile (200 mL) and water (5 mL) at 70° C. for one hour. Cool to room temperature during 4 h. Collect the resulting crystalline precipitate by filtration, wash with acetonitrile, and recrystallize from acetonitrile/water (20:1) to obtain the (−)-mandelic acid salt as a white crystalline solid (34.0 g, 88%). $^1$H NMR (500 MHz, CDCl$_3$) δ 7.19-7.44 (m, 8H); 5.05 (br s, 2H), 4.97 (s, 1H), 3.95-4.02 (m, 1H), 3.73 (s, 2H), 3.28-3.50 (m, 4H), 2.95-3.18 (m, 3H), 1.39 (s, 9H); $[α]^{23}_D$ −58.0° (c 0.50, MeOH).

PREPARATION 61

(3R,4R)-3-(4-Bromo-2-nitro-phenylamino)-4-hydroxy-pyrrolidine-1-carboxylic acid tert-butyl ester Prepare the title compound by essentially following the procedures as described in Preparations 58, 59, and 60 starting from (3R,4R)-3-benzylamino-4-hydroxy-pyrrolidine-1-carboxylic acid tert-butyl ester (−)-mandelic acid salt.

PREPARATION 62

(3S,4R)-tert-butyl 3-(4-bromo-2-nitrophenylamino)-4-(2-chloroacetoxy)pyrrolidine-1-carboxylate To a mixture of (3S,4S)-tert-butyl 3-(4-bromo-2-nitrophenylamino)-4-hydroxypyrrolidine-1-carboxylate (2.50 mmol, 1.0 g), chloroacetic acid (3.0 mmol, 300 mg) and triphenylphosphine (3.0 mmol, 850 mg) in tetrahydrofuran (40 mL) add diethylazodicarboxylate (3.0 mmol, 600 mg) and stir at room temperature for 12 h. Remove the solvent, add ethyl acetate (50 mL) to the residue and wash with water and brine. Dry over anhydrous sodium sulfate and evaporate. Purify the residue by column chromatography, eluting with 20% ethyl acetate in methylene chloride to obtain the title compound as a yellow solid (1.10 g, 98%). $^1$H NMR (500 MHz, CDCl$_3$) δ 8.35 (s, 1H), 8.20 (m, 1H), 7.60 (m, 1H), 6.82 (m, 1H), 5.55 (d, J=6.8 Hz, 1H), 4.32 (m, 1H), 4.13 (bd, J=8.2 Hz, 2H), 3.90 (m, 1H), 3.79 (m, 1H), 3.74 (dd, J=4.2, 10.4 Hz, 1H), 3.25 (t, J=7.20 Hz, 1H), 1.41 (s, 9H).

PREPARATION 63

(3S,4R)-tert-butyl 3-(4-bromo-2-nitrophenylamino)-4-hydroxypyrrolidine-1-carboxylate To a solution of the (3S,4R)-tert-butyl 3-(4-bromo-2-nitrophenylamino)-4-(2-chloroacetoxy)pyrrolidine-1-carboxylate (2.20 mmol, 1.0 g) in methanol add 2.0 M aqueous lithium hydroxide (5 mL) and stir at room temperature for 3.5 h. Remove the solvent, dilute the residue with ethyl acetate (50 mL), and wash with water and brine. Dry over anhydrous sodium sulfate, filter, and evaporate the solvent. Purify by column chromatography eluting with 50% ethyl acetate in methylene chloride to obtain the title compound as a yellow solid (900 mg, 98%). APCI MS m/z 462 [M+H]+.

PREPARATION 64

(3R,4S)-tert-butyl 3-(4-bromo-2-nitrophenylamino)-4-hydroxypyrrolidine-1-carboxylate Prepare the title compound by essentially following the procedures as described in Preparations 62 and 63 starting from (3R,4R)-tert-butyl 3-(4-bromo-2-nitrophenylamino)-4-hydroxypyrrolidine-1-carboxylate.

PREPARATION 65

(3S,4S)-4-(4-Bromo-2-nitro-phenylamino)-pyrrolidin-3-ol, hydrochloride

To a suspension of the (3S,4S)-3-(4-bromo-2-nitro-phenylamino)-4-hydroxy-pyrrolidine-1-carboxylic acid tert-butyl ester (0.106 mol, 43.0 g) in ethyl acetate (500 mL) at 0° C. bubble anhydrous hydrogen chloride gas for 10 min and stir at room temperature for one hour. Remove the solvent and dry the resultant solid under vacuum to give the title compound as a yellow solid (35.0 g, 98%). APCI MS m/z 302 [M+H]+.

PREPARATION 66

(3S,4S)-4-(4-Bromo-2-nitro-phenylamino)-1-methyl-pyrrolidin-3-ol

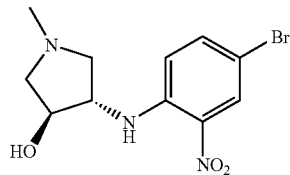

To (3S,4S)-4-(4-Bromo-2-nitro-phenylamino)-pyrrolidin-3-ol hydrochloride (0.104 mol, 35.0 g) in acetonitrile add sodium triacetoxyborohydride (0.37 mol, 78.0 g) at 0° C. To this mixture, add slowly 37% aqueous formaldehyde (30 mL) over 10 min and stir at room temperature for 10 h. Add saturated aqueous sodium bicarbonate and stir for one hour. Extract with ethyl acetate, and wash with water and brine. Dry over anhydrous sodium sulfate, filter, and evaporate the solvent to obtain the title compound as a yellow solid (34.0 g, 98%). APCI MS m/z 302 [M+H]+; $[α]^{23}_D$ +58.6° (c, 0.50, MeOH).

Prepare the intermediates in the table below by essentially following the procedures as described in Preparations 65 and 66 wherein the appropriate tert-butyl 3-(4-bromo-2-nitrophenylamino)-4-hydroxypyrrolidine-1-carboxylate is treated with anhydrous HCl gas for 10-30 min and then stirred for 1-4 h. Treat the resulting deprotected pyrrolidine with formaldehyde for 15 min to 10 h.

| Prep | Chemical Name | Physical Data |
|---|---|---|
| 67 | (3R,4R)-4-(4-Bromo-2-nitro-phenylamino)-1- | $^1$H NMR (300 MHz, CDCl$_3$) δ 8.21 (d, J = 7.9 Hz, 1H), 7.57 (dd, J = 3.5, 8.8 Hz, 1H), 7.08 (d, J = 8.1 Hz, 1H), 4.11 (m, 1H), |

-continued

| Prep | Chemical Name | Physical Data |
|---|---|---|
| | methyl-pyrrolidin-3-ol | 3.92 (m, 1H), 3.21 (dd, J = 3.8, 7.9 Hz, 1H), 3.12 (dd, J = 4.8, 8.9 Hz, 1H), 2.71 (dd, J = 3.8, 8.8 Hz, 1H), 2.59 (dd, J = 4.8, 8.9 Hz, 1H), 2.41 (s, 3H) |
| 68 | (3R,4S)-4-(4-bromo-2-nitrophenylamino)-1-methylpyrrolidin-3-ol | ESI MS m/z 318 [M + H]+ |
| 69 | (3S,4R)-4-(4-bromo-2-nitrophenylamino)-1-methylpyrrolidin-3-ol | ¹H NMR (300 MHz, CDCl₃) δ 8.66 (d, J = 5.4 Hz, 1H), 8.33 (d, J = 2.4 Hz, 1H), 7.48 (dd, J = 9.2, 2.1 Hz, 1H), 6.67 (d, J = 9.3 Hz), 4.43-4.41 (m, 1H), 4.05-4.00 (m, 1H), 2.90-2.73 (m, 3H), 2.68-2.63 (m, 1H), 2.38 (s, 3H) |

PREPARATION 70

4-Hydroxy-piperidine-1-carboxylic acid tert-butyl ester

Add sodium borohydride (0.82 mol, 31.3 g) in portions to a solution of 1-(tert-butoxycarbonyl)-4-piperidone (0.74 mol, 150 g) and triethylamine (1.5 mol, 151.6 g) in dichloromethane (1 L) at 0° C. Upon complete addition, warm the reaction mixture to room temperature and stir for 4 h. Quench the reaction mixture with saturated ammonium chloride solution and remove the ethanol under reduced pressure. Dissolve the residue in water and extract with dichloromethane. Dry the organic layer over anhydrous sodium sulfate, filter, and concentrate to obtain the title compound (150 g, 99%) as a viscous solid. ¹H NMR (400 MHz, CDCl₃) δ 1.45 (s, 9H), 1.53 (d, 2H), 1.83-1.87 (m, 2H), 3.02 (dt, 2H), 3.8-3.85 (m, 3H).

PREPARATION 71

4-Methanesulfonyloxy-piperidine-1-carboxylic acid tert-butyl ester

Add methanesulfonyl chloride (1.12 mol, 128.8 g) drop wise to a solution of 4-hydroxy-piperidine-1-carboxylic acid tert-butyl ester (0.74 mol, 150 g) and triethylamine (1.5 mol, 151.6 g) in dichloromethane (1 L) at 0° C. Upon complete addition, warm the reaction mixture to room temperature and stir for 16 h. Dilute the reaction mixture with dichloromethane, wash with saturated sodium bicarbonate solution and water. Dry the organic layer over anhydrous sodium sulfate, filter, and concentrate to obtain the title compound (192 g, 92%) as a brown solid. ¹H NMR (400 MHz, CDCl₃) δ 1.45 (s, 9H), 1.78-1.85 (m, 2H), 1.93-1.98 (m, 2H), 3.03 (s, 3H), 3.26-3.32 (m, 2H), 3.68-3.71 (m, 2H), 4.85-4.90 (m 1H).

PREPARATION 72

3,6-Dihydro-2H-pyridine-1-carboxylic acid tert-butyl ester

Heat a solution of 4-methanesulfonyloxy-piperidine-1-carboxylic acid tert-butyl ester (0.69 mol, 193 g) in DBU (400 mL) at 80° C. for 16 h. Dilute the reaction mixture with water, extract with diethyl ether, and wash the organic layer with 1 N hydrochloric acid and saturated sodium bicarbonate solution. Dry the organic layer over anhydrous sodium sulfate, filter, and concentrate to obtain the title compound (116 g, 92%) as a brown oil. ¹H NMR (400 MHz, CDCl₃) δ 1.46 (s, 9H), 2.12 (br s, 2H), 3.47 (t, 2H), 3.87 (s, 2H), 5.65 (br s, 1H), 5.81 (br s, 1H).

PREPARATION 73

Rac cis-7-Oxa-3-aza-bicyclo[4.1.0]heptane-3-carboxylic acid tert-butyl ester

Add a solution of m-chloroperoxybenzoic acid (0.77 mol, 133.1 g) in dichloromethane (200 mL) drop wise to a solution of 3,6-dihydro-2H-pyridine-1-carboxylic acid tert-butyl ester (0.64 mol, 117.8 g) in dichloromethane (1 L) at 0° C. Upon complete addition, warm the reaction mixture to room temperature and stir for 16 h. Dilute the reaction mixture with dichloromethane and wash with 4 N sodium hydroxide solution, water, and brine. Dry the organic layer over anhydrous sodium sulfate, filter, and concentrate to obtain the title compound (112 g, 87%) as a light yellow oil. ¹H NMR (400 MHz, CDCl₃) δ 1.44 (s, 9H), 1.87-1.93 (m s, 1H), 2.04 (br s, 1H), 3.11 (br s, 1H), 3.20 (br s, 1H), 3.28 (s, 1H), 3.44 (br s, 1H), 3.68 (br s 1H). 3.81-3.92 (m, 1H). ES-MS m/z 204 [M+H]+.

PREPARATION 74

Rac trans-4-Azido-3-hydroxy-piperidine-1-carboxylic acid tert-butyl ester

Heat a mixture of racemic trans-7-oxa-3-aza-bicyclo[4.1.0]heptane-3-carboxylic acid tert-butyl ester (0.56 mol, 112 g), sodium azide (1.12 mol, 73.08 g), ammonium chloride (0.56 mol, 30.07 g) and methanol/water (3:1) (1 L) at 65° C. for 16 h. Dilute the reaction mixture with water, extract with dichloromethane, and wash the organic layer with saturated sodium bicarbonate and brine solution. Dry the organic layer over anhydrous sodium sulfate, filter, and concentrate. Purify the residue on a silica gel column using 6% ethyl acetate in hexanes as eluent to obtain the title compound (42.3 g, 42%) as a light yellow oil. ¹H NMR (400 MHz, CDCl₃) δ 1.48 (s, 9H), 1.84 (br s 1H), 1.97-2.01 (m, 1H), 2.74-2.82 (m, 1H), 2.88 (br s, 1H), 3.37-3.40 (m, 1H), 3.50 (br s, 1H), 3.91 (br s, 1H), 4.09 (dd, 1H). ES-MS m/z 143 [M−Boc]+.

PREPARATION 75

Rac trans-4-Amino-3-hydroxy-piperidine-1-carboxylic acid tert-butyl ester

Dissolve racemic trans-4-azido-3-hydroxy-piperidine-1-carboxylic acid tert-butyl ester (0.23 mol, 56.6 g) in methanol (500 mL), add 10% palladium on carbon (12.0 g) and hydrogenate (1 atm) at room temperature for 16 h. Filter off the catalyst through a plug of diatomaceous earth and concentrate the filtrate to obtain the title compound (53.7 g, 99%) as a thick, light yellow oil.

PREPARATION 76

Rac trans-4-Benzylamino-3-hydroxy-piperidine-1-carboxylic acid tert-butyl ester

Add benzaldehyde (0.24 mol, 26.3 g) to a solution of racemic trans-4-amino-3-hydroxy-piperidine-1-carboxylic acid tert-butyl ester (0.24 mol, 53.7 g), and acetic acid (92 mL) in ethanol (400 mL) and stir the reaction mixture at room temperature for 30 min. Add sodium cyanoborohydride (0.49 mol, 31.2 g) and stir the reaction mixture for 3 h. Quench the reaction mixture with sodium bicarbonate solution and extract with dichloromethane. Dry the organic layer over anhydrous sodium sulfate, filter, and concentrate. Dissolve the residue in a minimum amount of dichloromethane and add 0.1 N aqueous hydrochloric acid to maintain the pH between 4-5. Discard the organic layer. Wash the acidic aqueous layer three times with dichloromethane and discard the organic layer. Adjust the pH of the aqueous layer between 10-12 and extract with dichloromethane. Dry the organic layer over anhydrous sodium sulfate, filter, and concentrate to obtain the title compound (35.7 g, 46%) as a light yellow oil. $^1$H NMR (400 MHz, CDCl$_3$) δ 1.35-1.40 (m, 2H), 1.45 (s, 9H), 2.05 (br s 1H), 2.43 (t, 1H), 2.57 (t, 1H), 2.69 (br s, 1H), 3.27 (br s, 1H), 3.70 (d, 1H), 3.94 (d, 1H), 4.15 (br s, 1H), 4.26 (d, 1H), 7.23-7.29 (m, 1H), 7.30-7.32 (m, 2H), 7.33-7.36 (m, 2H).

PREPARATION 77

(3R,4R)-4-Benzylamino-3-hydroxy-4-piperidine-1-carboxylic acid tert-butyl ester, L-(+)-tartaric acid salt Heat a mixture of racemic trans-4-benzylamino-3-hydroxy-piperidine-1-carboxylic acid tert-butyl ester (0.11 mol, 35.0 g) and L-(+)-tartaric acid (0.12 mol, 18.9 g, 1.2 eq) and acetonitrile/water (20:1) (175 mL) at 75° C. for 4 h. Concentrate the reaction mixture under reduced pressure to obtain the tartaric acid salt (53.0 g). Crystallize the residue from acetonitrile three times. Filter the crystals and dry under vacuum to obtain the title compound (18.3 g, 67%). HPLC (Column: Chiralcel OD-H (250 mm*4.6 mm); solvent system: isopropanol/0.1% triethylamine in hexanes (8:92); flow rate: 0.800 ml/min; wavelength: 258 nm): 99.9% ee. $t_R$ 9.502 min. $t_R$ for opposite enantiomer ((3S,4S)-3-Hydroxy-4-phenethyl-piperidine-1-carboxylic acid tert-butyl ester.L-(-)-tartaric acid salt) 8.714 min.

PREPARATION 78

(3R,4R)-4-Amino-3-hydroxy-piperidine-1-carboxylic acid tert-butyl ester

Dissolve the (3R,4R)-4-benzyl-3-hydroxy-4-phenethyl-piperidine-1-carboxylic acid tert-butyl ester, L-(+)-tartaric acid salt (0.04 mol, 18.3 g) in 4% potassium carbonate solution (500 mL) and stir for 30 min. Extract the free amine with dichloromethane. Dry the organic layer over anhydrous sodium sulfate, filter, and concentrate to obtain the free amine (11.3 g, 92%). Dissolve the amine in methanol (110 mL), add 10% palladium on carbon (2.5 g) and hydrogenate (1 atm) at room temperature for 16 h. Filter off the catalyst through a plug of diatomaceous earth and concentrate the filtrate to obtain the title compound (7.6 g, 95%) as thick, light yellow oil. $[\alpha]_D^{26.1}$+2.141 (c 1.0, methanol). $^1$H NMR (400 MHz, DMSO-d$_6$) δ 1.08 (dq, 1H), 1.38 (s, 9H), 1.67 (dd, 1H), 1.80 (br s, 1H), 2.37-2.45 (m, 2H), 2.67 (br s, 1H), 2.90 (br s, 1H), 3.79 (br s, 1H), 3.88 (br s, 1H), 5.0 (br s, 1H). ES-MS m/z 217 [M+H]$^+$.

PREPARATION 79

(3R,4R)-4-(4-Bromo-2-nitro-phenylamino)-3-hydroxy-piperidine-1-carboxylic acid tert-butyl ester Heat a mixture of (3R,4R)-4-amino-3-hydroxy-piperidine-1-carboxylic acid tert-butyl ester (0.02 mol, 6.0 g), 5-bromo-2-fluoronitrobenzene (0.03 mol, 6.71 g) and triethyl amine (0.058 mol, 5.88 mL) in ethyl acetate (180 mL) to reflux for 16 h. Cool the reaction mixture to room temperature, dilute with ethyl acetate, and wash with water and brine. Dry the organic layer over anhydrous sodium sulfate, filter, and concentrate to obtain the title compound (12.35 g, crude). $^1$H NMR (400 MHz, CDCl$_3$) δ 1.46 (s, 9H), 1.50-1.51 (m, 1H), 2.08-2.12 (m, 1H), 2.93 (dd, 1H), 3.01 (br s, 1H), 3.55-3.61 (m, 1H), 3.62-3.68 (m, 1H), 3.68 (br s, 1H), 4.13-4.18 (m, 1H), 6.97 (d, 1H), 7.48 (dd, 1H), 8.08 (d, 1H), 8.30 (d, 1H). ES-MS m/z 316 [M–Boc]$^+$.

PREPARATION 80

(3R,4R)-4-(4-Bromo-2-nitro-phenylamino)-piperidin-3-ol.hydrochloride salt

Add 4.0 M hydrogen chloride in dioxane (70 mL) slowly to a solution of (3R,4R)-4-(4-bromo-2-nitro-phenylamino)-3-hydroxy-piperidine-1-carboxylic acid tert-butyl ester (0.027 mol, 11.5 g) in dry dichloromethane (40 mL) at room temperature and stir for 16 h. Filter the precipitate and dry under vacuum to obtain the title compound (8.68 g, 89%) as a yellow solid. $^1$H NMR (400 MHz, CD$_3$OD) δ 1.81-1.86 (m, 1H), 2.39-2.44 (m, 1H), 3.02-3.07 (m, 1H), 3.18-3.26 (m, 1H), 3.34-3.40 (m, 1H), 3.45 (dd, 1H), 3.87-3.91 (m, 2H), 7.17 (d, 1H), 7.61 (dd, 1H), 8.28 (d, 1H).

PREPARATION 81

(3R,4R)-4-(4-Bromo-2-nitro-phenylamino)-1-methyl-piperidin-3-ol

Add formaldehyde (20.5 mL, 37-41% aqueous solution) to a solution of (3R,4R)-4-(4-bromo-2-nitro-phenylamino)-piperidin-3-ol.hydrochloride salt (0.0024 mol, 8.68 g) and acetic acid (10.2 mL) in water (42 mL) and stir the reaction mixture at room temperature for 30 min. Add sodium cyanoborohydride (0.073 mol, 4.6 g) and stir the reaction mixture for 3 h. Quench the reaction mixture with sodium bicarbonate solution and extract with dichloromethane. Dry the organic layer over anhydrous sodium sulfate, filter, and concentrate to obtain the title compound (7.8 g, 97%). $^1$H NMR (400 MHz, CDCl$_3$) δ 1.63-1.71 (m, 1H), 2.16-2.21 (m, 2H), 2.33 (s, 3H), 2.35-2.38 (m, 1H), 2.60 (br s, 1H), 2.80 (d, 1H), 3.54-3.56 (m, 1H), 3.75-3.79 (m, 1H), 6.92 (d, 1H), 7.48 (dd, 1H), 8.14 (d, 1H), 8.30 (d, 1H).

PREPARATION 82

(3S,4S)-4-Benzylamino-3-hydroxy-4-piperidine-1-carboxylic acid tert-butyl ester, D-(-)-tartaric acid salt Concentrate the mother liquor of Preparation 77 to obtain enantio enriched (3S,4S)-3-hydroxy-4-phenethyl-piperidine-1-carboxylic acid tert-butyl ester L-(+)-tartaric acid salt (0.0377 mol, 17.2 g). Add 4% aqueous potassium carbonate solution (500 mL) and stir for 30 min. Extract the free amine with dichloromethane. Dry the organic layer over anhydrous sodium sulfate, filter, and concentrate to obtain the free amine (11.0 g). Heat a mixture of 4-benzylamino-3-hydroxy-piperidine-1-carboxylic acid tert-butyl ester (0.0361 mol, 11.0 g) and D-(-)-tartaric acid (0.0397 mol, 5.97 g, 1.1 equiv.) in acetonitrile/water (20:1) (100 ml) at 75° C. for 4 h. Concentrate the reaction mixture under reduce pressure to obtain crude tartaric acid salt. Crystallize the residue from acetonitrile three times. Filter the crystals and dry under vacuum to obtain the title compound (14.8 g, 90%). HPLC (Column: Chiralcel OD-H (250 mm*4.6 mm); solvent system: isopropanol/0.1% triethylamine in hexanes (8:92); flow rate: 0.800 ml/min; wavelength: 258 nm): 96.4% ee. $t_R$ 8.714 min. $t_R$ for opposite enantiomer ((3R,4R)-3-Hydroxy-4-phenethyl-piperidine-1-carboxylic acid tert-butyl ester.L-(+)-tartaric acid salt) 9.502 min.

PREPARATION 83

(3S,4S)-4-Amino-3-hydroxy-piperidine-1-carboxylic acid tert-butyl ester

Dissolve (3S,4S)-4-Benzylamino-3-hydroxy-4-phenethyl-piperidine-1-carboxylic acid tert-butyl ester, D-(−)-tartaric acid salt (0.036 mol, 16.4 g) in 4% aqueous potassium carbonate solution (500 mL) and stir for 30 min. Extract with dichloromethane, dry the organic layer over anhydrous sodium sulfate, filter, and concentrate to obtain the free amine (11.0 g, 99%). Dissolve the amine in methanol (110 mL), add 10% palladium on carbon (5.5 g) and hydrogenate (50 psi) at room temperature for 2 h. Filter off the catalyst through diatomaceous earth and concentrate to obtain the title compound (7.7 g, 99%) as a thick, light yellow oil.

PREPARATION 84

(3S,4S)-4-(4-Bromo-2-nitro-phenylamino)-3-hydroxy-piperidine-1-carboxylic acid tert-butyl ester Heat a mixture of (3S,4S)-4-amino-3-hydroxy-piperidine-1-carboxylic acid tert-butyl ester (0.035 mol, 7.5 g), 5-bromo-2-fluoronitrobenzene (0.038 mol, 8.48 g) and triethyl amine (0.073 mol, 7.44 g) in ethyl acetate (250 mL) to reflux for 16 h. Cool the reaction mixture to room temperature, dilute with ethyl acetate and wash with water and brine. Dry the organic layer over anhydrous sodium sulfate, filter, and concentrate to obtain the title compound (16.16 g, crude).

PREPARATION 85

(3S,4S)-4-(4-Bromo-2-nitro-phenylamino)-piperidin-3-ol, hydrochloride

Add 4 M hydrogen chloride in dioxane (90 mL) slowly to a solution of (3S,4S)-4-(4-bromo-2-nitro-phenylamino)-3-hydroxy-piperidine-1-carboxylic acid tert-butyl ester (0.035 mol, 14.6 g) in dry dichloromethane (50 mL) at room temperature and stir for 16 h. Filter the precipitate and dry under vacuum to obtain the title compound (9.84 g, 80%) as a yellow solid.

PREPARATION 86

(3S,4S)-4-(4-Bromo-2-nitro-phenylamino)-1-methyl-piperidin-3-ol

Add formaldehyde (24 mL, 37-41% aqueous solution) to a solution of (3S,4S)-4-(4-bromo-2-nitro-phenylamino)-piperidin-3-ol, hydrochloride (0.028 mol, 9.8 g) and acetic acid (12 mL) in water (46 mL) and stir the reaction mixture at room temperature for 30 min. Add sodium cyanoborohydride (0.083 mol, 5.26 g) and stir the reaction mixture for 3 h. Quench the reaction mixture with sodium bicarbonate solution and extract with dichloromethane. Dry the organic layer over anhydrous sodium sulfate, filter, and concentrate to obtain the title compound (8.4 g, 92%). $^1$H NMR (400 MHz, CDCl$_3$) δ 1.63-1.71 (m, 1H), 2.16-2.21 (m, 2H), 2.33 (s, 3H), 2.35-2.38 (m, 1H), 2.60 (br s, 1H), 2.80 (d, 1H), 3.54-3.56 (m, 1H), 3.75-3.79 (m, 1H), 6.92 (d, 1H), 7.48 (dd, 1H), 8.14 (d, 1H), 8.30 (d, 1H).

PREPARATION 87

(R)-[4-((E)-3,8-Difluoro-6H-dibenzo[b,e]oxepin-11-ylidenemethyl)-2-nitro-phenyl]-(1-methyl-2-morpholin-4-yl-ethyl)-amine

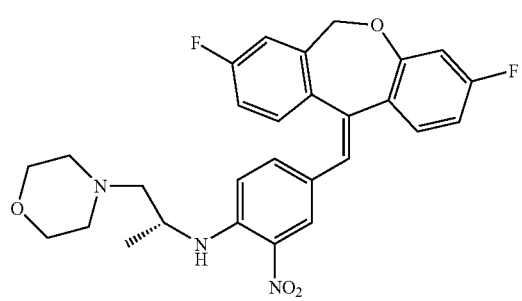

Degas three times a mixture of (R)-(4-bromo-2-nitro-phenyl)-(1-methyl-2-morpholin-4-yl-ethyl)-amine (0.037 mol, 12.8 g), (E)-3,8-difluoro-11-(4,4,5,5-tetramethyl[1,3,2]dioxaborolan-2-ylmethylene)-6,11-dihydro-dibenzo[b,e]oxepine (0.037 mol, 13.7 g), triphenylphosphine (0.007 mol, 2.02 g) and potassium acetate (0.074 mol, 7.29 g) in dioxane/water (3:1) (450 mL) with nitrogen. Add palladium (II) acetate (0.001 mol) to the reaction mixture and degas again three times with nitrogen. Heat the resulting reaction mixture at 85° C. for 16 h. Cool the reaction mixture to room temperature, dilute with water, extract with ethyl acetate, combine organic layer, wash with water and brine. Dry the organic phase over anhydrous sodium sulfate, filter, and concentrate. Purify on a silica gel column using 7% ethyl acetate in hexanes as eluent to obtain the title compound (9.1 g, 48%) as an orange solid. $^1$H NMR (400 MHz, CDCl$_3$), δ 1.26 (d, 3H), 2.44-2.57 (m, 6H), 3.66-3.68 (m, 4H), 3.71-3.78 (m, 1H), 4.89 (br s, 1H), 5.63 (br s, 1H), 6.52 (dd, 1H), 6.61 (d, 1H), 6.67 (dt, 1H), 6.76 (s, 1H), 6.89 (d, 1H), 6.95 (dt, 1H), 7.06-7.10 (m, 1H), 7.19 (dd, 1H), 7.29-7.41 (m, 1H), 7.95 (d, 1H), 8.35 (d, 1H, —NH).

EXAMPLE 1

(E)-N—((R)-5-((E)-3,8-Difluoro-6H-dibenzo[b,e]oxepin-11-ylidenemethyl)-1-(1-methyl-2-morpholin-4-yl-ethyl)-1,3-dihydro-benzoimidazol-2-ylidene)-cyanamide

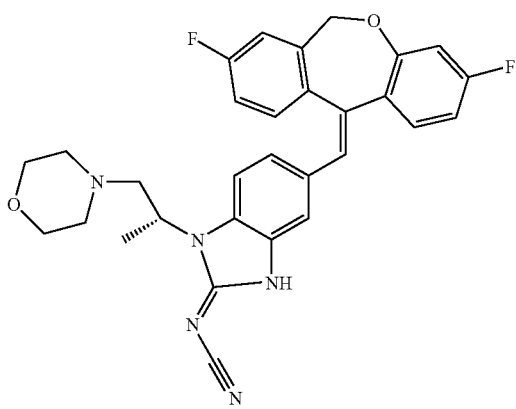

Dissolve (R)-[4-((E)-3,8-difluoro-6H-dibenzo[b,e]oxepin-11-ylidenemethyl)-2-nitro-phenyl]-(1-methyl-2-morpholin-4-yl-ethyl)-amine (0.017 mol, 9.0 g) in tetrahydrofuran (35 mL) and isopropanol (90 mL). Add triethylamine (0.039 mol, 3.9) and 10% platinum on carbon (1.5 g) and hydrogenate in a Parr shaker at 50 psi ($H_2$) at room temperature for 2 h. Filter off the catalyst through a plug of diatomaceous earth. Dilute the filtrate with dioxane (35 mL), add diphenyl N-cyanocarbonimidate (0.019 mol, 4.61 g) and stir at room temperature for 48 h. Concentrate the reaction mixture under reduced pressure. Purify on a silica gel column using 0.5% methanol in dichloromethane as eluent to obtain the title compound (6.0 g, 64%) as an off-white solid. LC-MS m/z 528.2 [M+H]$^+$.

Prepare the following examples in the table below, essentially as described in Preparation 87 and Example 1, using the appropriate phenyl bromide and the appropriate vinyl dioxaborolane.

| Ex | Chemical Name | Structure | Physical Data |
|---|---|---|---|
| 2 | (E)-N-((S)-5-((E)-3-Fluoro-6H-dibenzo[b,e]oxepin-11-ylidenemethyl)-1-(1-methyl-2-morpholin-4-yl-ethyl)-1,3-dihydro-benzoimidazol-2-ylidene)-cyanamide | 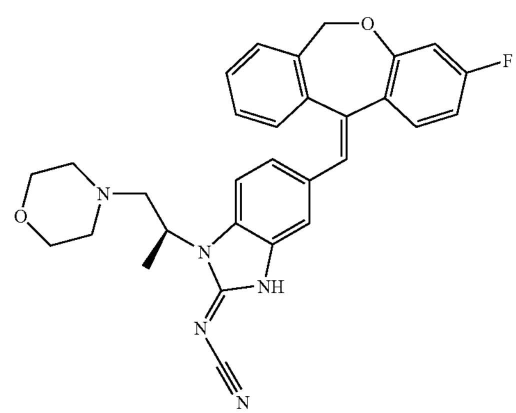 | LC-MS m/z 510.2 [M + H]$^+$ |
| 3 | (E)-N-((R)-5-((E)-3-Fluoro-6H-dibenzo[b,e]oxepin-11-ylidenemethyl)-1-(1-methyl-2-morpholin-4-yl-ethyl)-1,3-dihydro-benzoimidazol-2-ylidene)-cyanamide | 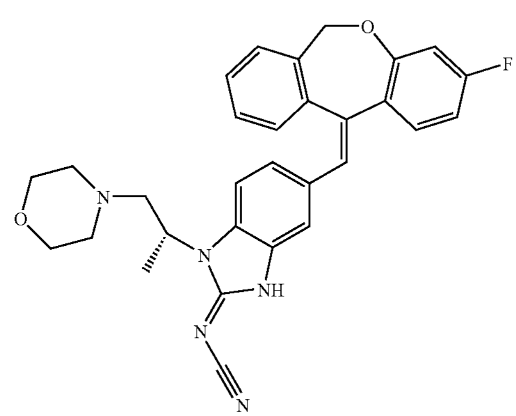 | LC-MS m/z 510.4 [M + H]$^+$ |

-continued

| Ex | Chemical Name | Structure | Physical Data |
|---|---|---|---|
| 4 | (E)-N-((S)-5-((E)-3,8-Difluoro-6H-dibenzo[b,e]oxepin-11-ylidenemethyl)-1-(1-methyl-2-morpholin-4-yl-ethyl)-1,3-dihydro-benzoimidazol-2-ylidene)-cyanamide | 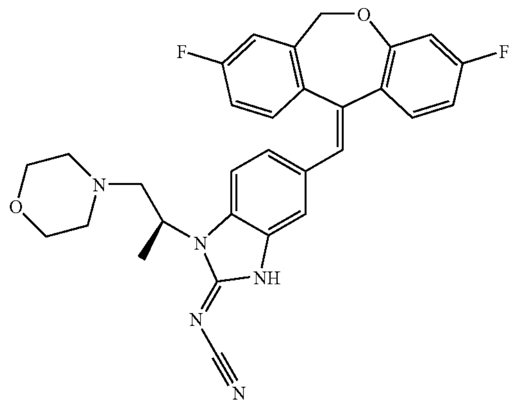 | LC-MS m/z 528.5 [M + H]+ |
| 5 | (E)-N-((R)-5-((E)-3,7-Difluoro-6H-dibenzo[b,e]oxepin-11-ylidenemethyl)-1-(1-methyl-2-morpholin-4-yl-ethyl)-1,3-dihydro-benzoimidazol-2-ylidene)-cyanamide | 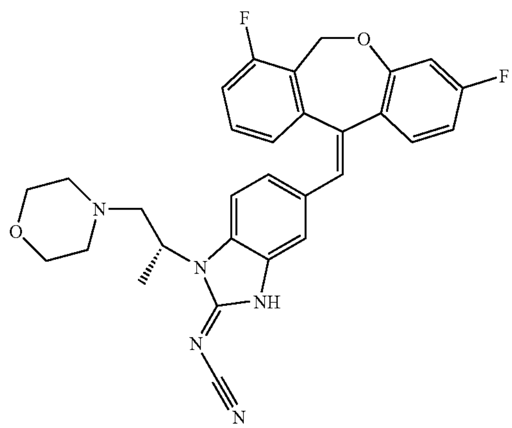 | LC-MS m/z 528.5 [M + H]+ |
| 6 | (E)-N-((S)-5-((E)-3,7-Difluoro-6H-dibenzo[b,e]oxepin-11-ylidenemethyl)-1-(1-methyl-2-morpholin-4-yl-ethyl)-1,3-dihydro-benzoimidazol-2-ylidene)-cyanamide | 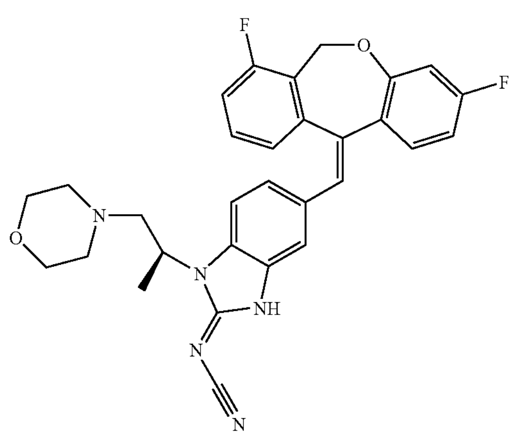 | LC-MS m/z 528.2 [M + H]+ |

PREPARATION 88

[4-((E)-3,7-Difluoro-6H-dibenzo[b,e]oxepin-11-ylidenemethyl)-2-nitro-phenyl]-(4-methyl-piperazin-1-yl)-amine

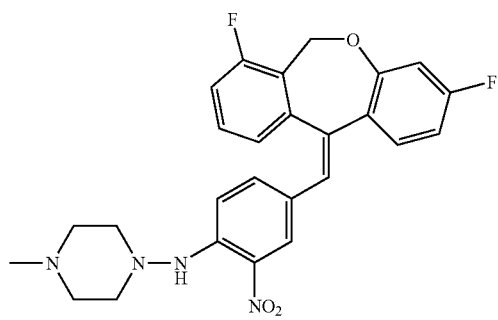

Degas three times a mixture of (4-bromo-2-nitro-phenyl)-(4-methyl-piperazin-1-yl)-amine (0.016 mol, 5.0 g), (E)-3,7-difluoro-11-(4,4,5,5-tetramethyl[1,3,2]dioxaborolan-2-ylmethylene)-6,11-dihydro-dibenzo[b,e]oxepine (0.017 mol, 6.4 g), triphenylphosphine (0.0028 mol, 0.74 g) and potassium acetate (0.0317 mol, 3.11 g) in dioxane/water (3:1) (200 mL) with nitrogen. Add palladium (II) acetate (0.5 mmol, 113 mg) to the reaction mixture and degas again three times with nitrogen. Heat the resulting reaction mixture at 85° C. for 16 h. Cool the reaction mixture to room temperature and dilute with water. Extract the mixture with ethyl acetate, combine organic layers, and wash with water and brine. Dry the organic phase over anhydrous sodium sulfate, filter, and concentrate. Crystallize the crude material from methanol, filter, and dry under vacuum to obtain the title compound (4.2 g, 55%) as an orange solid. ES-MS m/z 479 [M+1]$^+$.

EXAMPLE 7

(E)-N-(5-((E)-3,7-Difluoro-6H-dibenzo[b,e]oxepin-11-ylidenemethyl)-1-(4-methyl-piperazin-1-yl)-1,3-dihydro-benzoimidazol-2-ylidene)-cyanamide

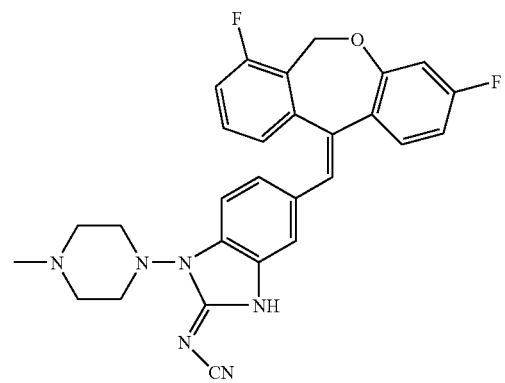

Dissolve [4-((E)-3,7-difluoro-6H-dibenzo[b,e]oxepin-11-ylidenemethyl)-2-nitro-phenyl]-(4-methyl-piperazin-1-yl)-amine (0.008 mol, 3.96 g) in tetrahydrofuran (150 mL). Add triethylamine (0.018 mol, 1.84 g) and 10% platinum on carbon (1.3 g) and hydrogenate in a Parr shaker at 50 psi (H$_2$) at room temperature for 3 h. Filter off the catalyst through a plug of diatomaceous earth, and add pyridine (150 mL) and diphenyl N-cyanocarbonimidate (0.009 mol, 2.17 g). Stir at room temperature for 16 h and then heat to 70° C. for 8 h. Concentrate the reaction mixture under reduced pressure. Purify on a silica gel column using 60% acetone in hexanes as eluent to obtain the title compound (1.8 g, 43%) as an off-white solid. LC-MS m/z 499.2 [M+H]$^+$.

Prepare the following examples in the table below, essentially as described in Preparation 88 and Example 7, using the appropriate phenyl bromide and the appropriate vinyl dioxaborolane.

| Ex | Chemical Name | Structure | Physical Data |
|----|---------------|-----------|---------------|
| 8 | (E)-N-(5-((E)-3-Fluoro-6H-dibenzo[b,e]oxepin-11-ylidenemethyl)-1-(4-methyl-piperazin-1-yl)-1,3-dihydro-benzoimidazol-2-ylidene)-cyanamide | 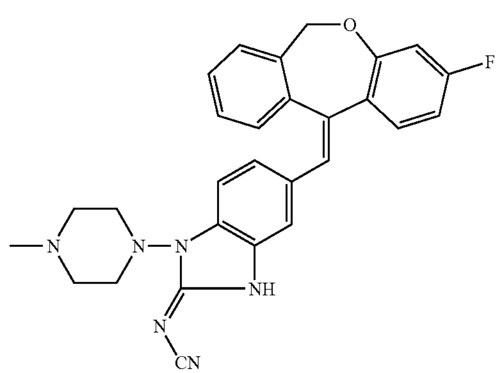 | LC-MS m/z 481.08 [M + H]$^+$ |

-continued

| Ex | Chemical Name | Structure | Physical Data |
|----|---------------|-----------|---------------|
| 9 | (E)-N-(5-((E)-3,8-Difluoro-6H-dibenzo[b,e]oxepin-11-ylidenemethyl)-1-(4-methyl-piperazin-1-yl)-1,3-dihydro-benzoimidazol-2-ylidene)-cyanamide | 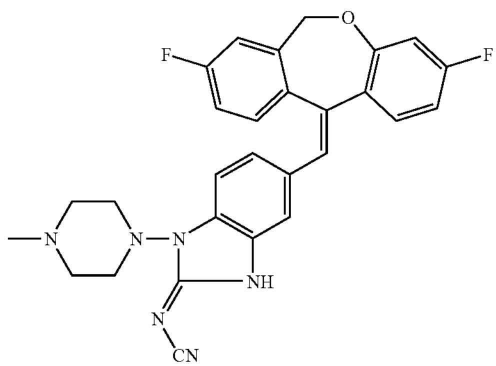 | LC-MS m/z 499.3 [M + H]+ |

EXAMPLE 10

5-((E)-3,8-Difluoro-6H-dibenzo[b,e]oxepin-11-ylidenemethyl)-1,3-dihydro-benzoimidazol-2-ylidene-cyanamide

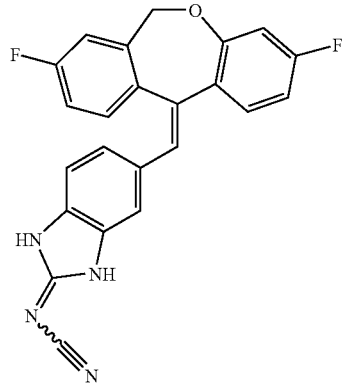

Isolate the title compound as a side-product during the final purification of (E)-N-(5-((E)-3,8-difluoro-6H-dibenzo[b,e]oxepin-11-ylidenemethyl)-1-(4-methyl-piperazin-1-yl)-1,3-dihydro-benzoimidazol-2-ylidene)-cyanamide (Example 9). LC-MS m/z 401.3 [M+H]+.

PREPARATION 89

[4-((E)-3,7-Difluoro-6H-dibenzo[b,e]oxepin-11-ylidenemethyl)-2-nitro-phenyl]-(1-methyl-azetidin-3-yl)-amine

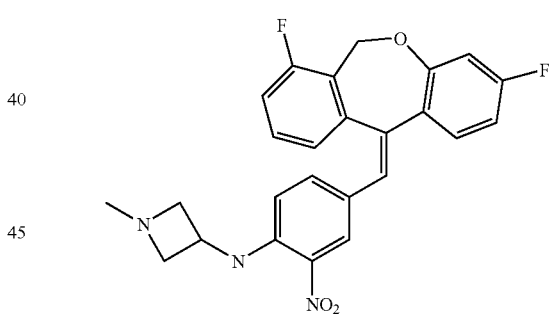

Purge with nitrogen for five min a mixture of (4-bromo-2-nitro-phenyl)-(1-methyl-azetidin-3-yl)-amine (709 µmol, 203 mg), (E)-3,7-difluoro-11-(4,4,5,5-tetramethyl-[1,3,2]dioxaborolan-2-ylmethylene)-6,11-dihydro-dibenzo[b,e]oxepine (723 µmol, 268 mg) in methanol (1.0 mL)/tetrahydrofuran (3.0 mL) (1:3 solvent ratio) in a sealed tube. Add sodium methoxide (1.42 mmol, 77 mg), tetrakis(triphenylphosphine)palladium (35 µmol, 41 mg) and heat at 70° C. overnight. Dilute with ethyl acetate, wash with 10% sodium bicarbonate twice, dry over anhydrous sodium sulfate, filter, and concentrate in vacuo to obtain 377 mg of an orange oil residue. Purify on a 12 g silica gel column eluting with 5% methanol in dichloromethane to obtain the title compound (199 mg, 62%). LC-MS m/z 450.0 [M+H]⁺.

EXAMPLE 11

(E)-N-(5-((E)-3,7-Difluoro-6H-dibenzo[b,e]oxepin-11-ylidenemethyl)-1-(1-methyl-azetidin-3-yl)-1,3-dihydro-benzoimidazol-2-ylidene)-cyanamide

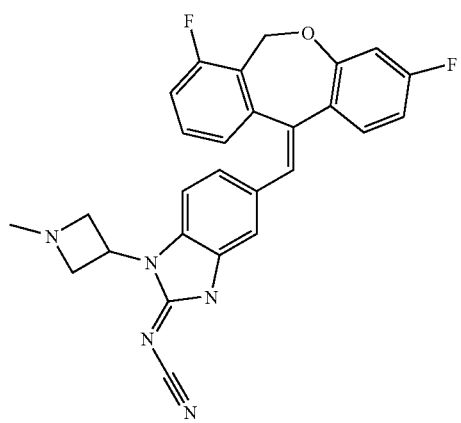

Dissolve [4-((E)-3,7-difluoro-6H-dibenzo[b,e]oxepin-11-ylidenemethyl)-2-nitro-phenyl]-(1-methyl-azetidin-3-yl)-amine (4.23 mmol, 1.90 g), triethylamine (9.31 mmol, 1.30 mL) in tetrahydrofuran (20 mL), add 5% platinum on carbon (200 mg) and hydrogenate (50 psi) at 35° C. for one hour. Filter off the catalyst, rinse with pyridine (20 mL), add diphenyl N-cyanocarbonimidate (4.65 mmol, 1.11 g) and stir at room temperature overnight under nitrogen. Dilute with ethyl acetate, wash with 5% aqueous sodium bicarbonate twice, dry over anhydrous sodium sulfate, filter, and concentrate in vacuo to obtain approximately 3 g of an orange oil. Purify on an 80 g silica gel column eluting with 5% methanol in dichloromethane to obtain ~930 mg of a yellow semi-solid. Dissolve in a minimum amount of methanol and let sit. White solids form. After 30 min filter off the solids and rinse with methanol to obtain the title compound as a white solid (815 mg, 41%). LC-MS m/z 470.2 [M+H]⁺.

Prepare the following Examples in the table below essentially as described in Preparation 89 and Example 11, using the appropriate phenyl bromide and the appropriate vinyl dioxaborolane.

| Ex | Chemical Name | Structure | Physical Data |
|----|---------------|-----------|---------------|
| 12 | (E)-N-(5-((E)-3-Fluoro-6H-dibenzo[b,e]oxepin-11-ylidenemethyl)-1-(1-methyl-azetidin-3-yl)-1,3-dihydro-benzoimidazol-2-ylidene)-cyanamide | 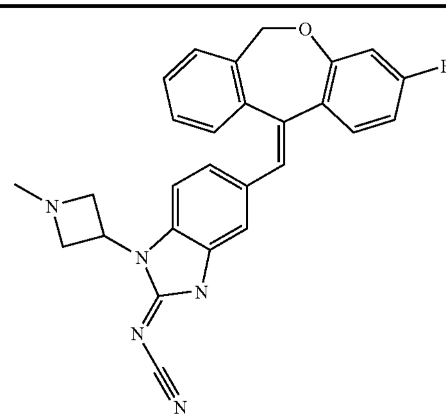 | LC-MS m/z 452.2 [M + H]⁺ |
| 13 | (E)-N-(5-((E)-3,8-Difluoro-6H-dibenzo[b,e]oxepin-11-ylidenemethyl)-1-(1-methyl-azetidin-3-yl)-1,3-dihydro-benzoimidazol-2-ylidene)-cyanamide | 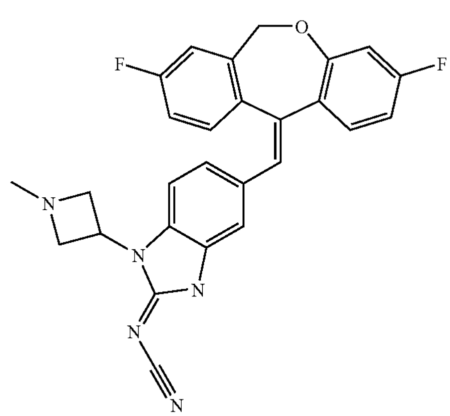 | LC-MS m/z 470.2 [M + H]⁺ |

PREPARATION 90

[4-((E)-3,7-Difluoro-6H-dibenzo[b,e]oxepin-11-ylidenemethyl)-2-nitro-phenyl]-((7S,8aS)-hexahydro-pyrrolo[2,1-c][1,4]oxazin-7-yl)-amine

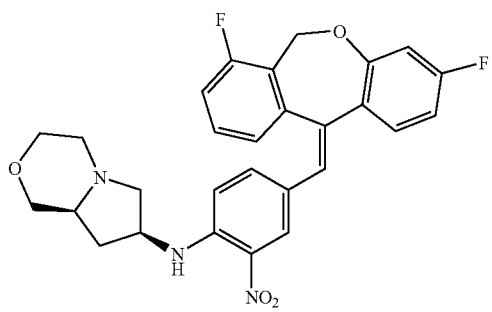

Degas three times a mixture of (4-bromo-2-nitro-phenyl)-((7S,8aS)-hexahydro-pyrrolo[2,1-c][1,4]oxazin-7-yl)-amine (0.011 mol, 4.0 g), (E)-3,7-difluoro-11-(4,4,5,5-tetramethyl[1,3,2]dioxaborolan-2-ylmethylene)-6,11-dihydro-dibenzo[b,e]oxepine (0.012 mol, 4.76 g), triphenylphosphine (0.0031 mol, 0.8 g) and sodium methoxide (0.03 mol, 1.6 g) in tetrahydrofuran/methanol (3:1) (120 mL) with nitrogen. Add palladium (II) acetate (1.0 mmol, 240 mg) to the reaction mixture and degas again three times with nitrogen. Heat the reaction mixture at 70° C. for 4 h. Cool the reaction mixture to room temperature, filter through a plug of diatomaceous earth and concentrate the filtrate under reduced pressure to obtain the title compound (5.0 g, crude).

EXAMPLE 14

(E)-N-(5-((E)-3,7-Difluoro-6H-dibenzo[b,e]oxepin-11-ylidenemethyl)-1-((7S,8aS)-hexahydro-pyrrolo[2,1-c][1,4]oxazin-7-yl)-1,3-dihydro-benzoimidazol-2-ylidene)-cyanamide

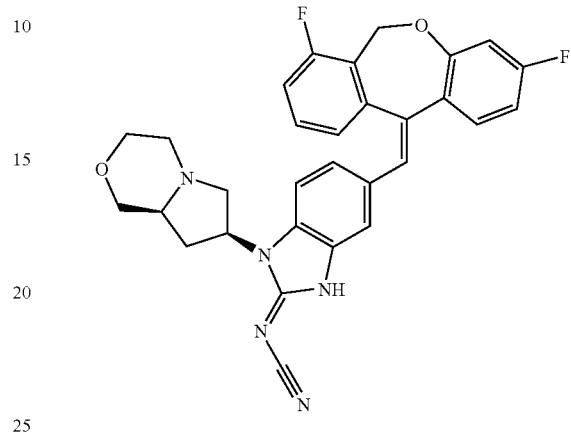

Dissolve [4-((E)-3,7-difluoro-6H-dibenzo[b,e]oxepin-11-ylidenemethyl)-2-nitro-phenyl]-((7S,8aS)-hexahydro-pyrrolo[2,1-c][1,4]oxazin-7-yl)-amine (0.009 mol, 5.0 g) in tetrahydrofuran (40 mL). Add triethylamine (0.009 mol, 0.9 g) and 10% platinum on carbon (1.0 g) and hydrogenate in a Parr shaker at 50 psi ($H_2$) at room temperature for 3 h. Filter off the catalyst through a plug of diatomaceous earth, add pyridine (40 mL) and diphenyl N-cyanocarbonimidate (0.009 mol, 2.35 g) to the filtrate. Stir at room temperature for 16 h, then heat at 60-70° C. for 8 h. Remove the solvent under reduced pressure. Dissolve the resulting residue in dichloromethane and wash with water and saturated sodium bicarbonate solution. Dry the organic layer over anhydrous sodium sulfate, filter, and concentrate under reduced pressure. Purify on a silica gel column using 1% methanol in dichloromethane as eluent to give the title compound (1.9 g, 36%). LC-MS m/z 526.4 [M+H]$^+$.

Prepare the following Examples in the table below essentially as described in Preparation 90 and Example 14, using the appropriate phenyl bromide and the appropriate vinyl dioxaborolane and heating at about 70° C. for 4 to 16 h.

| Ex | Chemical Name | Structure | Physical Data |
|---|---|---|---|
| 15 | (E)-N-(5-((E)-3-Fluoro-6H-dibenzo[b,e]oxepin-11-ylidenemethyl)-1-((7S,8aS)-hexahydro-pyrrolo[2,1-c][1,4]oxazin-7-yl)-1,3-dihydro-benzoimidazol-2-ylidene)-cyanamide | 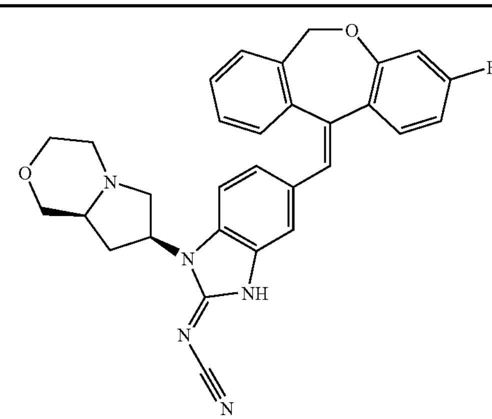 | LC-MS m/z 508.3 [M + H]$^+$ |

-continued

| Ex | Chemical Name | Structure | Physical Data |
|---|---|---|---|
| 16 | (E)-N-(5-((E)-3,8-Difluoro-6H-dibenzo[b,e]oxepin-11-ylidenemethyl)-1-((7S, 8aS)-hexahydro-pyrrolo[2,1-c][1,4]oxazin-7-yl)-1,3-dihydro-benzoimidazol-2-ylidene)-cyanamide | 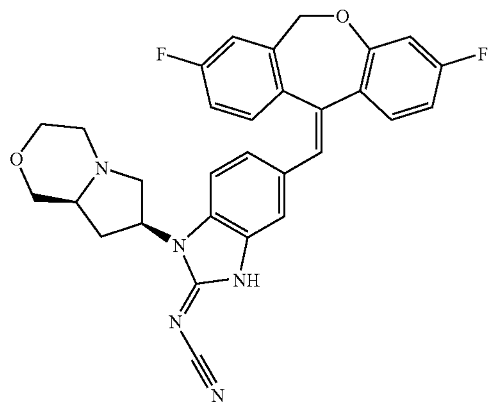 | LC-MS m/z 526.3 [M + H]+ |
| 17 | (E)-N-(5-((E)-3,7-Difluoro-6H-dibenzo[b,e]oxepin-11-ylidenemethyl)-1-((7R, 8aS)-hexahydro-pyrrolo[2,1-c][1,4]oxazin-7-yl)-1,3-dihydro-benzoimidazol-2-ylidene)-cyanamide | 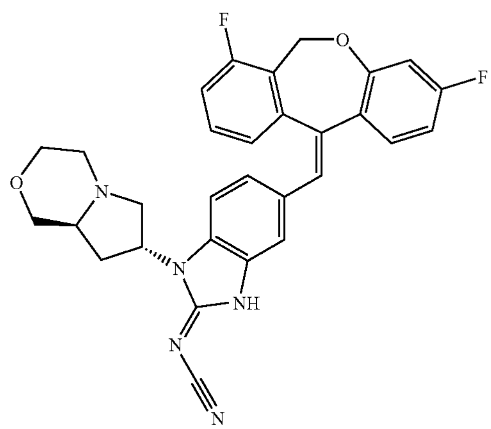 | LC-MS m/z 526.3 [M + H]+ |
| 18 | (E)-N-(5-((E)-3-Fluoro-6H-dibenzo[b,e]oxepin-11-ylidenemethyl)-1-((7R, 8aS)-hexahydro-pyrrolo[2,1-c][1,4]oxazin-7-yl)-1,3-dihydro-benzoimidazol-2-ylidene)-cyanamide | 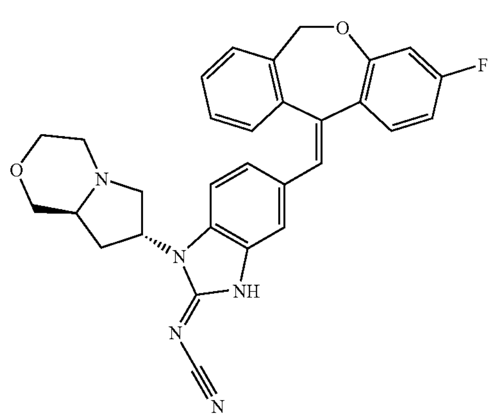 | LC-MS m/z 508.3 [M + H]+ |

-continued

| Ex | Chemical Name | Structure | Physical Data |
|---|---|---|---|
| 19 | (E)-N-(5-((E)-3,8-Difluoro-6H-dibenzo[b,e]oxepin-11-ylidenemethyl)-1-((7R,8aS)-hexahydro-pyrrolo[2,1-c][1,4]oxazin-7-yl)-1,3-dihydro-benzoimidazol-2-ylidene)-cyanamide | 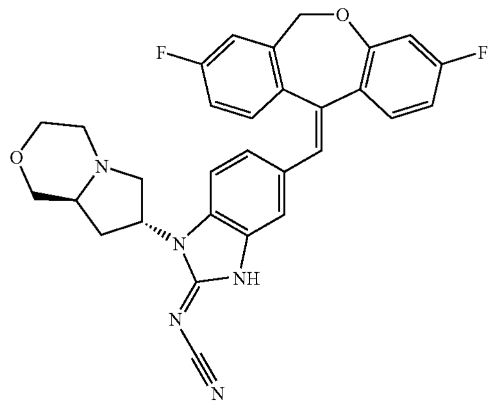 | LC-MS m/z 526.2 [M + H]$^+$ |
| 20 | (E)-N-(5-((E)-3,7-Difluoro-6H-dibenzo[b,e]oxepin-11-ylidenemethyl)-1-((7R,8aR)-hexahydro-pyrrolo[2,1-c][1,4]oxazin-7-yl)-1,3-dihydro-benzoimidazol-2-ylidene)-cyanamide | 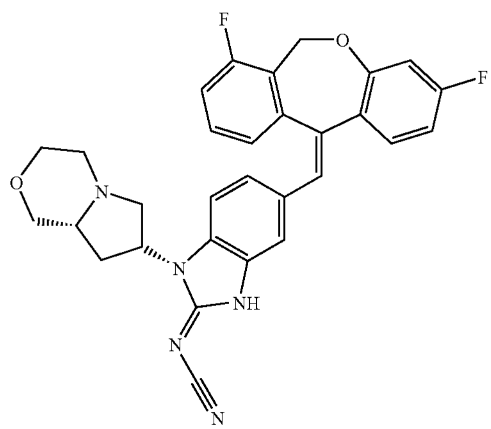 | LC-MS m/z 526.4 [M + H]$^+$ |
| 21 | (E)-N-(5-((E)-3,8-Difluoro-6H-dibenzo[b,e]oxepin-11-ylidenemethyl)-1-((7R,8aR)-hexahydro-pyrrolo[2,1-c][1,4]oxazin-7-yl)-1,3-dihydro-benzoimidazol-2-ylidene)-cyanamide | 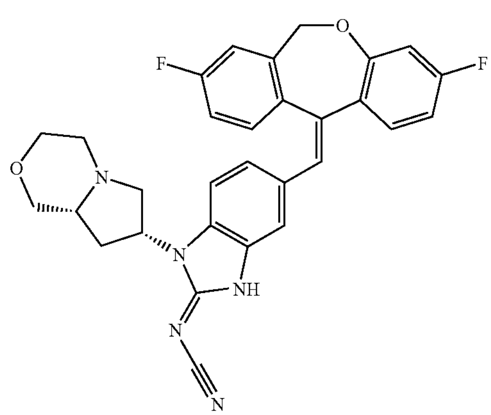 | LC-MS m/z 526.4 [M + H]$^+$ |

-continued

| Ex | Chemical Name | Structure | Physical Data |
|---|---|---|---|
| 22 | (E)-N-(5-((E)-3-Fluoro-6H-dibenzo[b,e]oxepin-11-ylidenemethyl)-1-((7R, 8aR)-hexahydro-pyrrolo[2,1-c][1,4]oxazin-7-yl)-1,3-dihydro-benzoimidazol-2-ylidene)-cyanamide | 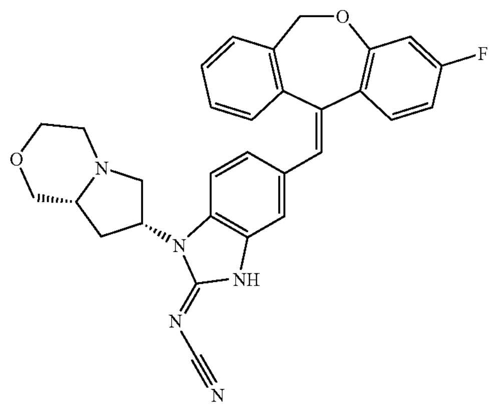 | LC-MS m/z 508.2 [M + H]⁺ |
| 23 | (E)-N-(5-((E)-3,7-Difluoro-6H-dibenzo[b,e]oxepin-11-ylidenemethyl)-1-((7S, 8aR)-hexahydro-pyrrolo[2,1-c][1,4]oxazin-7-yl)-1,3-dihydro-benzoimidazol-2-ylidene)-cyanamide | 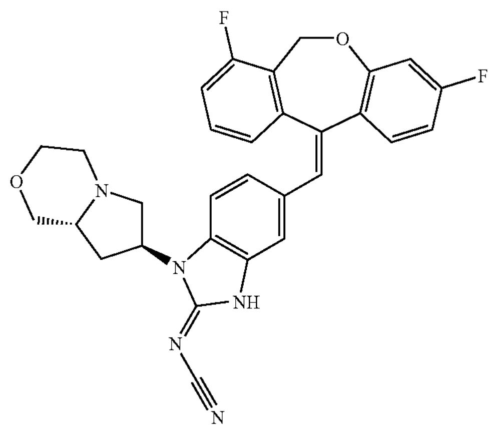 | LC-MS m/z 526.4 [M + H]⁺ |
| 24 | (E)-N-(5-((E)-3,8-Difluoro-6H-dibenzo[b,e]oxepin-11-ylidenemethyl)-1-((7S, 8aR)-hexahydro-pyrrolo[2,1-c][1,4]oxazin-7-yl)-1,3-dihydro-benzoimidazol-2-ylidene)-cyanamide | 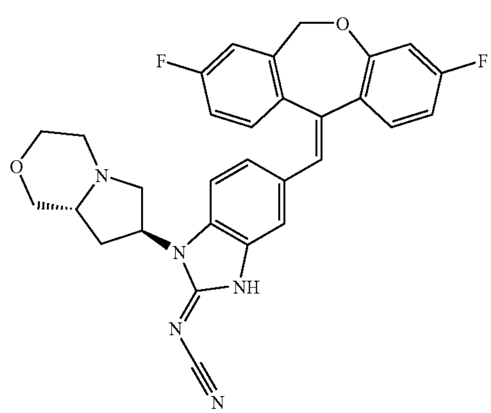 | LC-MS m/z 526.4 [M + H]⁺ |

| Ex | Chemical Name | Structure | Physical Data |
|---|---|---|---|
| 25 | (E)-N-(5-((E)-3-Fluoro-6H-dibenzo[b,e]oxepin-11-ylidenemethyl)-1-((7S,8aR)-hexahydro-pyrrolo[2,1-c][1,4]oxazin-7-yl)-1,3-dihydro-benzoimidazol-2-ylidene)-cyanamide | 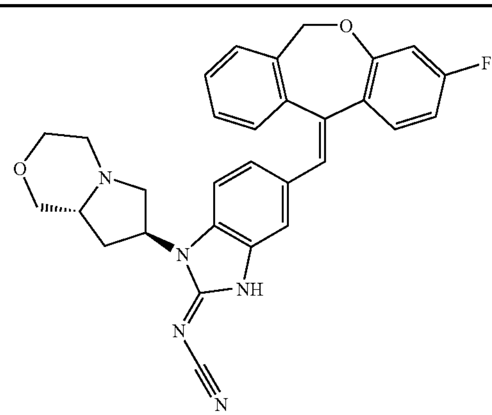 | LC-MS m/z 508.3 [M + H]+ |

PREPARATION 91

(3S,4S)-4-(4-((E)-(3-fluorodibenzo[b,e]oxepin-11(6H)-ylidene)methyl)-2-nitrophenylamino)-1-methylpyrrolidin-3-ol

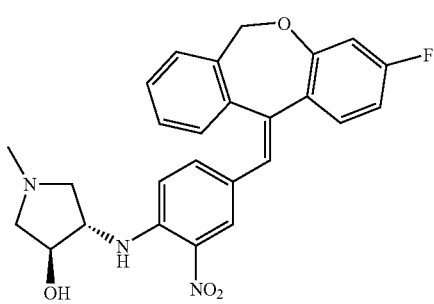

Combine (3S,4S)-4-(4-bromo-2-nitrophenylamino)-1-methylpyrrolidin-3-ol (17.6 mmol, 5.55 g), (E)-2-((3-fluorodibenzo[b,e]oxepin-11(6H)-ylidene)methyl)-4,4,5,5-tetramethyl-1,3,2-dioxaborolane (16.0 mmol, 5.62 g), triphenylphosphine (2.87 mmol, 0.75 g), and K$_2$CO$_3$ (44.7 mmol, 6.18 g) in 110 mL of dioxane:water (3:1). Degas the mixture by bubbling with nitrogen for five min, add palladium (II) acetate (0.48 mmol, 322 mg), and heat at 82° C. under nitrogen for 3.5 h. Cool to room temperature, dilute with water and dichloromethane and then pass through a pad of diatomaceous earth. Separate the phases and extract the aqueous phase with dichloromethane twice. Combine the organic phases, wash with brine, dry over anhydrous sodium sulfate, filter, and remove the solvent in vacuo. Dissolve in 4:1 CH$_2$Cl$_2$/MeOH and pass through a plug of silica using the same solvent. Concentrate the filtrate and triturate with methanol. Collect the resulting solid by filtration to obtain the title compound as a red solid (4.12 g, 56%): $^1$H NMR (300 MHz, CDCl$_3$) δ 2.23 (dd, J=9.9, 5.6 Hz, 1H), 2.38 (s, 3H), 2.28-2.26 (m, 1H), 2.70 (d, J=3.5 Hz, 2H), 3.36 (dd, J=9.8, 7.1 Hz, 1H), 3.91-3.87 (m, 1H), 4.01 (br s, 1H), 5.00-4.80 (m, 1H), 5.70-5.50 (m, 1H), 6.52 (dd, J=10.3, 2.6 Hz, 1H), 6.68-6.64 (m, 1H), 6.78-6.75 (m, 2H), 7.01 (d, J=7.7 Hz, 1H), 7.08 (d, J=7.5 Hz, 1H), 7.24-7.22 (m, 1H), 7.35 (dt, J=7.5, 1.2 Hz, 1H), 7.42 (dd, J=8.7, 6.6 Hz, 1H), 7.47 (d, J=7.4 Hz, 1H), 7.94 (s, 1H), 8.00 (d, J=6.2 Hz, 1H).

EXAMPLE 26

(E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene) cyanamide

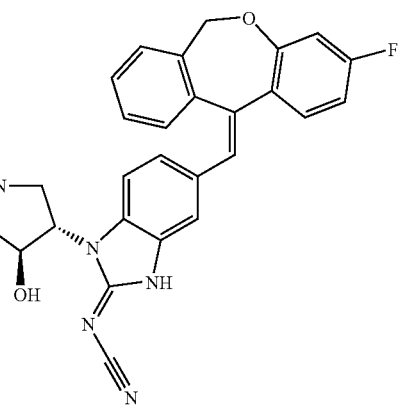

To a solution of (3S,4S)-4-(4-((E)-(3-fluorodibenzo[b,e]oxepin-11(6H)-ylidene)methyl)-2-nitrophenylamino)-1-methylpyrrolidin-3-ol (3.10 mmol, 1.43 g) in isopropanol (85 mL) and triethylamine (9.3 mmol, 1.30 mL) add 5% Pt/C (420 mg) and hydrogenate at 50 psi for 1.5 h. Filter through a plug of diatomaceous earth and wash with isopropanol (50 mL). Add diphenyl cyanocarbonimidate (3.1 mmol, 0.74 g) and stir at room temperature overnight, then heat to reflux for 3 h. Remove the solvent and purify the residue by column chromatography eluting with a gradient from 0% to 20% methanol in methylene chloride to give the title compound as a light brown solid (955 mg, 57%). [α]$_D^{23}$+13.8 (c 0.17, CH$_3$OH); ESI MS m/z 482 [M+H]+.

Prepare the examples below by following the procedures as essentially described for Preparation 91 and Example 26, using the appropriate vinyl bromide and vinyl dioxaborolane and heating at about 80 to 85° C. for 3 to 16 h. Use 5% or 10% platinum on carbon or palladium on carbon for the reduction for about 1-4 h.

| Ex | Chemical Name | Structure | Physical Data |
|---|---|---|---|
| 27 | (E)-N-(5-((E)-(3,7-difluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene)cyanamide | 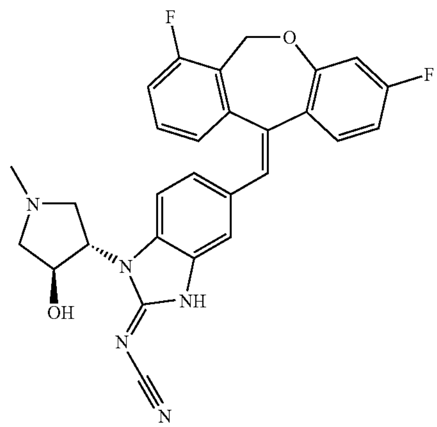 | APCI MS m/z 500 [M + H]$^+$; $[\alpha]_D^{23}$ + 12.8 (c 0.50, CH$_3$OH) |
| 28 | (E)-N-(5-((E)-(3,8-difluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene)cyanamide | 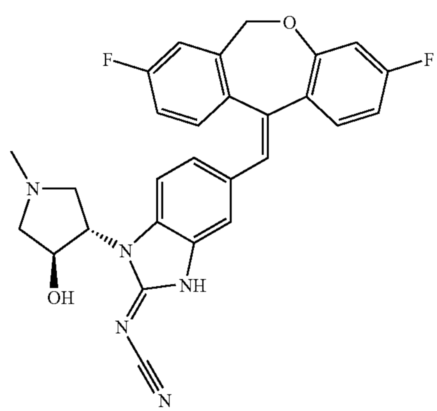 | APCI MS m/z 500 [M + H]$^+$; $[\alpha]_D^{23}$ + 12.6 (c 0.50, CH$_3$OH) |
| 29 | (E)-N-(5-((E)-(3,7-difluorodibenzo[b,e]oxepin-11(6H)-ylidene)methyl)-1-((3R,4R)-4-hydroxy-1-methylpyrrolidin-3-yl)-1H-benzo[d]imidazol-2(3H)-ylidene)cyanamide | 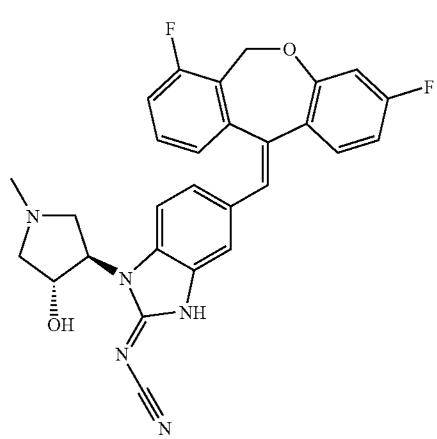 | ESI MS m/z 500 [M + H]$^+$; $[\alpha]_D^{23}$ − 16.2° (c 0.24, CH$_3$OH) |

-continued

| Ex | Chemical Name | Structure | Physical Data |
|---|---|---|---|
| 30* | (E)-N-(5-((E)-(3,8-difluorodibenzo[b,e]oxepin-11(6H)-ylidene)methyl)-1-((3S,4R)-4-hydroxy-1-methylpyrrolidin-3-yl)-1H-benzo[d]imidazol-2(3H)-ylidene)cyanamide | 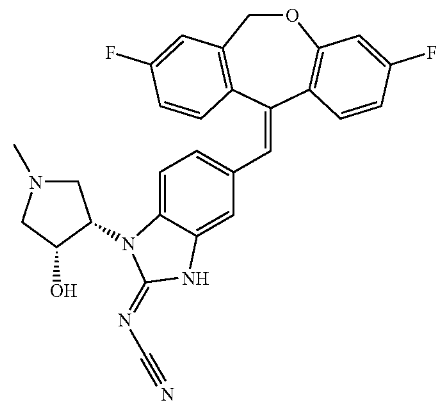 | APCI MS m/z 500 [M + H]$^+$; [α]$_D^{23}$ − 43.6° (c 0.50, CH$_3$OH). |
| 31 | (E)-N-(5-((E)-(3,7-difluorodibenzo[b,e]oxepin-11(6H)-ylidene)methyl)-1-((3R,4S)-4-hydroxy-1-methylpyrrolidin-3-yl)-1H-benzo[d]imidazol-2(3H)-ylidene)cyanamide | 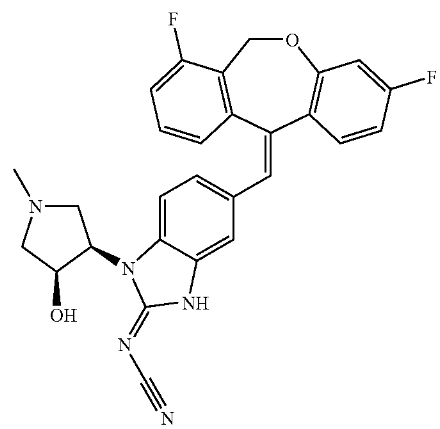 | ESI MS m/z 500 [M + H]$^+$; [α]$_D^{23}$ + 61.0 (c 0.24, CH$_3$OH). |

*Use potassium acetate in the Suzuki coupling reaction.

EXAMPLE 32

(E)-N-(5-((E)-3-Fluoro-6H-dibenzo[b,e]oxepin-11-ylidenemethyl)-1-((3S,4S)-4-hydroxy-1-methyl-1-oxy-pyrrolidin-3-yl)-1,3-dihydro-benzoimidazol-2-ylidene)-cyanamide

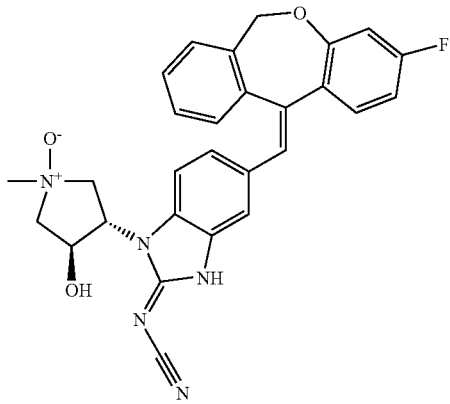

To a solution of (E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2(3H)-lidene)cyanamide (0.27 mmol, 130 mg) in dichloromethane (10 mL) add m-chloroperoxybenzoic acid (0.43 mmol, 93 mg) and stir at room temperature overnight. Load the solution on silica and purify by flash chromatography eluting with 0 to 20% methanol in dichloromethane to obtain the title compound (135 mg, 100%). LC-MS m/z 498.2 [M+H]$^+$.

EXAMPLE 33

(E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene)cyanamide, maleate

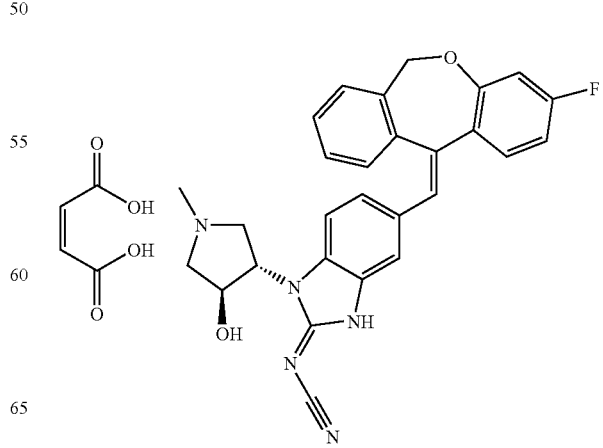

Heat (E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2 (3H)-ylidene)cyanamide (7.10 mmol, 3.42 g) in acetonitrile (60 mL) at 50° C. for 30 min and add (Z)-2-butenedioic acid (7.10 mmol, 837 mg) at once. After a few minutes, the suspension becomes homogeneous and then precipitates start forming. Cool the resulting suspension to room temp. Collect the solid by filtration, wash with acetonitrile (50 mL), and dry in a vacuum oven at 50° C. for 2 h to obtain the title compound (4.1 g, 97%). LC-MS m/z 488.2 [M+H]+. $^1$H NMR (400 MHz, DMSO-$d_6$): 2.80 (s, 3H), 3.77-3.72 (m, 8H), 4.66-4.63 (m, 1H), 4.96-4.91 (m, 1H), 5.16-5.10 (m, 1H), 5.72-5.67 (m, 1H), 5.89-5.82 (m, 1H), 6.00 (s, 2H), 6.59 (dd, J=2.6, 10.5 Hz, 1H), 6.80-6.76 (m, 1H), 6.86 (s, 1H), 6.94-6.90 (m, 2H), 7.02 (s, 1H), 7.22 (td, J=7.5, 1.3 Hz, 1H), 7.30 (d, J=8.8 Hz, 1H), 7.36 (td, J=7.5, 1.3 Hz, 1H), 7.61-7.57 (m, 2H).

Alternate Procedure:

Dissolve (E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene)cyanamide (145 mg) in acetonitrile (5 mL) heat to 50° C. to give a cloudy solution. Dissolve 2-butenedioic acid (35 mg) in THF (300 µL) and slowly add to the acetonitrile to provide a clear solution. Cool the solution to room temperature while stirring to give a precipitate. Continue stirring the solution overnight. Fast filter the resulting solids and dry under vacuum for 2 h at 40° C. Residual acetonitrile was observed in the subsequent TGA (Thermo Gravimetric Analysis) thermogram and the material was dried further overnight.

PREPARATION 92

(3R,4R)-4-[4-((E)-3,7-Difluoro-6H-dibenzo[b,e]oxepin-11-ylidenemethyl)-2-nitro-phenylamino]-1-methyl-piperidin-3-ol

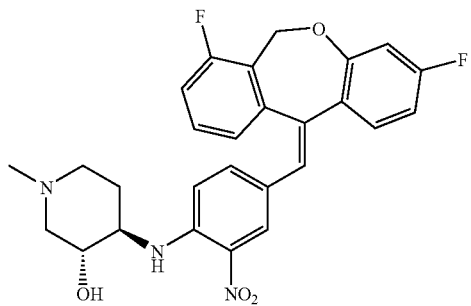

Degas three times a mixture of (3R,4R)-4-(4-bromo-2-nitro-phenylamino)-1-methyl-piperidin-3-ol (0.009 mol, 3.0 g), (E)-3,8-difluoro-11-(4,4,5,5-tetramethyl[1,3,2]dioxaborolan-2-ylmethylene)-6,11-dihydro-dibenzo[b,e]oxepine (0.01 mol, 3.7 g, 1.1 equiv.), triphenylphosphine (0.002 mol, 0.61 g) and sodium methoxide (0.02 mol, 1.2 g) in tetrahydrofuran/methanol (3:1) (150 mL) with nitrogen. Add palladium (II) acetate (0.8 mmol, 183 mg) to the reaction mixture and degas again three times with nitrogen. Heat the reaction mixture at 70° C. for 16 h. Cool the reaction mixture to room temperature, filter through a plug of diatomaceous, and concentrate the filtrate under reduced pressure to obtain the title compound (6.6 g, crude).

EXAMPLE 34

(E)-N-(5-((E)-3,7-Difluoro-6H-dibenzo[b,e]oxepin-11-ylidenemethyl)-1-((3R,4R)-3-hydroxy-1-methyl-piperidin-4-yl)-1,3-dihydro-benzoimidazol-2-ylidene)-cyanamide

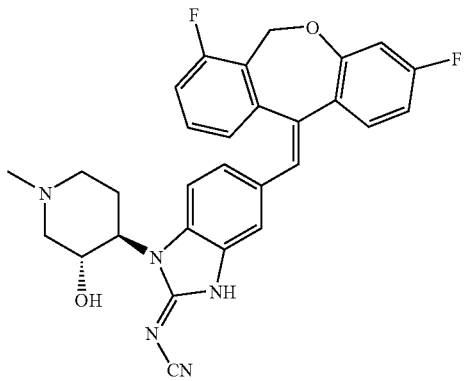

Dissolve (3R,4R)-4-[4-((E)-3,7-Difluoro-6H-dibenzo[b,e]oxepin-11-ylidenemethyl)-2-nitro-phenylamino]-1-methyl-piperidin-3-ol (0.009 mol, 4.48 g) in tetrahydrofuran (100 mL). Add triethylamine (0.018 mol, 1.83 g) and 10% platinum on carbon (2.2 g) and hydrogenate in a Parr shaker at 50 psi ($H_2$) at room temperature for 4 h. Filter off the catalyst through a plug of diatomaceous earth. Add pyridine (100 mL) and diphenyl N-cyanocarbonimidate (0.009 mol, 2.16 g) to the filtrate. Stir at room temperature for 16 h and then heat at 60-70° C. for 8 h. Remove the solvent under reduced pressure. Dissolve the residue in dichloromethane and wash with water and saturated sodium bicarbonate solution. Dry the organic layer over anhydrous sodium sulfate, filter, and concentrate under reduced pressure. Purify on a silica gel column using 5% methanol in dichloromethane as eluent to obtain the title compound (1.2 g, 26%) as an off-white solid. $^1$H NMR (400 MHz, DMSO-$d_6$) δ 1.66-1.8 (m, 1H), 1.75-1.78 (m, 1H), 1.87-1.90 (m, 1H), 2.03 (br s, 1H), 2.24 (s, 3H), 2.81 (br s, 1H), 2.96 (br s, 1H), 3.99 (br s, 1H), 4.31 (br s, 1H), 5.09 (s, 1H), 5.36 (br s, 1H), 5.46 (br s, 1H), 6.68 (dd, 1H), 6.82-6.87 (m, 3H), 6.99 (d, 1H), 7.09 (s, 1H), 7.26-7.35 (m, 3H), 7.62 (t, 1H), 12.49 (br s, 1H).

EXAMPLE 35

(E)-N-(5-((E)-3,7-Difluoro-6H-dibenzo[b,e]oxepin-11-ylidenemethyl)-1-((3S,4S)-3-hydroxy-1-methyl-piperidin-4-yl)-1,3-dihydro-benzoimidazol-2-ylidene)-cyanamide

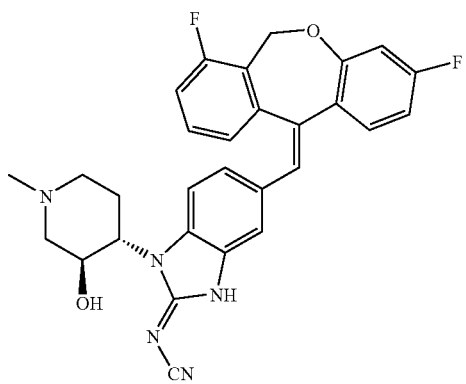

Dissolve 4-[4-((E)-3,7-difluoro-6H-dibenzo[b,e]oxepin-11-ylidenemethyl)-2-nitro-phenylamino]-1-methyl-piperidin-3-ol (0.012 mol, 5.97 g) in tetrahydrofuran (50 mL). Add triethylamine (0.024 mol, 2.44 g) and 10% platinum on carbon (2.9 g) and hydrogenate in a Parr shaker at 50 psi ($H_2$) at room temperature for 4 h. Filter off the catalyst through diatomaceous earth. Add pyridine (50 mL) and diphenyl N-cyanocarbonimidate (0.012 mol, 2.88 g) to the filtrate. Stir at room temperature for 16 h and then heat at 60-70° C. for 8 h. Remove the solvent under reduced pressure, dissolve the residue in dichloromethane and wash with water and saturated sodium bicarbonate solution. Dry the organic layer over anhydrous sodium sulfate, filter, and concentrate under reduced pressure. Purify the residue on a silica gel column using 5% methanol in dichloromethane as eluent to obtain the title compound (1.7 g, 27%) as an off-white solid. LC-MS m/z 514.4 $[M+H]^+$.

Prepare the examples below by following the procedures as essentially described for Preparation 92 and Example 34 and 35, using the appropriate phenyl bromide and vinyl dioxaborolane and heating at about 80 to 85° C. for 3 to 16 h. Use 5% or 10% platinum on carbon or palladium on carbon for the reduction for about 1-4 h.

| Ex | Chemical Name | Structure | Physical Data |
|---|---|---|---|
| 36 | (E)-N-(5-((E)-3-Fluoro-6H-dibenzo[b,e]oxepin-11-ylidenemethyl)-1-((3R,4R)-3-hydroxy-1-methyl-piperidin-4-yl)-1,3-dihydro-benzoimidazol-2-ylidene)-cyanamide | 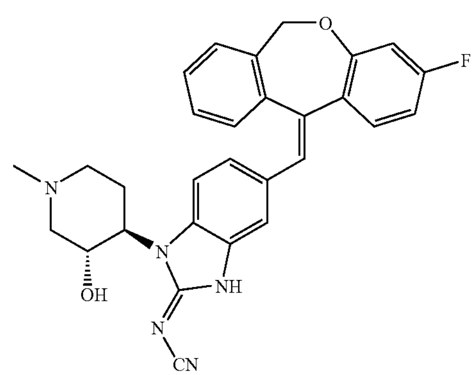 | LCMS m/z 496.5 $[M + H]^+$ |
| 37 | (E)-N-(5-((E)-3,8-Difluoro-6H-dibenzo[b,e]oxepin-11-ylidenemethyl)-1-((3R,4R)-3-hydroxy-1-methyl-piperidin-4-yl)-1,3-dihydro-benzoimidazol-2-ylidene)-cyanamide | 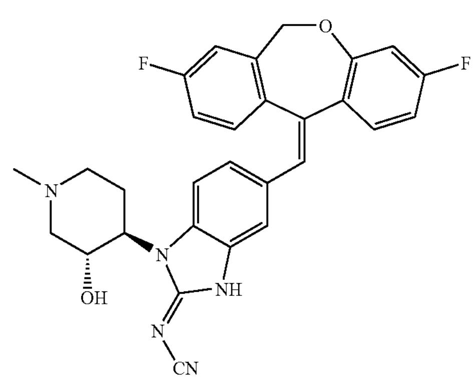 | LCMS m/z 514.5 $[M + H]^+$ |

-continued

| Ex | Chemical Name | Structure | Physical Data |
|---|---|---|---|
| 38 | (E)-N-(5-((E)-3-Fluoro-6H-dibenzo[b,e]oxepin-11-ylidenemethyl)-1-((3S,4S)-3-hydroxy-1-methyl-piperidin-4-yl)-1,3-dihydro-benzoimidazol-2-ylidene)-cyanamide | 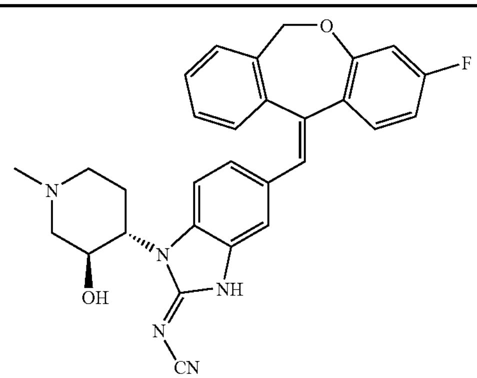 | LCMS m/z 496.5 [M + H]+ |
| 39 | (E)-N-(5-((E)-3,8-Difluoro-6H-dibenzo[b,e]oxepin-11-ylidenemethyl)-1-((3S,4S)-3-hydroxy-1-methyl-piperidin-4-yl)-1,3-dihydro-benzoimidazol-2-ylidene)-cyanamide | 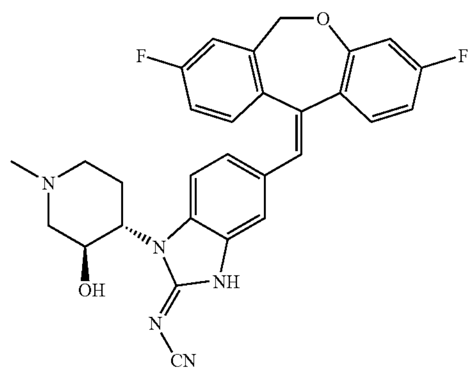 | LCMS m/z 514.5 [M + H]+ |

EXAMPLE 40

(E)-N-(5-((E)-3,7-Difluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea

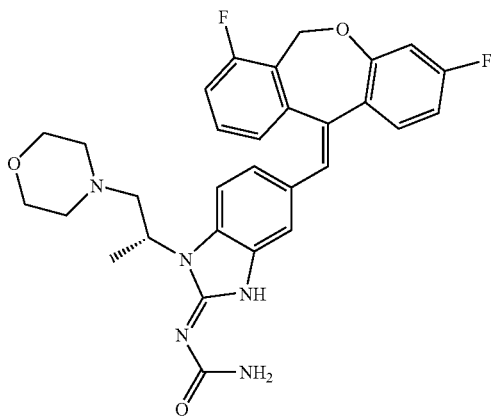

Prepare a solution of 4 M hydrogen chloride in dioxane by diluting 12 M hydrochloric acid (10 mL) with dioxane (20 mL). Slowly add this solution to (E)-N—((R)-5-((E)-3,7-difluoro-6H-dibenzo[b,e]oxepin-11-ylidenemethyl)-1-(1-methyl-2-morpholin-4-yl-ethyl)-1,3-dihydro-benzoimidazol-2-ylidene)-cyanamide (0.005 mol, 3.0 g) at room temperature and stir for 48 hours. Quench the reaction mixture with aqueous 4 N potassium hydroxide solution, extract with dichloromethane and wash with saturated sodium bicarbonate solution. Dry the organic layer over anhydrous sodium sulfate, filter, and concentrate under reduce pressure. Purify on silica gel column using 1% methanol in dichloromethane to obtain the title compound (1.2 g, 38%) as an off-white solid. $^1$H NMR (400 MHz, DMSO-d$_6$) mixture of (E,Z)-N isomers. Major isomer: δ 1.44 (d, 3H), 2.23-2.26 (m, 2H), 2.32-2.33 (m 1H), 2.63 (dd, 1H), 2.77-2.82 (m 1H), 3.29-3.46 (m, 5H), 4.77-4.82 (m, 1H), 5.35-5.44 (br d, 2H), 6.65 (dd, 1H), 6.89 (dt, 3H), 7.13 (s 1H), 7.1 (s, 1H), 7.21-7.28 (m, 2H), 7.31-7.42 (m 1H), 7.55-7.62 (m, 1H), 9.95 (s, 1H). Minor isomer: δ 1.39 (d, 3H, E,Z-isomer), 2.23-2.26 (m, 2H), 2.32-2.33 (m 2H), 2.88-3.0 (m 1H), 3.29-3.46 (m, 5H), 4.80-4.99 (m, 1H), 5.35-5.44 (br d, 2H), 6.65 (dd, 1H), 6.89 (dt, 3H), 7.13 (s 1H), 7.1 (s, 1H), 7.21-7.28 (m, 2H), 7.31-7.42 (m 1H), 7.55-7.62 (m, 1H), 9.95 (s, 1H).

EXAMPLE 41

(E)-N-(5-((E)-3-Fluoro-6H-dibenzo[b,e]oxepin-11-ylidenemethyl)-1-((3S,4S)-4-hydroxy-1-methyl-pyrrolidin-3-yl)-1,3-dihydro-benzoimidazol-2-ylidene)-urea

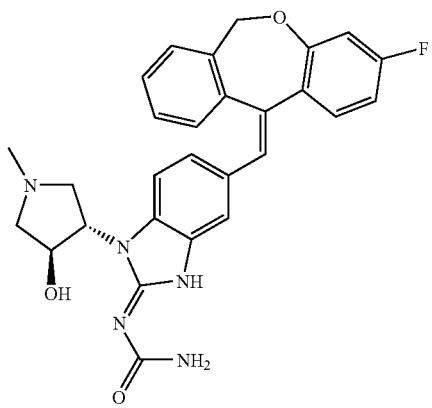

To a mixture of trifluoroacetic acid (30 mL) and water (6.0 eq, 100 mmol, 1.81 mL) in an ice bath add (E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene)cyanamide maleate (16.73 mmol, 10.00 g). Allow the resulting suspension to warm up to room temperature and stir for 2 h. Dilute the solution with ethyl acetate (250 mL), cool the mixture in an ice bath for 30 min, and treat with 5 N sodium hydroxide to pH=11. Wash the organic layer with brine, dry over anhydrous sodium sulfate, and concentrate under reduced pressure. Purify the residue by column chromatography eluting with 2.5 to 5% methanol in ethyl acetate to obtain a white solid. Dry in a vacuum oven at 40° C. overnight to obtain the title compound (6.74 g, 81%). LC-MS m/z 500.2 [M+H]$^+$.

Prepare the examples below by following the procedures as essentially described for Example 40 or 41, using the appropriate cyanoguanidine.

| Ex | Chemical Name | Structure | Physical Data |
|---|---|---|---|
| 42 | (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea | 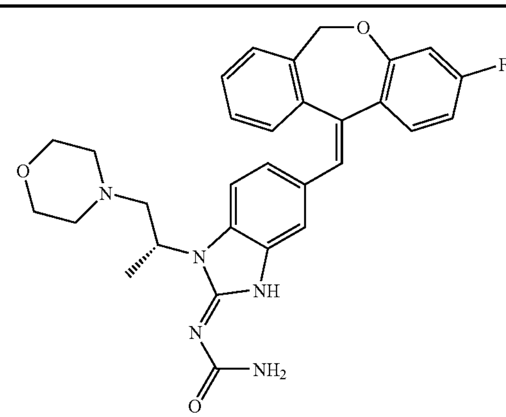 | LCMS m/z 528.2 [M + H]$^+$ |
| 43 | (E)-N-(5-((E)-3,8-Difluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea | 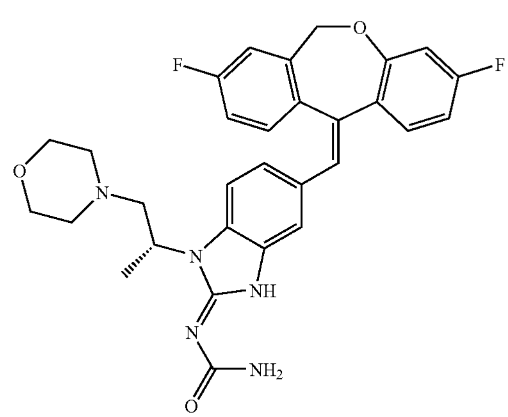 | LCMS m/z 546.2 [M + H]$^+$ |

| Ex | Chemical Name | Structure | Physical Data |
|---|---|---|---|
| 44 | (E)-N-(5-((E)-3,8-Difluoro-6H-dibenzo[b,e]oxepin-11-ylidenemethyl)-1-((3S,4S)-4-hydroxy-1-methyl-pyrrolidin-3-yl)-1,3-dihydro-benzoimidazol-2-ylidene)-urea | 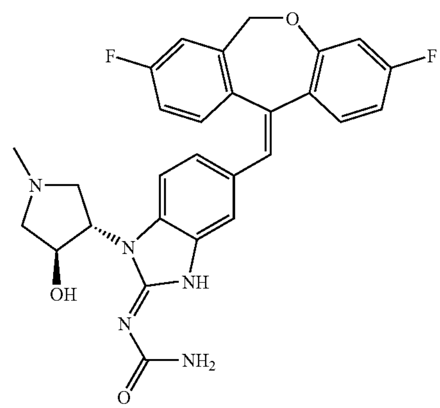 | LCMS m/z 518.5 [M + H]$^+$ |
| 45 | (E)-N-(5-((E)-3,7-Difluoro-6H-dibenzo[b,e]oxepin-11-ylidenemethyl)-1-((3S,4S)-4-hydroxy-1-methyl-pyrrolidin-3-yl)-1,3-dihydro-benzoimidazol-2-ylidene)-urea | 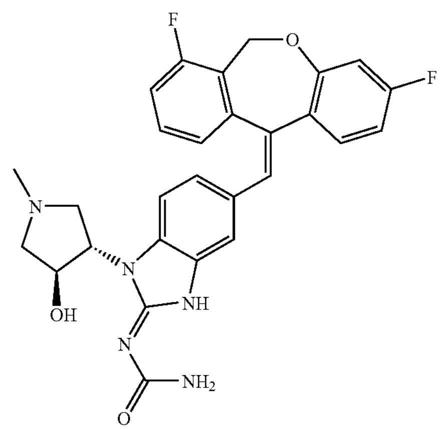 | LCMS m/z 518.6 [M + H]$^+$ |
| 46 | (E)-N-(5-((E)-3,7-Difluoro-6H-dibenzo[b,e]oxepin-11-ylidenemethyl)-1-((3S,4S)-3-hydroxy-1-methyl-pyrrolidin-4-yl)-1,3-dihydro-benzoimidazol-2-ylidene)-urea | 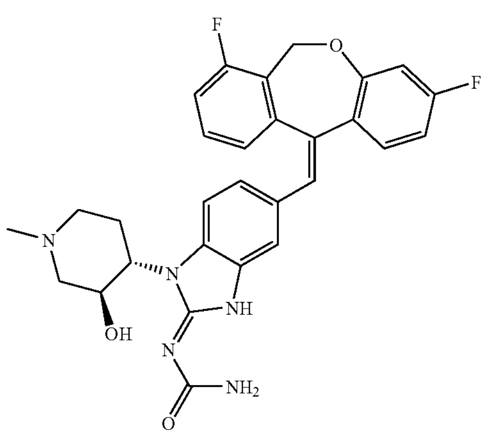 | LCMS m/z 532.6 [M + H]$^+$ |

| Ex | Chemical Name | Structure | Physical Data |
|---|---|---|---|
| 47 | (E)-N-(5-((E)-3,8-Difluoro-6H-dibenzo[b,e]oxepin-11-ylidenemethyl)-1-((3S,4S)-3-hydroxy-1-methyl-pyrrolidin-4-yl)-1,3-dihydro-benzoimidazol-2-ylidene)-urea | 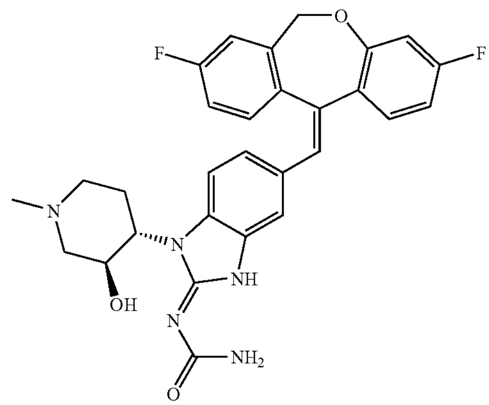 | LCMS m/z 532.6 [M + H]+ |
| 48 | (E)-N-(5-((E)-3-Fluoro-6H-dibenzo[b,e]oxepin-11-ylidenemethyl)-1-((7S, 8aR)-hexahydro-pyrrolo[2,1-c][1,4]oxazin-7-yl)-1,3-dihydro-benzoimidazol-2-ylidene)-urea | 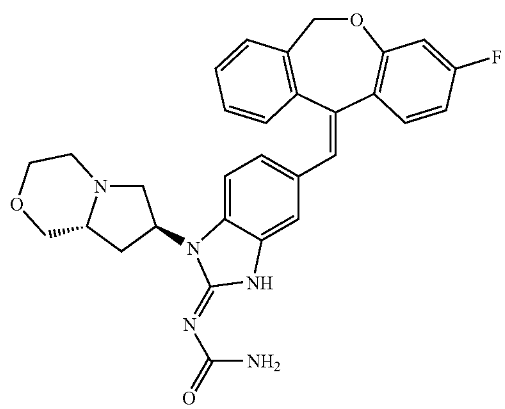 | LCMS m/z 526.6 [M + H]+ |
| 49 | (E)-N-(5-((E)-3,8-Difluoro-6H-dibenzo[b,e]oxepin-11-ylidenemethyl)-1-((7S, 8aR))-hexahydro-pyrrolo[2,1-c][1,4]oxazin-7-yl)-1,3-dihydro-benzoimidazol-2-ylidene)-urea | 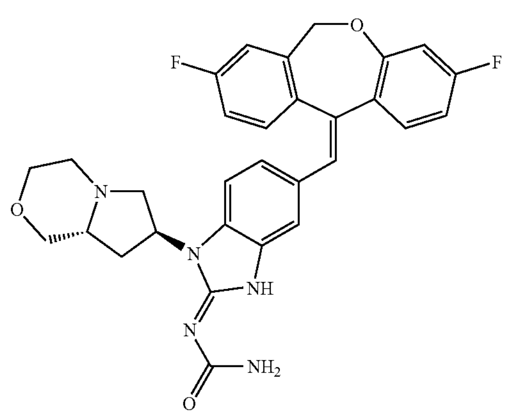 | LCMS m/z 544.6 [M + H]+ |

-continued

| Ex | Chemical Name | Structure | Physical Data |
|---|---|---|---|
| 50 | (E)-N-(5-((E)-3,7-Difluoro-6H-dibenzo[b,e]oxepin-11-ylidenemethyl)-1-((7S, 8aR))-hexahydro-pyrrolo[2,1-c][1,4]oxazin-7-yl)-1,3-dihydro-benzoimidazol-2-ylidene)-urea | 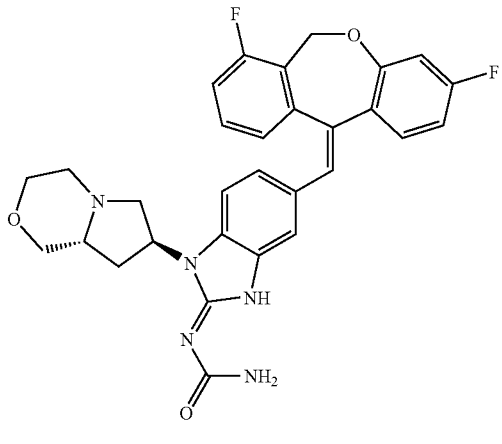 | LCMS m/z 544.6 [M + H]+ |
| 51 | (E)-N-(5-((E)-3-Fluoro-6H-dibenzo[b,e]oxepin-11-ylidenemethyl)-1-((7R, 8aR)-hexahydro-pyrrolo[2,1-c][1,4]oxazin-7-yl)-1,3-dihydro-benzoimidazol-2-ylidene)-urea | 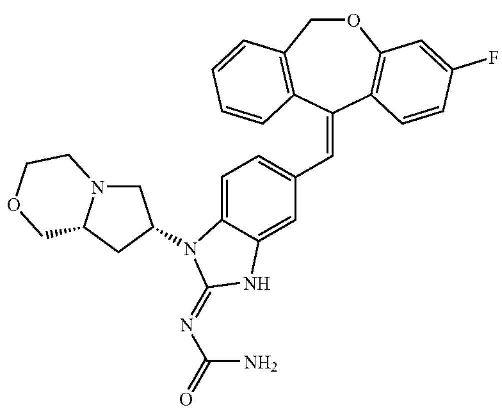 | LCMS m/z 526.6 [M + H]+ |

What is claimed is:

1. A compound of the formula

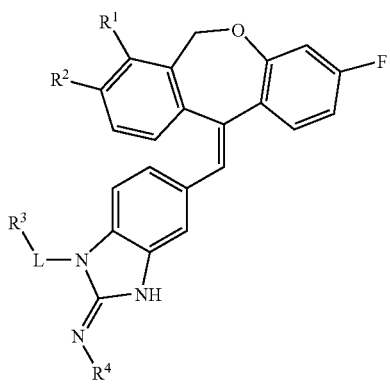

wherein, $R^1$ and $R^2$ each independently represent hydrogen or fluoro;

L represents —(CH$_2$)$_2$—, —CH(CH$_3$)—CH$_2$—, or a direct bond;

$R^3$ represents hydrogen or a group of the formula:

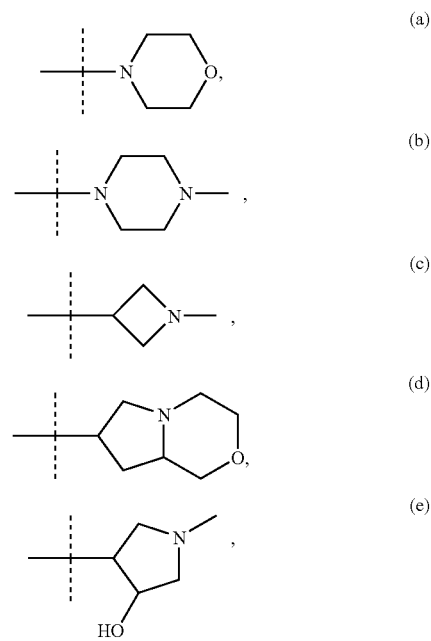

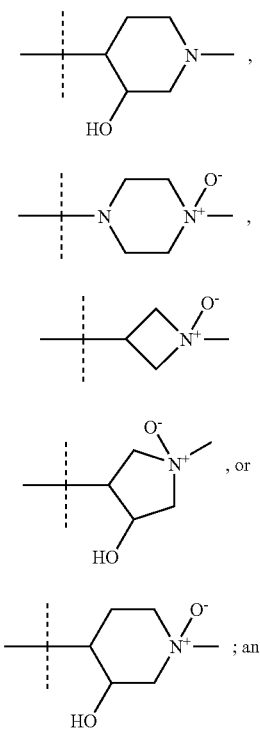

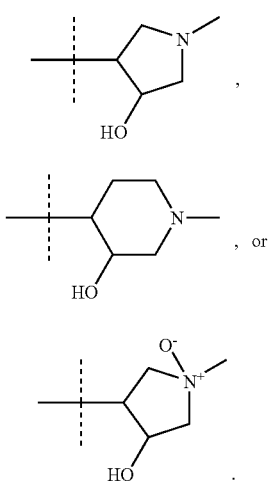

R⁴ represents —CN or —C(O)NH₂, or a pharmaceutically acceptable salt thereof, wherein the compound or pharmaceutically acceptable salt thereof is not in the form of a solvate.

2. The compound or salt according to claim 1 wherein R¹ represents hydrogen and R² represents hydrogen or fluoro.

3. The compound or salt according to claim 1 wherein R¹ represents hydrogen or fluoro and R² represents hydrogen.

4. The compound or salt according to claim 1 wherein R¹ and R² each independently represent hydrogen.

5. The compound or salt according to claim 1 wherein L represents —CH(CH₃)—CH₂— or a direct bond.

6. The compound or salt according to claim 1 wherein R³ represents a group of the formula:

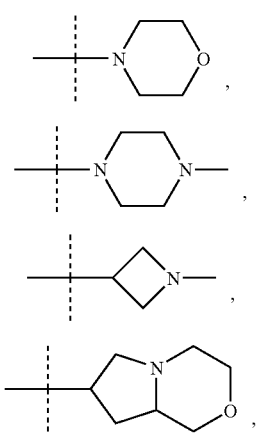

7. The compound or salt according to claim 1 wherein R⁴ represents —CN.

8. The compound or salt according to claim 1 wherein R⁴ represents —C(O)NH₂.

9. The compound or salt according to claim 1 wherein,

R¹ and R² each independently represent hydrogen or fluoro;

L represents —CH(CH₃)—CH₂— or a direct bond;

R³ represents hydrogen or a group of the formula:

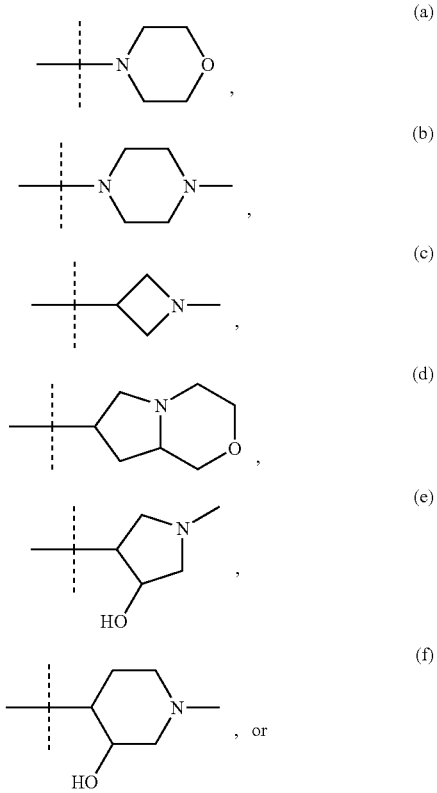

-continued

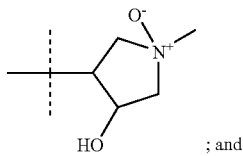

(i)

$R^4$ represents —CN or —C(O)NH$_2$.

10. A compound or salt according to claim 1 selected from the group consisting of (E)-N-(5-((E)-3-Fluoro-6H-dibenzo[b,e]oxepin-11-ylidenemethyl)-1-(1-methyl-azetidin-3-yl)-1,3-dihydro-benzoimidazol-2-ylidene)-cyanamide; (E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene)cyanamide; (E)-N-(5-((E)-(3-fluorodibenzo[b,e]oxepin-11(6H)-ylidene)methyl)-1-((3S,4S)-4-hydroxy-1-methylpyrrolidin-3-yl)-1H-benzo[d]imidazol-2(3H)-ylidene)cyanamide maleate; (E)-N-[5-((E)-3-Fluoro-6H-dibenzo[b,e]oxepin-11-ylidenemethyl)-1-((3S,4S)-4-hydroxy-1-methyl-pyrrolidin-3-yl)-1,3-dihydro-benzoimidazol-2-ylidene]-urea; (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea; and (E)-N-(5-((E)-3-Fluoro-6H-dibenzo[b,e]oxepin-11-ylidenemethyl)-1-((7S,8aR)-hexahydro-pyrrolo[2,1-c][1,4]oxazin-7-yl)-1,3-dihydro-benzoimidazol-2-ylidene)-urea.

11. The compound according to claim 1 that is (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea, or a pharmaceutically acceptable salt thereof.

12. The compound according to claim 11 that is (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea.

13. A method of treating congestive heart failure, diabetic nephropathy, chronic kidney disease, hypertension, hypokalemia, myocardial arrhythmia, Bartter's Syndrome, primary or secondary hyperaldosteronism, or Conn's Syndrome, comprising administering to a patient in need thereof an effective amount of a compound or salt according to claim 1.

14. The method according to claim 13 for treating congestive heart failure, hypertension, diabetic nephropathy, or chronic kidney disease.

15. The method according to claim 14 comprising administering to a patient in need thereof and effective amount of a compound that is (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea, or a pharmaceutically acceptable salt thereof.

16. The method according to claim 15 comprising administering to a patient in need thereof and effective amount of a compound that is (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea.

17. A pharmaceutical composition comprising a compound or salt according to claim 1 in combination with one or more pharmaceutically acceptable carriers, diluents, or excipients.

18. The composition according to claim 17 comprising a compound that is (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea, or a pharmaceutically acceptable salt thereof.

19. The composition according to claim 18 comprising a compound that is (E)-N-(5-((E)-3-Fluoro-6H-dibenzo[b,e]oxepin-11-ylidenemethyl)-1-((R)-1-methyl-2-morpholin-4-yl-ethyl)-1,3-dihydro-benzoimidazol-2-ylidene)-urea.

* * * * *

UNITED STATES PATENT AND TRADEMARK OFFICE
CERTIFICATE OF CORRECTION

PATENT NO. : 7,994,164 B2
APPLICATION NO. : 12/330539
DATED : August 9, 2011
INVENTOR(S) : Konstantinos Gavardinas and Prabhakar Kondaji Jadhav It is certified that error appears in the above-identified patent and that said Letters Patent is hereby corrected as shown below:

Title Page, Item (56), column 2 (Other Publications), line 1, please delete "Solid-Sate" and insert --Solid-State--, therefor.

Title Page, Item (56), column 2 (Other Publications), line 8, please delete "Atlants" and insert --Atlanta--, therefor.

Title Page, Item (56), column 2 (Other Publications), line 10, please delete "Mineralcorticoid" and insert --Mineralocorticoid--, therefor.

Signed and Sealed this
Twenty-ninth Day of November, 2011

David J. Kappos
*Director of the United States Patent and Trademark Office*